(12) United States Patent
Firestein-Miller

(10) Patent No.: US 7,790,843 B2
(45) Date of Patent: Sep. 7, 2010

(54) CYPIN POLYPEPTIDE AND FRAGMENTS THEREOF

(76) Inventor: Bonnie L. Firestein-Miller, 300 E. Mountain Rd., Hillsborough, NJ (US) 08844

( * ) Notice: Subject to any disclaimer, the term of this patent is extended or adjusted under 35 U.S.C. 154(b) by 0 days.

(21) Appl. No.: 12/008,873

(22) Filed: Jan. 15, 2008

(65) Prior Publication Data

US 2008/0182970 A1    Jul. 31, 2008

Related U.S. Application Data

(62) Division of application No. 11/033,909, filed on Jan. 12, 2005, now Pat. No. 7,338,769.

(60) Provisional application No. 60/535,512, filed on Jan. 12, 2004, provisional application No. 60/535,533, filed on Jan. 12, 2004, provisional application No. 60/535,534, filed on Jan. 12, 2004, provisional application No. 60/577,932, filed on Jun. 9, 2004.

(51) Int. Cl.
*A61K 38/00* (2006.01)
*A61K 39/00* (2006.01)
*C07K 16/00* (2006.01)
*C07K 1/00* (2006.01)
*A01N 37/18* (2006.01)

(52) U.S. Cl. ............... 530/300; 530/324; 530/350; 424/184.1; 424/185.1; 514/2; 514/12

(58) Field of Classification Search ............... None
See application file for complete search history.

(56) References Cited

FOREIGN PATENT DOCUMENTS

| WO | WO99/43702 | * | 9/1999 |
|---|---|---|---|
| WO | WO9943702 | * | 9/1999 |

OTHER PUBLICATIONS

Park et al., 2001, UniProtB/TrEMBL Q9H335 human.*

* cited by examiner

*Primary Examiner*—Olga N Chernyshev
(74) *Attorney, Agent, or Firm*—Fox Rothschild LLP; Gerard P. Norton; Roman Fayerberg

(57) ABSTRACT

Disclosed are novel materials and screening methods for diagnosing and monitoring cognitive disorders, as well as for identifying compounds for treating such disorders.

8 Claims, No Drawings

SEQUENCE LISTING

<160> NUMBER OF SEQ ID NOS: 24

<210> SEQ ID NO 1
<211> LENGTH: 454
<212> TYPE: PRT
<213> ORGANISM: Homo sapiens

<400> SEQUENCE: 1

```
Met Cys Ala Ala Gln Met Pro Pro Leu Ala His Ile Phe Arg Gly Thr
1               5                   10                  15

Phe Val His Ser Thr Trp Thr Cys Pro Met Glu Val Leu Arg Asp His
                20                  25                  30

Leu Leu Gly Val Ser Asp Ser Gly Lys Ile Val Phe Leu Glu Glu Ala
            35                  40                  45

Ser Gln Gln Glu Lys Leu Ala Lys Glu Trp Cys Phe Lys Pro Cys Glu
    50                  55                  60

Ile Arg Glu Leu Ser His His Glu Phe Phe Met Pro Gly Leu Val Asp
65                  70                  75                  80

Thr His Ile His Ala Ser Gln Tyr Ser Phe Ala Gly Ser Ser Ile Asp
                85                  90                  95

Leu Pro Leu Leu Glu Trp Leu Thr Lys Tyr Thr Phe Pro Ala Glu His
                100                 105                 110

Arg Phe Gln Asn Ile Asp Phe Ala Glu Glu Val Tyr Thr Arg Val Val
            115                 120                 125

Arg Arg Thr Leu Lys Asn Gly Thr Thr Thr Ala Cys Tyr Phe Ala Thr
    130                 135                 140

Ile His Thr Asp Ser Ser Leu Leu Leu Ala Asp Ile Thr Asp Lys Phe
145                 150                 155                 160

Gly Gln Arg Ala Phe Val Gly Lys Val Cys Met Asp Leu Asn Asp Thr
                165                 170                 175

Phe Pro Glu Tyr Lys Glu Thr Thr Glu Glu Ser Ile Lys Glu Thr Glu
                180                 185                 190

Arg Phe Val Ser Glu Met Leu Gln Lys Asn Tyr Ser Arg Val Lys Pro
            195                 200                 205

Ile Val Thr Pro Arg Phe Ser Leu Ser Cys Ser Glu Thr Leu Met Gly
    210                 215                 220
```

```
Glu Leu Gly Asn Ile Ala Lys Thr Arg Asp Leu His Ile Gln Ser His
225                 230                 235                 240

Ile Ser Glu Asn Arg Asp Glu Val Glu Ala Val Lys Asn Leu Tyr Pro
                245                 250                 255

Ser Tyr Lys Asn Tyr Thr Ser Val Tyr Asp Lys Asn Asn Leu Leu Thr
            260                 265                 270

Asn Lys Thr Val Met Ala His Gly Cys Tyr Leu Ser Ala Glu Glu Leu
        275                 280                 285

Asn Val Phe His Glu Arg Gly Ala Ser Ile Ala His Cys Pro Asn Ser
    290                 295                 300

Asn Leu Ser Leu Ser Ser Gly Phe Leu Asn Val Leu Glu Val Leu Lys
305                 310                 315                 320

His Glu Val Lys Ile Gly Leu Gly Thr Asp Val Ala Gly Gly Tyr Ser
                325                 330                 335

Tyr Ser Met Leu Asp Ala Ile Arg Arg Ala Val Met Val Ser Asn Ile
            340                 345                 350

Leu Leu Ile Asn Lys Val Asn Glu Lys Ser Leu Thr Leu Lys Glu Val
        355                 360                 365

Phe Arg Leu Ala Thr Leu Gly Gly Ser Gln Ala Leu Gly Leu Asp Gly
370                 375                 380

Glu Ile Gly Asn Phe Glu Val Gly Lys Glu Phe Asp Ala Ile Leu Ile
385                 390                 395                 400

Asn Pro Lys Ala Ser Asp Ser Pro Ile Asp Leu Phe Tyr Gly Asp Phe
                405                 410                 415

Phe Gly Asp Ile Ser Glu Ala Val Ile Gln Lys Phe Leu Tyr Leu Gly
            420                 425                 430

Asp Asp Arg Asn Ile Glu Glu Val Tyr Val Gly Lys Gln Val Val
        435                 440                 445

Pro Phe Ser Ser Ser Val
    450

<210> SEQ ID NO 2
<211> LENGTH: 5451
<212> TYPE: PRT
<213> ORGANISM: Homo sapiens

<400> SEQUENCE: 2

Gly Thr Ala Gly Gly Ala Gly Cys Cys Ala Gly Cys Cys Cys Cys
1               5                   10                  15

Thr Gly Gly Gly Cys Gly Cys Gly Gly Cys Cys Thr Gly Cys Ala Gly
                20                  25                  30

Gly Gly Thr Ala Cys Cys Gly Gly Cys Ala Ala Cys Cys Gly Cys Cys
            35                  40                  45

Cys Gly Gly Gly Thr Ala Ala Gly Cys Gly Gly Gly Gly Cys Ala
    50                  55                  60

Gly Gly Ala Cys Ala Ala Gly Gly Cys Cys Gly Gly Ala Gly Cys Cys
65                  70                  75                  80

Thr Gly Thr Gly Thr Cys Cys Gly Cys Cys Gly Gly Cys Ala Gly
                85                  90                  95

Cys Cys Gly Cys Cys Gly Cys Ala Gly Cys Thr Gly Cys Ala Gly
            100                 105                 110

Ala Gly Ala Gly Thr Cys Cys Cys Gly Cys Thr Gly Cys Gly Thr Cys
        115                 120                 125

Thr Cys Cys Gly Cys Cys Gly Cys Gly Thr Gly Cys Gly Cys Cys Cys
```

-continued

```
            130                 135                 140
Thr Cys Cys Thr Cys Gly Ala Cys Cys Ala Gly Cys Ala Gly Ala Cys
145                 150                 155                 160

Cys Cys Gly Cys Gly Cys Thr Gly Cys Gly Cys Thr Cys Cys Gly Cys
                165                 170                 175

Cys Gly Cys Thr Gly Ala Cys Ala Thr Gly Thr Gly Thr Gly Cys Cys
                180                 185                 190

Gly Cys Thr Cys Ala Gly Ala Thr Gly Cys Gly Cys Cys Cys Cys Cys
                195                 200                 205

Thr Gly Gly Cys Gly Cys Ala Cys Ala Thr Cys Thr Thr Cys Cys Gly
210                 215                 220

Ala Gly Gly Ala Cys Gly Thr Thr Cys Gly Thr Cys Cys Ala Cys Cys
225                 230                 235                 240

Thr Cys Cys Ala Cys Cys Thr Gly Gly Ala Cys Cys Thr Gly Cys Cys
                245                 250                 255

Cys Cys Ala Thr Gly Gly Ala Gly Gly Thr Gly Cys Thr Gly Cys Gly
                260                 265                 270

Gly Gly Ala Thr Cys Ala Cys Cys Thr Cys Cys Thr Cys Gly Gly Cys
                275                 280                 285

Gly Thr Gly Ala Gly Cys Gly Ala Cys Ala Gly Cys Gly Gly Cys Ala
                290                 295                 300

Ala Ala Ala Thr Ala Gly Thr Gly Thr Thr Thr Thr Thr Ala Gly Ala
305                 310                 315                 320

Ala Gly Ala Ala Gly Cys Ala Thr Cys Thr Cys Ala Ala Cys Ala Gly
                325                 330                 335

Gly Ala Ala Ala Ala Cys Thr Gly Gly Cys Cys Ala Ala Ala Ala Gly
                340                 345                 350

Ala Ala Thr Gly Gly Thr Gly Cys Thr Thr Cys Ala Ala Gly Cys Cys
                355                 360                 365

Gly Thr Gly Thr Gly Ala Ala Ala Thr Ala Ala Gly Ala Gly Ala Ala
                370                 375                 380

Cys Thr Gly Ala Gly Cys Cys Ala Cys Cys Ala Thr Gly Ala Gly Thr
385                 390                 395                 400

Thr Cys Thr Thr Cys Ala Thr Gly Cys Thr Gly Gly Gly Cys Thr
                405                 410                 415

Gly Gly Thr Thr Gly Ala Thr Ala Cys Ala Cys Ala Cys Ala Thr Cys
                420                 425                 430

Cys Ala Thr Gly Cys Cys Thr Cys Thr Cys Ala Gly Thr Ala Thr Thr
                435                 440                 445

Cys Cys Thr Thr Gly Cys Thr Gly Gly Ala Ala Gly Thr Ala Gly
                450                 455                 460

Cys Ala Thr Ala Gly Ala Cys Cys Thr Gly Cys Cys Ala Cys Thr Cys
465                 470                 475                 480

Thr Thr Gly Gly Ala Gly Thr Gly Gly Cys Gly Ala Cys Cys Ala
                485                 490                 495

Ala Gly Thr Ala Cys Ala Cys Ala Thr Thr Cys Cys Thr Gly Cys
                500                 505                 510

Ala Gly Ala Ala Cys Ala Cys Ala Gly Ala Thr Thr Cys Cys Ala Gly
                515                 520                 525

Ala Ala Cys Ala Thr Cys Gly Ala Cys Thr Thr Gly Cys Ala Gly
                530                 535                 540

Ala Ala Gly Ala Ala Gly Thr Ala Thr Ala Thr Ala Cys Cys Ala Gly
545                 550                 555                 560
```

-continued

Ala Gly Thr Thr Gly Thr Cys Ala Gly Gly Ala Ala Cys Ala
            565                 570                 575

Cys Thr Ala Ala Ala Gly Ala Ala Thr Gly Gly Ala Ala Cys Ala Ala
            580                 585                 590

Cys Cys Ala Cys Ala Gly Cys Thr Thr Gly Thr Thr Ala Cys Thr Thr
            595                 600                 605

Thr Gly Cys Ala Ala Cys Ala Ala Thr Cys Ala Cys Ala Cys Thr
        610                 615                 620

Gly Ala Cys Thr Cys Ala Thr Cys Thr Cys Thr Gly Cys Thr Cys Cys
625                 630                 635                 640

Thr Thr Gly Cys Cys Gly Ala Cys Ala Thr Thr Ala Cys Ala Gly Ala
            645                 650                 655

Thr Ala Ala Ala Thr Thr Thr Gly Gly Ala Cys Ala Gly Cys Gly Gly
            660                 665                 670

Gly Cys Ala Thr Thr Thr Gly Thr Gly Gly Gly Cys Ala Ala Ala Gly
            675                 680                 685

Thr Thr Thr Gly Cys Ala Thr Gly Gly Ala Thr Thr Gly Ala Ala
        690                 695                 700

Thr Gly Ala Cys Ala Cys Thr Thr Thr Cys Ala Gly Ala Ala
705                 710                 715                 720

Thr Ala Cys Ala Ala Gly Gly Ala Gly Ala Cys Cys Ala Cys Thr Gly
            725                 730                 735

Ala Gly Gly Ala Ala Thr Cys Gly Ala Thr Cys Ala Ala Gly Gly Ala
            740                 745                 750

Ala Ala Cys Thr Gly Ala Gly Ala Gly Ala Thr Thr Gly Thr Gly
            755                 760                 765

Thr Cys Ala Gly Ala Ala Ala Thr Gly Cys Thr Cys Cys Ala Ala Ala
            770                 775                 780

Ala Gly Ala Ala Cys Thr Ala Thr Thr Cys Thr Ala Gly Ala Gly Thr
785                 790                 795                 800

Gly Ala Ala Gly Cys Cys Cys Ala Thr Ala Gly Thr Gly Ala Cys Ala
            805                 810                 815

Cys Cys Ala Cys Gly Thr Thr Thr Thr Thr Cys Cys Cys Thr Cys Thr
            820                 825                 830

Cys Cys Thr Gly Cys Thr Cys Thr Gly Ala Gly Ala Cys Thr Thr Thr
            835                 840                 845

Gly Ala Thr Gly Gly Gly Thr Gly Ala Ala Cys Thr Gly Gly Gly Cys
            850                 855                 860

Ala Ala Cys Ala Thr Thr Gly Cys Thr Ala Ala Ala Cys Cys Cys
865                 870                 875                 880

Gly Thr Gly Ala Thr Thr Thr Gly Cys Ala Cys Ala Thr Thr Cys Ala
            885                 890                 895

Gly Ala Gly Cys Cys Ala Thr Ala Thr Ala Ala Gly Thr Gly Ala Ala
            900                 905                 910

Ala Ala Thr Cys Gly Thr Gly Ala Thr Gly Ala Ala Gly Thr Thr Gly
            915                 920                 925

Ala Ala Gly Cys Thr Gly Thr Gly Ala Ala Ala Ala Cys Thr Thr
            930                 935                 940

Ala Thr Ala Cys Cys Cys Cys Ala Gly Thr Thr Ala Thr Ala Ala Ala
945                 950                 955                 960

Ala Ala Cys Thr Ala Cys Ala Cys Ala Thr Cys Thr Gly Thr Gly Thr
            965                 970                 975

-continued

```
Ala Thr Gly Ala Thr Ala Ala Ala Ala Ala Cys Ala Ala Thr Cys Thr
                980                 985                 990

Thr Thr Thr Gly Ala Cys Ala Ala Ala Thr Ala Ala Gly Ala Cys Ala
            995                1000                1005

Gly Thr Gly Ala Thr Gly Gly Cys Ala Cys Ala Cys Gly Gly Cys
        1010             1015             1020

Thr Gly Cys Thr Ala Cys Cys Thr Cys Thr Cys Thr Gly Cys Ala
    1025             1030             1035

Gly Ala Ala Gly Ala Ala Cys Thr Gly Ala Ala Cys Gly Thr Ala
    1040             1045             1050

Thr Thr Cys Cys Ala Thr Gly Ala Ala Cys Gly Ala Gly Gly Ala
    1055             1060             1065

Gly Cys Ala Thr Cys Cys Ala Thr Cys Gly Cys Ala Cys Ala Cys
    1070             1075             1080

Thr Gly Thr Cys Cys Ala Ala Thr Thr Cys Thr Ala Ala Thr
    1085             1090             1095

Thr Thr Ala Thr Cys Gly Cys Thr Cys Ala Gly Cys Ala Gly Thr
    1100             1105             1110

Gly Gly Ala Thr Thr Thr Cys Thr Ala Ala Ala Thr Gly Thr Gly
    1115             1120             1125

Cys Thr Ala Gly Ala Ala Gly Thr Cys Cys Thr Gly Ala Ala Ala
    1130             1135             1140

Cys Ala Thr Gly Ala Ala Gly Thr Cys Ala Ala Gly Ala Thr Ala
    1145             1150             1155

Gly Gly Gly Cys Thr Gly Gly Gly Thr Ala Cys Ala Gly Ala Cys
    1160             1165             1170

Gly Thr Gly Gly Cys Thr Gly Gly Thr Gly Gly Cys Thr Ala Thr
    1175             1180             1185

Thr Cys Ala Thr Ala Thr Thr Cys Cys Ala Thr Gly Cys Thr Thr
    1190             1195             1200

Gly Ala Thr Gly Cys Ala Ala Thr Cys Ala Gly Ala Ala Gly Ala
    1205             1210             1215

Gly Cys Ala Gly Thr Gly Ala Thr Gly Gly Thr Thr Cys Cys
    1220             1225             1230

Ala Ala Thr Ala Thr Cys Cys Thr Thr Thr Thr Ala Ala Thr Thr
    1235             1240             1245

Ala Ala Thr Ala Ala Gly Gly Thr Ala Ala Ala Thr Gly Ala Gly
    1250             1255             1260

Ala Ala Ala Ala Gly Cys Cys Thr Cys Ala Cys Cys Cys Thr Cys
    1265             1270             1275

Ala Ala Ala Gly Ala Ala Gly Thr Cys Thr Thr Cys Ala Gly Ala
    1280             1285             1290

Cys Thr Ala Gly Cys Thr Ala Cys Thr Cys Thr Thr Gly Gly Ala
    1295             1300             1305

Gly Gly Ala Ala Gly Cys Cys Ala Ala Gly Cys Cys Cys Thr Gly
    1310             1315             1320

Gly Gly Gly Cys Thr Gly Gly Ala Thr Gly Thr Gly Ala Gly
    1325             1330             1335

Ala Thr Thr Gly Gly Ala Ala Ala Cys Thr Thr Thr Gly Ala Ala
    1340             1345             1350

Gly Thr Gly Gly Gly Cys Ala Ala Gly Gly Ala Ala Thr Thr Thr
    1355             1360             1365

Gly Ala Thr Gly Cys Cys Ala Thr Cys Cys Thr Gly Ala Thr Cys
```

-continued

```
    1370                1375                1380

Ala Ala  Cys Cys Cys Cys Ala  Ala Ala Gly Cys Ala  Thr Cys Cys
    1385                1390                1395

Gly Ala  Cys Thr Cys Thr Cys  Cys Cys Ala Thr Thr  Gly Ala Cys
    1400                1405                1410

Cys Thr  Gly Thr Thr Thr Thr  Ala Thr Gly Gly Gly  Gly Ala Cys
    1415                1420                1425

Thr Thr  Thr Thr Thr Thr Gly  Gly Thr Gly Ala Thr  Ala Thr Thr
    1430                1435                1440

Thr Cys  Thr Gly Ala Gly Gly  Cys Thr Gly Thr Thr  Ala Thr Cys
    1445                1450                1455

Cys Ala  Gly Ala Ala Gly Thr  Thr Cys Cys Thr Cys  Thr Ala Thr
    1460                1465                1470

Cys Thr  Ala Gly Gly Ala Gly  Ala Thr Gly Ala Thr  Cys Gly Ala
    1475                1480                1485

Ala Ala  Thr Ala Thr Thr Gly  Ala Ala Gly Ala Gly  Gly Thr Thr
    1490                1495                1500

Thr Ala  Thr Gly Thr Gly Gly  Gly Cys Gly Gly Ala  Ala Ala Gly
    1505                1510                1515

Cys Ala  Gly Gly Thr Gly Gly  Thr Thr Cys Cys Gly  Thr Thr Thr
    1520                1525                1530

Thr Cys  Cys Ala Gly Cys Thr  Cys Ala Gly Thr Gly  Thr Ala Ala
    1535                1540                1545

Gly Ala  Cys Cys Cys Thr Cys  Gly Gly Gly Cys Gly  Thr Cys Thr
    1550                1555                1560

Ala Cys  Ala Ala Ala Gly Thr  Thr Cys Thr Cys Cys  Thr Gly Gly
    1565                1570                1575

Gly Ala  Thr Thr Ala Gly Cys  Gly Thr Gly Gly Thr  Thr Cys Thr
    1580                1585                1590

Gly Cys  Ala Thr Cys Thr Cys  Cys Cys Thr Thr Gly  Thr Gly Cys
    1595                1600                1605

Cys Cys  Ala Gly Gly Thr Gly  Gly Ala Gly Thr Thr  Ala Gly Ala
    1610                1615                1620

Ala Ala  Gly Thr Cys Ala Ala  Ala Ala Ala Ala Thr  Ala Gly Thr
    1625                1630                1635

Ala Cys  Cys Thr Thr Gly Thr  Thr Cys Thr Thr Gly  Gly Gly Ala
    1640                1645                1650

Thr Gly  Ala Cys Thr Ala Thr  Cys Cys Cys Thr Thr  Thr Cys Thr
    1655                1660                1665

Gly Thr  Gly Thr Cys Thr Ala  Gly Thr Thr Ala Cys  Ala Gly Thr
    1670                1675                1680

Ala Thr  Thr Cys Ala Cys Thr  Thr Gly Ala Cys Ala  Ala Ala Thr
    1685                1690                1695

Ala Gly  Thr Thr Cys Gly Ala  Ala Gly Gly Ala Ala  Gly Thr Thr
    1700                1705                1710

Gly Cys  Ala Cys Thr Ala Ala  Thr Thr Cys Thr Cys  Ala Ala Cys
    1715                1720                1725

Thr Cys  Thr Gly Gly Thr Thr  Gly Ala Gly Ala Gly  Gly Gly Thr
    1730                1735                1740

Thr Cys  Ala Thr Ala Ala Ala  Thr Thr Thr Cys Ala  Thr Gly Ala
    1745                1750                1755

Ala Ala  Ala Thr Ala Thr Cys  Thr Cys Cys Cys Thr  Thr Thr Gly
    1760                1765                1770
```

-continued

Gly Ala Gly Cys Thr Gly Cys Thr Cys Ala Gly Ala Cys Thr Thr
    1775            1780                1785

Ala Cys Thr Thr Thr Ala Ala Gly Cys Thr Cys Ala Ala Ala Cys
    1790            1795                1800

Ala Gly Ala Ala Gly Gly Gly Ala Ala Thr Gly Cys Thr Ala Thr
    1805            1810                1815

Thr Ala Cys Thr Gly Gly Thr Gly Gly Thr Gly Thr Thr Cys Cys
    1820            1825                1830

Thr Ala Cys Gly Gly Thr Ala Ala Gly Ala Cys Thr Ala Ala
    1835            1840                1845

Gly Cys Ala Ala Ala Gly Cys Cys Thr Thr Thr Thr Cys Ala
    1850            1855                1860

Thr Ala Thr Thr Thr Gly Ala Ala Ala Thr Gly Thr Gly Gly
    1865            1870                1875

Ala Ala Ala Gly Ala Ala Ala Ala Gly Ala Thr Gly Thr Thr Cys
    1880            1885                1890

Cys Thr Ala Ala Ala Ala Gly Gly Thr Thr Ala Gly Ala Thr Ala
    1895            1900                1905

Thr Thr Thr Thr Gly Ala Gly Cys Thr Ala Ala Thr Ala Ala Thr
    1910            1915                1920

Thr Gly Cys Ala Ala Ala Ala Thr Thr Ala Gly Ala Ala Gly
    1925            1930                1935

Ala Cys Thr Gly Ala Ala Ala Ala Thr Gly Gly Ala Cys Cys Cys
    1940            1945                1950

Ala Thr Gly Ala Gly Ala Gly Thr Ala Thr Ala Thr Thr Thr Thr
    1955            1960                1965

Thr Ala Thr Gly Ala Gly Gly Gly Ala Gly Cys Ala Ala Ala Ala
    1970            1975                1980

Gly Thr Thr Ala Gly Ala Cys Thr Gly Ala Gly Ala Ala Cys Ala
    1985            1990                1995

Ala Ala Cys Gly Thr Thr Ala Gly Ala Ala Ala Thr Cys Ala
    2000            2005                2010

Cys Thr Thr Cys Ala Gly Ala Thr Thr Gly Thr Gly Thr Thr Thr
    2015            2020                2025

Gly Ala Ala Ala Ala Thr Thr Ala Thr Ala Thr Ala Cys Thr Gly
    2030            2035                2040

Ala Gly Cys Ala Thr Ala Cys Thr Ala Ala Thr Thr Thr Ala Ala
    2045            2050                2055

Ala Ala Ala Gly Ala Gly Ala Ala Cys Thr Thr Gly Thr Thr Gly
    2060            2065                2070

Ala Ala Ala Thr Thr Thr Ala Ala Ala Ala Cys Gly Thr Gly Thr
    2075            2080                2085

Thr Thr Cys Thr Ala Gly Gly Thr Thr Gly Ala Cys Cys Thr Thr
    2090            2095                2100

Gly Thr Gly Thr Thr Thr Thr Ala Gly Ala Ala Ala Thr Thr Thr
    2105            2110                2115

Gly Cys Ala Cys Thr Thr Ala Ala Thr Gly Gly Ala Ala Thr Thr
    2120            2125                2130

Thr Gly Cys Ala Thr Thr Thr Cys Ala Gly Ala Gly Ala Thr Gly
    2135            2140                2145

Thr Gly Thr Thr Ala Gly Thr Gly Thr Thr Gly Thr Gly Cys Thr
    2150            2155                2160

-continued

```
Thr Thr Gly Cys Cys Thr Cys Thr Thr Gly Gly Cys Gly
    2165                2170                2175

Ala Thr Gly Ala Ala Thr Gly Thr Cys Ala Gly Ala Ala Ala Thr
    2180                2185                2190

Thr Gly Ala Ala Thr Gly Cys Cys Ala Cys Ala Thr Gly Cys Thr
    2195                2200                2205

Thr Thr Cys Ala Thr Ala Thr Ala Thr Ala Gly Thr Thr Thr
    2210                2215                2220

Thr Gly Thr Gly Cys Thr Thr Cys Ala Ala Gly Thr Gly Thr
    2225                2230                2235

Thr Thr Gly Ala Cys Ala Gly Ala Ala Gly Thr Thr Gly Gly Gly
    2240                2245                2250

Thr Ala Thr Thr Ala Ala Ala Gly Ala Thr Thr Ala Ala Ala
    2255                2260                2265

Gly Thr Cys Thr Cys Thr Thr Ala Gly Gly Ala Ala Thr Ala Thr
    2270                2275                2280

Thr Ala Thr Thr Cys Ala Thr Gly Thr Ala Ala Cys Thr Cys Cys
    2285                2290                2295

Ala Thr Gly Gly Cys Ala Thr Ala Ala Ala Thr Ala Gly Thr Thr
    2300                2305                2310

Gly Thr Ala Thr Thr Thr Thr Thr Gly Thr Gly Thr Ala Cys Thr
    2315                2320                2325

Thr Thr Ala Ala Ala Ala Thr Cys Ala Ala Cys Thr Thr Ala Thr
    2330                2335                2340

Ala Ala Cys Thr Gly Thr Gly Ala Gly Ala Thr Gly Thr Thr Ala
    2345                2350                2355

Thr Thr Gly Cys Thr Thr Cys Cys Ala Thr Thr Thr Ala Thr
    2360                2365                2370

Thr Ala Gly Ala Ala Gly Ala Gly Ala Ala Ala Cys Ala Ala Ala
    2375                2380                2385

Thr Thr Cys Cys Ala Thr Gly Cys Thr Thr Thr Ala Thr Gly Gly
    2390                2395                2400

Ala Ala Thr Thr Thr Ala Thr Gly Thr Ala Gly Ala Cys Thr Gly
    2405                2410                2415

Gly Ala Gly Thr Cys Thr Thr Cys Gly Thr Gly Ala Ala Cys Thr
    2420                2425                2430

Gly Gly Gly Gly Cys Ala Ala Ala Thr Gly Cys Thr Gly Gly Cys
    2435                2440                2445

Ala Thr Cys Cys Ala Gly Gly Ala Gly Cys Cys Gly Cys Cys Ala
    2450                2455                2460

Ala Thr Ala Cys Thr Ala Ala Cys Ala Gly Gly Ala Cys Ala Gly
    2465                2470                2475

Gly Thr Thr Cys Cys Ala Thr Gly Cys Cys Ala Thr Gly Gly
    2480                2485                2490

Cys Cys Thr Ala Thr Thr Cys Cys Ala Cys Cys Ala Ala Ala
    2495                2500                2505

Cys Ala Ala Thr Ala Thr Gly Thr Thr Gly Thr Ala Gly Thr Thr
    2510                2515                2520

Thr Cys Thr Gly Gly Ala Ala Ala Thr Thr Cys Cys Ala Thr Ala
    2525                2530                2535

Cys Thr Cys Ala Gly Ala Thr Ala Thr Cys Ala Gly Thr Cys Thr
    2540                2545                2550

Gly Cys Thr Ala Gly Ala Ala Cys Thr Thr Thr Ala Ala Ala Ala
```

-continued

```
              2555                2560                2565
Thr Gly Ala Ala Gly Gly Ala Cys Ala Ala Thr Cys Cys Thr
              2570                2575                2580
Gly Thr Thr Ala Ala Ala Gly Ala Ala Thr Ala Thr Thr Gly
              2585                2590                2595
Thr Thr Ala Ala Ala Ala Ala Thr Cys Thr Thr Ala Ala Ala
              2600                2605                2610
Cys Cys Cys Thr Gly Thr Gly Thr Ala Thr Thr Gly Ala Ala Ala
              2615                2620                2625
Gly Cys Ala Cys Thr Cys Thr Ala Thr Thr Thr Cys Thr Ala
              2630                2635                2640
Ala Thr Thr Thr Thr Ala Thr Cys Cys Ala Gly Thr Thr Thr Thr
              2645                2650                2655
Cys Thr Gly Thr Thr Thr Ala Ala Cys Thr Cys Cys Thr Thr Ala
              2660                2665                2670
Thr Ala Ala Thr Gly Thr Thr Thr Ala Gly Gly Ala Thr Ala Thr
              2675                2680                2685
Thr Ala Ala Ala Ala Thr Thr Thr Thr Ala Gly Gly Ala Thr Ala
              2690                2695                2700
Ala Thr Gly Ala Ala Gly Ala Gly Thr Ala Cys Ala Thr Ala Ala
              2705                2710                2715
Thr Gly Thr Cys Cys Thr Ala Cys Thr Ala Ala Thr Ala Thr
              2720                2725                2730
Thr Thr Ala Thr Gly Thr Thr Ala Ala Thr Ala Gly Gly Ala Cys
              2735                2740                2745
Thr Thr Ala Ala Thr Thr Cys Thr Thr Ala Cys Thr Ala Gly Ala
              2750                2755                2760
Cys Ala Thr Cys Thr Ala Gly Gly Ala Ala Cys Ala Thr Thr Ala
              2765                2770                2775
Cys Ala Ala Ala Gly Cys Ala Ala Ala Gly Ala Cys Thr Ala Thr
              2780                2785                2790
Thr Thr Thr Thr Ala Thr Gly Cys Thr Thr Cys Cys Ala Thr Ala
              2795                2800                2805
Ala Cys Cys Thr Ala Gly Ala Ala Thr Thr Ala Ala Ala Ala Cys
              2810                2815                2820
Cys Ala Ala Ala Thr Thr Ala Thr Gly Ala Cys Cys Thr Thr Ala
              2825                2830                2835
Thr Gly Ala Thr Ala Ala Ala Thr Cys Thr Thr Ala Ala Gly
              2840                2845                2850
Thr Ala Thr Thr Gly Gly Thr Gly Thr Gly Ala Ala Thr Gly Thr
              2855                2860                2865
Thr Ala Thr Thr Ala Ala Ala Thr Thr Cys Thr Ala Thr Ala
              2870                2875                2880
Thr Thr Thr Thr Thr Cys Thr Thr Ala Thr Thr Thr Ala Ala Thr
              2885                2890                2895
Thr Ala Cys Ala Ala Ala Thr Ala Cys Thr Ala Thr Ala Ala Ala
              2900                2905                2910
Thr Gly Ala Gly Cys Ala Ala Gly Gly Ala Ala Ala Gly Gly
              2915                2920                2925
Ala Ala Thr Ala Gly Ala Cys Thr Thr Cys Thr Thr Ala Ala
              2930                2935                2940
Thr Ala Thr Ala Thr Thr Ala Thr Ala Ala Cys Ala Cys Thr Cys
              2945                2950                2955
```

-continued

```
Ala Thr Thr Cys Cys Thr Ala Gly Ala Gly Cys Thr Thr Ala Gly
2960                2965                2970

Gly Gly Gly Thr Gly Ala Cys Thr Cys Thr Thr Ala Ala Thr
2975                2980                2985

Ala Thr Thr Ala Cys Cys Thr Thr Ala Thr Ala Gly Thr Ala Gly
2990                2995                3000

Ala Ala Ala Cys Thr Thr Thr Ala Thr Gly Thr Ala Ala Thr Ala
3005                3010                3015

Thr Ala Gly Cys Thr Ala Ala Cys Thr Cys Cys Gly Thr Ala Thr
3020                3025                3030

Thr Thr Ala Cys Ala Gly Ala Ala Cys Ala Ala Ala Ala Ala Ala
3035                3040                3045

Ala Cys Ala Cys Ala Gly Thr Thr Cys Cys Cys Cys Cys Thr Cys
3050                3055                3060

Cys Thr Gly Thr Ala Gly Thr Ala Thr Ala Ala Ala Thr Thr Thr
3065                3070                3075

Thr Ala Thr Thr Thr Thr Cys Ala Cys Ala Thr Ala Cys Thr Thr
3080                3085                3090

Ala Gly Cys Thr Ala Ala Thr Thr Thr Ala Gly Cys Ala Gly Thr
3095                3100                3105

Ala Ala Thr Thr Gly Gly Cys Cys Cys Ala Gly Thr Thr Thr Thr
3110                3115                3120

Thr Thr Cys Cys Cys Thr Ala Ala Thr Ala Gly Ala Ala Ala Thr
3125                3130                3135

Ala Cys Thr Thr Thr Thr Ala Gly Ala Thr Thr Gly Ala Thr Thr
3140                3145                3150

Thr Ala Thr Gly Thr Ala Thr Ala Cys Ala Thr Gly Ala Cys Ala
3155                3160                3165

Cys Cys Thr Ala Ala Ala Gly Ala Gly Gly Gly Ala Ala Cys Ala
3170                3175                3180

Ala Ala Ala Gly Thr Thr Ala Gly Thr Thr Thr Thr Ala Thr Thr
3185                3190                3195

Thr Thr Thr Thr Thr Ala Ala Thr Ala Ala Ala Cys Ala Ala Cys
3200                3205                3210

Ala Gly Ala Gly Thr Thr Thr Gly Thr Thr Thr Thr Gly Thr Gly
3215                3220                3225

Ala Gly Ala Thr Ala Ala Gly Thr Ala Thr Cys Thr Thr Ala Gly
3230                3235                3240

Thr Ala Ala Ala Cys Cys Cys Ala Ala Thr Thr Thr Cys Cys Ala
3245                3250                3255

Gly Thr Cys Thr Thr Ala Gly Thr Cys Thr Gly Thr Ala Thr Thr
3260                3265                3270

Thr Cys Cys Ala Ala Thr Ala Thr Thr Thr Cys Thr Ala Ala Thr
3275                3280                3285

Thr Cys Cys Thr Gly Ala Gly Cys Cys Ala Cys Gly Thr Cys Ala
3290                3295                3300

Ala Ala Gly Ala Thr Gly Cys Cys Thr Thr Gly Cys Cys Ala Ala
3305                3310                3315

Ala Thr Thr Thr Cys Thr Cys Cys Cys Cys Ala Thr Thr Thr Cys
3320                3325                3330

Thr Cys Thr Ala Cys Gly Gly Gly Gly Cys Thr Ala Gly Cys Ala
3335                3340                3345
```

-continued

```
Ala Ala  Ala Ala Thr Cys Thr  Thr Cys Ala Gly Cys  Thr Thr Thr
    3350                 3355                 3360

Ala Thr  Cys Cys Cys Thr Cys  Ala Ala Cys Cys Cys  Cys Thr Gly
    3365                 3370                 3375

Cys Cys  Ala Ala Ala Gly Gly  Ala Ala Cys Thr Thr  Gly Ala Thr
    3380                 3385                 3390

Thr Ala  Cys Ala Thr Gly Gly  Thr Gly Thr Cys Thr  Ala Ala Cys
    3395                 3400                 3405

Cys Ala  Ala Ala Thr Gly Ala  Gly Cys Ala Gly Gly  Cys Thr Thr
    3410                 3415                 3420

Ala Gly  Gly Ala Ala Thr Thr  Thr Ala Gly Ala Thr  Gly Ala Gly
    3425                 3430                 3435

Ala Thr  Gly Thr Gly Thr Ala  Ala Gly Ala Thr Thr  Cys Ala Cys
    3440                 3445                 3450

Thr Thr  Ala Cys Ala Gly Gly  Cys Ala Gly Thr Ala  Gly Cys Thr
    3455                 3460                 3465

Gly Cys  Thr Thr Cys Thr Ala  Gly Cys Ala Thr Thr  Thr Gly Cys
    3470                 3475                 3480

Ala Ala  Gly Ala Thr Cys Cys  Thr Ala Cys Ala Cys  Thr Thr Thr
    3485                 3490                 3495

Thr Ala  Cys Cys Thr Thr Cys  Thr Thr Thr Ala Ala  Gly Gly Gly
    3500                 3505                 3510

Thr Gly  Thr Ala Cys Ala Thr  Thr Thr Thr Gly Ala  Thr Gly Thr
    3515                 3520                 3525

Thr Gly  Ala Ala Cys Ala Thr  Cys Ala Gly Thr Thr  Thr Thr Cys
    3530                 3535                 3540

Ala Thr  Gly Thr Ala Gly Ala  Cys Thr Thr Ala Gly  Gly Ala Cys
    3545                 3550                 3555

Thr Cys  Ala Thr Gly Thr Gly  Cys Ala Gly Thr Ala  Ala Ala Thr
    3560                 3565                 3570

Ala Thr  Ala Ala Ala Thr Ala  Ala Gly Thr Gly Thr  Ala Gly Cys
    3575                 3580                 3585

Ala Thr  Cys Ala Gly Ala Ala  Gly Cys Ala Gly Thr  Ala Gly Gly
    3590                 3595                 3600

Ala Ala  Thr Gly Gly Cys Cys  Gly Thr Ala Thr Ala  Cys Ala Ala
    3605                 3610                 3615

Cys Cys  Ala Thr Cys Cys Thr  Gly Thr Thr Ala Ala  Ala Cys Ala
    3620                 3625                 3630

Thr Thr  Thr Ala Ala Ala Thr  Thr Thr Ala Gly Cys  Thr Cys Thr
    3635                 3640                 3645

Gly Ala  Thr Ala Gly Thr Gly  Thr Gly Thr Thr Ala  Ala Gly Ala
    3650                 3655                 3660

Cys Cys  Thr Gly Ala Ala Thr  Ala Thr Cys Thr Thr  Thr Cys Cys
    3665                 3670                 3675

Thr Ala  Gly Thr Ala Ala Ala  Ala Ala Thr Ala Gly  Gly Ala Thr
    3680                 3685                 3690

Gly Thr  Gly Thr Thr Gly Ala  Ala Ala Thr Ala Thr  Thr Thr Ala
    3695                 3700                 3705

Thr Ala  Thr Gly Thr Ala Cys  Thr Thr Thr Gly Ala  Thr Cys Thr
    3710                 3715                 3720

Cys Thr  Cys Cys Ala Cys Ala  Thr Cys Ala Cys Thr  Thr Ala Thr
    3725                 3730                 3735

Ala Ala  Cys Thr Thr Ala Thr  Gly Thr Gly Thr Thr  Thr Thr Ala
```

-continued

```
                    3740                3745                3750
Thr Thr  Thr Cys Thr Cys Cys  Ala Ala Gly Thr Gly  Cys Gly Gly
    3755              3760                3765

Thr Gly  Thr Thr Cys Cys Thr  Gly Ala Ala Thr Gly  Thr Thr Ala
    3770              3775                3780

Thr Gly  Thr Ala Thr Gly Cys  Thr Thr Thr Thr Thr  Thr Thr Thr
    3785              3790                3795

Cys Thr  Gly Thr Ala Cys Cys  Ala Cys Ala Gly Gly  Cys Ala Thr
    3800              3805                3810

Thr Ala  Thr Cys Thr Ala Thr  Ala Cys Cys Thr Gly  Gly Gly Gly
    3815              3820                3825

Cys Cys  Ala Gly Ala Thr Thr  Thr Thr Cys Thr Gly  Cys Ala Cys
    3830              3835                3840

Thr Thr  Thr Gly Ala Ala Ala  Thr Gly Thr Thr Gly  Cys Cys Thr
    3845              3850                3855

Thr Thr  Gly Cys Cys Thr Ala  Ala Thr Gly Thr Ala  Gly Gly Thr
    3860              3865                3870

Thr Gly  Ala Cys Thr Thr Thr  Cys Thr Gly Ala Ala  Thr Thr Gly
    3875              3880                3885

Thr Gly  Gly Ala Gly Ala Gly  Gly Cys Ala Cys Thr  Thr Thr Thr
    3890              3895                3900

Cys Cys  Ala Ala Gly Cys Cys  Ala Ala Thr Cys Thr  Thr Ala Thr
    3905              3910                3915

Thr Thr  Gly Thr Cys Ala Cys  Thr Thr Thr Thr Thr  Gly Thr Thr
    3920              3925                3930

Thr Thr  Ala Ala Thr Ala Thr  Cys Thr Gly Cys Thr  Thr Cys Thr
    3935              3940                3945

Cys Thr  Gly Ala Cys Ala Gly  Gly Ala Ala Ala Gly  Ala Ala Ala
    3950              3955                3960

Cys Ala  Ala Thr Thr Cys Ala  Cys Thr Thr Ala Cys  Cys Ala Gly
    3965              3970                3975

Cys Cys  Thr Cys Cys Thr Cys  Ala Cys Cys Cys Ala  Thr Cys
    3980              3985                3990

Cys Thr  Cys Cys Ala Cys Cys  Ala Thr Thr Thr Cys  Cys Thr Thr
    3995              4000                4005

Ala Ala  Thr Gly Thr Thr Cys  Cys Ala Thr Gly Gly  Thr Ala Thr
    4010              4015                4020

Thr Thr  Thr Cys Ala Ala Cys  Gly Gly Ala Ala Thr  Ala Cys Ala
    4025              4030                4035

Cys Thr  Thr Thr Gly Ala Ala  Ala Gly Gly Thr Ala  Ala Ala Ala
    4040              4045                4050

Ala Cys  Ala Ala Thr Thr Cys  Ala Ala Ala Ala Gly  Thr Ala Thr
    4055              4060                4065

Cys Gly  Ala Thr Thr Ala Thr  Cys Ala Thr Ala Ala  Ala Thr Thr
    4070              4075                4080

Cys Ala  Cys Ala Ala Ala Ala  Thr Ala Thr Thr Thr  Thr Thr Gly
    4085              4090                4095

Cys Ala  Ala Cys Cys Ala Gly  Ala Ala Cys Ala Cys  Ala Ala Ala
    4100              4105                4110

Ala Gly  Cys Ala Gly Gly Cys  Thr Ala Gly Thr Cys  Ala Gly Cys
    4115              4120                4125

Thr Ala  Ala Gly Gly Thr Ala  Ala Ala Thr Thr Thr  Cys Ala Thr
    4130              4135                4140
```

-continued

```
Thr Thr Thr Cys Ala Ala Cys Gly Ala Gly Ala Gly Gly Gly
    4145            4150            4155

Ala Ala Ala Cys Ala Thr Gly Gly Gly Ala Ala Gly Thr Ala Ala
    4160            4165            4170

Ala Ala Gly Ala Thr Thr Ala Gly Gly Ala Thr Gly Thr Gly Ala
    4175            4180            4185

Ala Ala Gly Gly Thr Thr Gly Thr Cys Cys Thr Ala Ala Ala Cys
    4190            4195            4200

Ala Gly Ala Cys Cys Ala Ala Gly Gly Ala Gly Ala Cys Thr Gly
    4205            4210            4215

Thr Thr Cys Cys Cys Thr Ala Ala Thr Thr Ala Thr Thr Cys
    4220            4225            4230

Thr Cys Thr Thr Gly Gly Cys Thr Gly Gly Thr Thr Cys Thr Cys
    4235            4240            4245

Thr Cys Ala Thr Thr Gly Ala Ala Thr Thr Ala Thr Cys Ala Gly
    4250            4255            4260

Ala Cys Cys Cys Cys Ala Ala Gly Ala Gly Gly Ala Gly Ala Thr
    4265            4270            4275

Ala Thr Thr Gly Gly Ala Ala Cys Ala Gly Gly Cys Thr Cys Cys
    4280            4285            4290

Cys Thr Thr Cys Ala Thr Gly Cys Cys Ala Ala Gly Gly Gly Thr
    4295            4300            4305

Cys Thr Thr Cys Thr Ala Ala Gly Thr Thr Ala Ala Thr Ala
    4310            4315            4320

Cys Thr Gly Thr Gly Ala Gly Cys Ala Thr Thr Gly Ala Gly Cys
    4325            4330            4335

Cys Cys Cys Cys Ala Thr Thr Ala Ala Ala Ala Cys Thr Cys Thr
    4340            4345            4350

Thr Thr Thr Thr Thr Ala Cys Thr Thr Cys Ala Gly Ala Ala Ala
    4355            4360            4365

Gly Ala Ala Thr Thr Thr Thr Ala Cys Ala Gly Gly Thr Thr Ala
    4370            4375            4380

Ala Ala Gly Gly Gly Ala Ala Ala Gly Ala Ala Ala Thr Gly Gly
    4385            4390            4395

Thr Gly Gly Gly Ala Ala Ala Cys Thr Cys Thr Cys Cys Cys Cys
    4400            4405            4410

Gly Thr Ala Ala Thr Gly Cys Thr Thr Ala Gly Cys Cys Ala Ala
    4415            4420            4425

Cys Thr Thr Ala Ala Ala Gly Thr Gly Thr Ala Cys Cys Cys
    4430            4435            4440

Thr Thr Cys Ala Ala Thr Ala Thr Cys Cys Cys Cys Ala Thr Thr
    4445            4450            4455

Gly Gly Cys Ala Ala Cys Thr Gly Cys Ala Gly Cys Thr Gly Ala
    4460            4465            4470

Gly Ala Thr Cys Thr Thr Ala Gly Ala Gly Ala Gly Gly Ala Ala
    4475            4480            4485

Ala Thr Ala Thr Ala Ala Cys Cys Gly Gly Thr Gly Thr Gly Ala
    4490            4495            4500

Gly Ala Thr Cys Thr Ala Gly Cys Ala Ala Thr Gly Cys Ala Thr
    4505            4510            4515

Thr Thr Thr Gly Ala Ala Thr Cys Thr Thr Cys Ala Cys Thr Cys
    4520            4525            4530
```

-continued

Cys Cys Thr Ala Cys Cys Ala Gly Gly Cys Thr Cys Thr Thr Cys
4535 4540 4545

Cys Thr Ala Thr Thr Thr Thr Thr Ala Ala Thr Cys Thr Cys Thr
4550 4555 4560

Thr Cys Ala Cys Cys Thr Cys Ala Gly Ala Ala Cys Thr Ala Gly
4565 4570 4575

Ala Cys Ala Thr Ala Thr Gly Gly Ala Gly Ala Gly Cys Thr Thr
4580 4585 4590

Thr Ala Ala Ala Gly Gly Cys Ala Ala Gly Cys Thr Gly Gly Ala
4595 4600 4605

Ala Gly Gly Cys Ala Cys Ala Thr Thr Gly Thr Ala Thr Cys Ala
4610 4615 4620

Ala Thr Thr Cys Thr Ala Cys Cys Thr Thr Gly Thr Gly Cys Thr
4625 4630 4635

Ala Thr Ala Cys Gly Thr Ala Gly Gly Ala Gly Ala Gly Ala Thr
4640 4645 4650

Cys Cys Ala Ala Ala Ala Thr Thr Thr Gly Gly Ala Thr Gly Cys
4655 4660 4665

Thr Thr Cys Thr Gly Gly Ala Gly Ala Cys Thr Cys Thr Thr Ala
4670 4675 4680

Gly Ala Cys Ala Thr Cys Thr Thr Thr Thr Cys Ala Thr Thr Gly
4685 4690 4695

Thr Thr Gly Thr Cys Cys Ala Thr Thr Thr Thr Thr Ala Ala Ala
4700 4705 4710

Gly Thr Thr Gly Ala Thr Gly Ala Thr Thr Gly Cys Thr Gly Gly
4715 4720 4725

Ala Ala Ala Cys Ala Thr Thr Cys Ala Cys Ala Cys Gly Cys Thr
4730 4735 4740

Thr Ala Ala Ala Ala Gly Cys Ala Ala Thr Gly Gly Thr Gly Thr
4745 4750 4755

Gly Ala Gly Thr Thr Ala Thr Thr Ala Ala Thr Gly Gly Gly Thr
4760 4765 4770

Ala Ala Ala Cys Thr Ala Ala Gly Ala Ala Gly Thr Gly Thr Thr
4775 4780 4785

Ala Thr Ala Gly Gly Cys Ala Ala Thr Gly Ala Cys Thr Thr Gly
4790 4795 4800

Ala Ala Ala Thr Gly Gly Thr Thr Thr Thr Thr Ala Ala Ala Thr
4805 4810 4815

Thr Gly Thr Ala Thr Gly Gly Ala Thr Thr Gly Thr Thr Ala Ala
4820 4825 4830

Gly Ala Ala Thr Thr Gly Thr Thr Gly Ala Ala Ala Ala Ala Ala
4835 4840 4845

Ala Ala Thr Thr Thr Thr Thr Thr Thr Thr Thr Thr Thr Thr Gly
4850 4855 4860

Gly Ala Cys Ala Gly Cys Thr Thr Cys Ala Ala Gly Gly Ala Gly
4865 4870 4875

Ala Thr Gly Thr Thr Ala Gly Cys Ala Ala Thr Thr Thr Cys Ala
4880 4885 4890

Gly Ala Thr Ala Thr Ala Cys Thr Ala Gly Cys Cys Ala Gly Thr
4895 4900 4905

Thr Thr Ala Gly Gly Thr Ala Thr Gly Ala Cys Thr Thr Thr Gly
4910 4915 4920

Gly Ala Ala Gly Thr Gly Cys Ala Gly Ala Ala Ala Cys Ala Gly

-continued

```
            4925                4930                4935

Ala Ala Gly Gly Ala Thr Ala Cys Thr Gly Thr Ala Gly Ala
        4940                4945                4950

Ala Ala Ala Thr Cys Cys Thr Ala Ala Cys Ala Thr Thr Gly Gly
        4955                4960                4965

Thr Cys Thr Cys Cys Gly Thr Gly Cys Ala Thr Thr Gly Thr
        4970                4975                4980

Thr Cys Ala Cys Ala Cys Cys Thr Gly Gly Thr Cys Thr Cys Ala
        4985                4990                4995

Cys Thr Gly Cys Cys Thr Thr Thr Cys Cys Thr Cys Cys Cys
        5000                5005                5010

Ala Cys Ala Gly Ala Cys Cys Thr Gly Ala Gly Thr Gly Thr Gly
        5015                5020                5025

Ala Ala Ala Gly Ala Cys Thr Gly Ala Gly Ala Gly Thr Thr Gly
        5030                5035                5040

Ala Gly Gly Ala Gly Thr Thr Ala Cys Thr Thr Thr Gly Thr Gly
        5045                5050                5055

Gly Ala Thr Cys Thr Thr Gly Thr Cys Cys Ala Ala Ala Thr Thr
        5060                5065                5070

Thr Ala Gly Thr Gly Ala Ala Ala Thr Gly Thr Gly Gly Ala Ala
        5075                5080                5085

Gly Thr Cys Ala Ala Cys Cys Ala Gly Ala Cys Cys Ala Ala Thr
        5090                5095                5100

Gly Ala Thr Gly Gly Ala Ala Thr Thr Ala Ala Ala Thr Gly Thr
        5105                5110                5115

Ala Ala Ala Thr Thr Cys Cys Ala Ala Gly Ala Gly Gly Gly Cys
        5120                5125                5130

Thr Thr Thr Cys Ala Cys Ala Gly Thr Cys Cys Ala Cys Ala Gly
        5135                5140                5145

Gly Gly Thr Thr Cys Ala Ala Ala Thr Gly Ala Cys Thr Thr Gly
        5150                5155                5160

Gly Gly Thr Ala Ala Cys Ala Gly Ala Ala Gly Thr Thr Ala Thr
        5165                5170                5175

Thr Cys Thr Thr Ala Gly Cys Thr Thr Ala Cys Cys Thr Gly Thr
        5180                5185                5190

Thr Ala Thr Gly Thr Gly Ala Cys Ala Gly Thr Gly Ala Thr Thr
        5195                5200                5205

Thr Ala Cys Cys Thr Gly Thr Cys Cys Ala Thr Thr Cys Cys
        5210                5215                5220

Ala Ala Cys Cys Cys Ala Ala Ala Ala Gly Cys Cys Thr Gly Thr
        5225                5230                5235

Cys Ala Gly Ala Ala Ala Gly Cys Ala Thr Thr Cys Thr Thr Thr
        5240                5245                5250

Ala Gly Ala Gly Ala Ala Ala Cys Cys Ala Cys Thr Thr Thr
        5255                5260                5265

Ala Cys Ala Thr Thr Thr Gly Thr Thr Gly Thr Thr Ala Ala Ala
        5270                5275                5280

Cys Thr Cys Cys Thr Gly Ala Thr Cys Gly Cys Thr Ala Cys Thr
        5285                5290                5295

Cys Thr Thr Ala Ala Gly Ala Ala Thr Ala Thr Ala Cys Ala Thr
        5300                5305                5310

Gly Thr Ala Thr Gly Thr Ala Thr Thr Cys Ala Thr Ala Gly Gly
        5315                5320                5325
```

```
Ala Ala Cys Ala Thr Thr Thr  Thr Thr Thr Cys Thr  Cys Ala Ala
    5330             5335              5340

Thr Ala Thr Thr Thr Gly Thr  Ala Thr Gly Ala Thr  Thr Cys Gly
    5345             5350              5355

Cys Thr Thr Ala Cys Thr Gly  Thr Thr Ala Thr Thr  Gly Thr Gly
    5360             5365              5370

Cys Thr Gly Ala Gly Thr Gly  Ala Gly Cys Thr Cys  Cys Thr Gly
    5375             5380              5385

Thr Gly Thr Gly Cys Thr Thr  Cys Ala Gly Ala Cys  Ala Ala Ala
    5390             5395              5400

Ala Ala Thr Ala Ala Ala Thr  Gly Ala Gly Ala Cys  Thr Thr Thr
    5405             5410              5415

Gly Thr Gly Thr Thr Thr Ala  Cys Gly Thr Thr Ala  Ala Ala Ala
    5420             5425              5430

Ala Ala Ala Ala Ala Ala Ala  Ala Ala Ala Ala Ala  Ala Ala Ala
    5435             5440              5445

Ala Ala Ala
    5450

<210> SEQ ID NO 3
<211> LENGTH: 454
<212> TYPE: PRT
<213> ORGANISM: Pongo pygmaeus

<400> SEQUENCE: 3

Met Cys Ala Ala Gln Met Pro Leu Ala His Ile Phe Arg Gly Thr
1               5                   10                  15

Phe Val His Ser Thr Trp Thr Cys Pro Met Glu Val Leu Arg Asp His
                20                  25                  30

Leu Leu Gly Val Ser Asp Ser Gly Lys Ile Val Phe Leu Glu Glu Ala
            35                  40                  45

Ser Gln Gln Glu Lys Leu Ala Lys Glu Trp Cys Phe Lys Pro Cys Glu
    50                  55                  60

Ile Arg Glu Leu Ser His His Glu Phe Phe Met Pro Gly Leu Val Asp
65                  70                  75                  80

Thr His Ile His Ala Ser Gln Tyr Ser Phe Ala Gly Ser Asn Ile Asp
                85                  90                  95

Leu Pro Leu Leu Glu Trp Leu Thr Lys Tyr Thr Phe Pro Ala Glu His
            100                 105                 110

Arg Phe Gln Asn Thr Asp Phe Ala Glu Glu Val Tyr Thr Arg Val Val
        115                 120                 125

Arg Arg Thr Leu Lys Asn Gly Thr Thr Thr Ala Cys Tyr Phe Ala Thr
    130                 135                 140

Ile His Thr Asp Ser Ser Leu Leu Leu Ala Asp Ile Thr Asp Lys Phe
145                 150                 155                 160

Gly Gln Arg Ala Phe Val Gly Lys Val Cys Met Asn Leu Asn Asp Thr
                165                 170                 175

Phe Pro Glu Tyr Asn Glu Thr Thr Glu Glu Ser Ile Lys Glu Thr Glu
            180                 185                 190

Arg Phe Val Ser Glu Met Leu Gln Arg Lys Tyr Ser Arg Val Lys Pro
        195                 200                 205

Ile Val Thr Pro Arg Phe Ser Leu Ser Cys Ser Glu Thr Leu Met Gly
    210                 215                 220

Asp Leu Gly Asn Ile Ala Lys Thr His Asp Leu His Ile Gln Ser His
```

-continued

```
                225                 230                 235                 240
Ile Ser Glu Asn Arg Asp Glu Val Glu Ala Val Lys Asn Leu Tyr Pro
                245                 250                 255

Ser Tyr Lys Asn Tyr Thr Asp Val Tyr Asp Lys Asn Leu Leu Thr
            260                 265                 270

Asn Lys Thr Val Met Ala His Gly Cys Tyr Leu Ser Ala Glu Glu Leu
            275                 280                 285

Asn Val Phe His Glu Arg Gly Ala Ser Ile Ala His Cys Pro Asn Ser
        290                 295                 300

Asn Leu Ser Leu Ser Ser Gly Phe Leu Asn Val Leu Glu Val Leu Lys
305                 310                 315                 320

His Glu Val Lys Ile Gly Leu Gly Thr Asp Val Ala Gly Gly Tyr Ser
                325                 330                 335

Tyr Ser Met Leu Asp Ala Ile Arg Arg Ala Val Met Val Ser Asn Ile
                340                 345                 350

Leu Leu Ile Asn Lys Val Asn Glu Lys Ser Leu Thr Leu Lys Glu Val
            355                 360                 365

Phe Arg Leu Ala Thr Leu Gly Gly Ser Gln Ala Leu Gly Leu Asp Gly
        370                 375                 380

Glu Ile Gly Asn Phe Glu Val Gly Lys Glu Phe Asp Ala Ile Leu Ile
385                 390                 395                 400

Asn Pro Lys Ala Ser Asp Ser Pro Ile Asp Leu Phe Tyr Gly Asp Phe
                405                 410                 415

Phe Gly Asp Ile Ser Glu Ala Val Ile Gln Lys Phe Leu Tyr Leu Gly
            420                 425                 430

Asp Asp Arg Asn Ile Glu Glu Val Tyr Val Gly Gly Lys Gln Val Val
        435                 440                 445

Pro Phe Ser Ser Ser Val
450

<210> SEQ ID NO 4
<211> LENGTH: 5354
<212> TYPE: PRT
<213> ORGANISM: Pongo pygmaeus

<400> SEQUENCE: 4

Gly Ala Gly Gly Ala Thr Ala Gly Gly Cys Cys Gly Gly Ala Gly
1               5                   10                  15

Cys Cys Gly Gly Thr Gly Thr Cys Cys Gly Cys Cys Gly Ala Cys
            20                  25                  30

Ala Gly Cys Cys Gly Cys Cys Gly Cys Ala Gly Cys Thr Gly Cys
        35                  40                  45

Ala Gly Ala Gly Ala Gly Thr Cys Cys Gly Cys Thr Gly Cys Gly
    50                  55                  60

Cys Thr Thr Cys Cys Gly Cys Cys Gly Cys Thr Gly Cys Gly Cys
65                  70                  75                  80

Cys Cys Thr Cys Cys Thr Cys Gly Ala Cys Cys Ala Gly Cys Ala Gly
                85                  90                  95

Ala Cys Cys Cys Gly Cys Gly Cys Thr Gly Cys Gly Cys Thr Cys Cys
            100                 105                 110

Gly Cys Cys Gly Cys Thr Gly Ala Cys Ala Thr Gly Thr Gly Thr
        115                 120                 125

Cys Cys Gly Cys Thr Cys Ala Gly Ala Thr Gly Cys Cys Gly Cys Cys
    130                 135                 140
```

-continued

```
Cys Cys Thr Gly Gly Cys Gly Cys Ala Cys Ala Thr Cys Thr Thr Cys
145                 150                 155                 160

Cys Gly Ala Gly Gly Gly Ala Cys Gly Thr Thr Cys Gly Thr Cys Cys
                165                 170                 175

Ala Cys Thr Cys Cys Ala Cys Cys Thr Gly Gly Ala Cys Cys Thr Gly
            180                 185                 190

Cys Cys Cys Cys Ala Thr Gly Gly Ala Gly Gly Thr Gly Cys Thr Gly
        195                 200                 205

Cys Gly Gly Gly Ala Thr Cys Ala Cys Cys Thr Cys Cys Thr Cys Gly
    210                 215                 220

Gly Cys Gly Thr Gly Ala Gly Cys Gly Ala Cys Ala Gly Cys Gly Gly
225                 230                 235                 240

Cys Ala Ala Ala Ala Thr Ala Gly Thr Gly Thr Thr Thr Thr Thr Ala
                245                 250                 255

Gly Ala Ala Gly Ala Ala Gly Cys Ala Thr Cys Thr Cys Ala Ala Cys
            260                 265                 270

Ala Ala Gly Ala Ala Ala Ala Ala Cys Thr Gly Gly Cys Cys Ala Ala
        275                 280                 285

Ala Gly Ala Ala Thr Gly Gly Thr Gly Cys Thr Thr Cys Ala Ala Gly
    290                 295                 300

Cys Cys Ala Thr Gly Thr Gly Ala Ala Ala Thr Ala Ala Gly Ala Gly
305                 310                 315                 320

Ala Ala Cys Thr Gly Ala Gly Cys Cys Ala Cys Cys Ala Thr Gly Ala
                325                 330                 335

Gly Thr Thr Cys Thr Thr Cys Ala Thr Gly Cys Cys Thr Gly Gly Gly
            340                 345                 350

Cys Thr Gly Gly Thr Thr Gly Ala Thr Ala Cys Ala Cys Ala Cys Ala
        355                 360                 365

Thr Cys Cys Ala Thr Gly Cys Cys Thr Cys Thr Cys Ala Gly Thr Ala
    370                 375                 380

Thr Thr Cys Cys Thr Thr Thr Gly Cys Thr Gly Gly Ala Ala Gly Thr
385                 390                 395                 400

Ala Ala Cys Ala Thr Ala Gly Ala Cys Cys Thr Gly Cys Cys Ala Cys
                405                 410                 415

Thr Cys Thr Thr Gly Gly Ala Gly Thr Gly Gly Cys Thr Gly Ala Cys
            420                 425                 430

Cys Ala Ala Gly Thr Ala Cys Ala Cys Ala Thr Thr Thr Cys Cys Thr
        435                 440                 445

Gly Cys Ala Gly Ala Ala Cys Ala Cys Ala Gly Ala Thr Thr Cys Cys
    450                 455                 460

Ala Gly Ala Ala Cys Ala Cys Thr Gly Ala Cys Thr Thr Thr Gly Cys
465                 470                 475                 480

Gly Gly Ala Ala Gly Ala Ala Gly Thr Ala Thr Ala Thr Ala Cys Cys
                485                 490                 495

Ala Gly Ala Gly Thr Thr Gly Thr Cys Ala Gly Gly Ala Gly Ala Ala
            500                 505                 510

Cys Ala Cys Thr Ala Ala Ala Gly Ala Ala Thr Gly Gly Ala Ala Cys
        515                 520                 525

Ala Ala Cys Cys Ala Cys Ala Gly Cys Thr Thr Gly Thr Thr Ala Cys
    530                 535                 540

Thr Thr Thr Gly Cys Ala Ala Cys Ala Ala Thr Thr Cys Ala Cys Ala
545                 550                 555                 560

Cys Thr Gly Ala Cys Thr Cys Ala Thr Cys Thr Cys Thr Gly Cys Thr
```

-continued

```
                565                 570                 575
Cys Cys Thr Thr Gly Cys Cys Gly Ala Cys Ala Thr Ala Cys Ala
                580                 585                 590
Gly Ala Thr Ala Ala Ala Thr Thr Thr Gly Gly Ala Cys Ala Gly Cys
            595                 600                 605
Gly Gly Gly Cys Ala Thr Thr Thr Gly Thr Gly Gly Gly Cys Ala Ala
            610                 615                 620
Ala Gly Thr Thr Thr Gly Cys Ala Thr Gly Ala Ala Thr Thr Gly
625                 630                 635                 640
Ala Ala Thr Gly Ala Cys Ala Cys Thr Thr Thr Thr Cys Cys Ala Gly
                645                 650                 655
Ala Ala Thr Ala Cys Ala Ala Thr Gly Ala Gly Ala Cys Cys Ala Cys
                660                 665                 670
Thr Gly Ala Gly Gly Ala Ala Thr Cys Gly Ala Thr Cys Ala Ala Gly
            675                 680                 685
Gly Ala Ala Ala Cys Cys Gly Ala Gly Ala Gly Ala Thr Thr Thr Gly
            690                 695                 700
Thr Gly Thr Cys Ala Gly Ala Ala Ala Thr Gly Cys Thr Cys Cys Ala
705                 710                 715                 720
Ala Ala Gly Gly Ala Ala Ala Thr Ala Thr Thr Cys Thr Ala Gly Ala
                725                 730                 735
Gly Thr Gly Ala Ala Gly Cys Cys Ala Thr Ala Gly Thr Gly Ala
            740                 745                 750
Cys Ala Cys Cys Ala Cys Gly Thr Thr Thr Thr Thr Cys Cys Cys Thr
            755                 760                 765
Cys Thr Cys Cys Thr Gly Cys Thr Cys Thr Gly Ala Gly Ala Cys Thr
            770                 775                 780
Thr Thr Gly Ala Thr Gly Gly Thr Gly Ala Thr Cys Thr Cys Gly
785                 790                 795                 800
Gly Cys Ala Ala Cys Ala Thr Thr Gly Cys Thr Ala Ala Ala Ala Cys
                805                 810                 815
Cys Cys Ala Thr Gly Ala Thr Thr Thr Gly Cys Ala Cys Ala Thr Thr
                820                 825                 830
Cys Ala Gly Ala Gly Cys Cys Ala Thr Ala Thr Ala Ala Gly Thr Gly
                835                 840                 845
Ala Ala Ala Ala Thr Cys Gly Thr Gly Ala Thr Gly Ala Ala Gly Thr
850                 855                 860
Thr Gly Ala Ala Gly Cys Thr Gly Thr Gly Ala Ala Ala Ala Ala Cys
865                 870                 875                 880
Thr Thr Ala Thr Ala Cys Cys Cys Cys Ala Gly Thr Thr Ala Thr Ala
                885                 890                 895
Ala Ala Ala Ala Cys Thr Ala Cys Ala Cys Ala Gly Ala Thr Gly Thr
                900                 905                 910
Gly Thr Ala Thr Gly Ala Thr Ala Ala Ala Ala Cys Ala Ala Thr
            915                 920                 925
Cys Thr Thr Thr Thr Gly Ala Cys Ala Ala Thr Ala Ala Gly Ala
            930                 935                 940
Cys Ala Gly Thr Gly Ala Thr Gly Gly Cys Ala Cys Ala Cys Gly Gly
945                 950                 955                 960
Cys Thr Gly Cys Thr Ala Cys Cys Thr Cys Thr Cys Thr Gly Cys Ala
                965                 970                 975
Gly Ala Ala Gly Ala Ala Cys Thr Gly Ala Ala Thr Gly Thr Ala Thr
                980                 985                 990
```

-continued

Thr Cys Cys Ala Thr Gly Ala Ala Cys Gly Ala Gly Gly Ala Gly Cys
995 1000 1005

Ala Thr Cys Cys Ala Thr Cys Gly Cys Ala Cys Ala Cys Thr Gly
1010 1015 1020

Thr Cys Cys Cys Ala Ala Thr Thr Cys Thr Ala Ala Thr Thr Thr
1025 1030 1035

Ala Thr Cys Gly Cys Thr Cys Ala Gly Cys Ala Gly Thr Gly Gly
1040 1045 1050

Ala Thr Thr Thr Cys Thr Ala Ala Ala Thr Gly Thr Gly Cys Thr
1055 1060 1065

Ala Gly Ala Ala Gly Thr Cys Cys Thr Gly Ala Ala Ala Cys Ala
1070 1075 1080

Thr Gly Ala Ala Gly Thr Cys Ala Ala Gly Ala Thr Ala Gly Gly
1085 1090 1095

Gly Cys Thr Gly Gly Gly Thr Ala Cys Ala Gly Ala Cys Gly Thr
1100 1105 1110

Gly Gly Cys Thr Gly Gly Thr Gly Gly Cys Thr Ala Thr Thr Cys
1115 1120 1125

Gly Thr Ala Thr Thr Cys Cys Ala Thr Gly Cys Thr Thr Gly Ala
1130 1135 1140

Thr Gly Cys Ala Ala Thr Cys Ala Gly Ala Ala Gly Ala Gly Cys
1145 1150 1155

Ala Gly Thr Gly Ala Thr Gly Gly Thr Thr Thr Cys Cys Ala Ala
1160 1165 1170

Thr Ala Thr Cys Cys Thr Thr Thr Thr Ala Ala Thr Thr Ala Ala
1175 1180 1185

Thr Ala Ala Gly Gly Thr Ala Ala Ala Thr Gly Ala Gly Ala Ala
1190 1195 1200

Ala Ala Gly Cys Cys Thr Cys Ala Cys Cys Cys Thr Cys Ala Ala
1205 1210 1215

Ala Gly Ala Ala Gly Thr Cys Thr Thr Cys Ala Gly Ala Cys Thr
1220 1225 1230

Ala Gly Cys Thr Ala Cys Thr Cys Thr Thr Gly Gly Ala Gly Gly
1235 1240 1245

Ala Ala Gly Cys Cys Ala Ala Gly Cys Cys Cys Thr Gly Gly Gly
1250 1255 1260

Gly Cys Thr Gly Gly Ala Thr Gly Gly Thr Gly Ala Gly Ala Thr
1265 1270 1275

Thr Gly Gly Ala Ala Ala Cys Thr Thr Thr Gly Ala Ala Gly Thr
1280 1285 1290

Gly Gly Gly Cys Ala Ala Gly Gly Ala Ala Thr Thr Thr Gly Ala
1295 1300 1305

Thr Gly Cys Cys Ala Thr Cys Cys Thr Gly Ala Thr Cys Ala Ala
1310 1315 1320

Cys Cys Cys Cys Ala Ala Ala Gly Cys Ala Thr Cys Cys Gly Ala
1325 1330 1335

Cys Thr Cys Thr Cys Cys Cys Ala Thr Thr Gly Ala Cys Cys Thr
1340 1345 1350

Gly Thr Thr Thr Thr Ala Thr Gly Gly Gly Gly Ala Cys Thr Thr
1355 1360 1365

Thr Thr Thr Thr Gly Gly Thr Gly Ala Thr Ala Thr Thr Thr Cys
1370 1375 1380

-continued

```
Thr Gly Ala Gly Gly Cys Thr Gly Thr Ala Thr Cys Cys Ala
    1385            1390            1395

Gly Ala Ala Ala Thr Thr Cys Cys Thr Cys Thr Ala Thr Cys Thr
    1400            1405            1410

Ala Gly Gly Ala Gly Ala Thr Gly Ala Thr Cys Gly Ala Ala Ala
    1415            1420            1425

Thr Ala Thr Thr Gly Ala Ala Gly Ala Gly Gly Thr Thr Thr Ala
    1430            1435            1440

Thr Gly Thr Gly Gly Gly Cys Gly Gly Ala Ala Ala Gly Cys Ala
    1445            1450            1455

Gly Gly Thr Gly Gly Thr Thr Cys Cys Gly Thr Thr Thr Thr Cys
    1460            1465            1470

Cys Ala Gly Cys Thr Cys Ala Gly Thr Gly Thr Ala Ala Gly Ala
    1475            1480            1485

Cys Cys Cys Thr Cys Gly Gly Gly Cys Gly Thr Cys Thr Ala Thr
    1490            1495            1500

Gly Ala Ala Gly Thr Thr Cys Thr Cys Cys Thr Gly Gly Gly Ala
    1505            1510            1515

Thr Thr Ala Gly Cys Gly Thr Gly Gly Thr Thr Cys Thr Gly Cys
    1520            1525            1530

Ala Thr Cys Thr Cys Cys Thr Thr Gly Thr Gly Cys Cys Cys
    1535            1540            1545

Ala Gly Gly Thr Gly Gly Ala Gly Thr Gly Ala Gly Ala Ala Ala
    1550            1555            1560

Gly Thr Cys Ala Ala Ala Ala Ala Thr Ala Gly Thr Ala Cys
    1565            1570            1575

Cys Thr Thr Gly Thr Thr Cys Thr Thr Gly Gly Gly Ala Thr Gly
    1580            1585            1590

Gly Cys Thr Ala Thr Cys Cys Thr Thr Cys Thr Gly Thr
    1595            1600            1605

Gly Thr Cys Thr Ala Gly Thr Thr Ala Cys Ala Gly Thr Ala Thr
    1610            1615            1620

Thr Cys Ala Cys Thr Thr Gly Ala Cys Ala Ala Ala Thr Ala Gly
    1625            1630            1635

Thr Thr Cys Gly Ala Ala Gly Gly Ala Ala Gly Thr Thr Gly Cys
    1640            1645            1650

Gly Cys Thr Ala Ala Thr Thr Cys Thr Cys Ala Ala Cys Thr Cys
    1655            1660            1665

Thr Gly Gly Thr Thr Gly Ala Gly Ala Gly Gly Thr Thr Cys
    1670            1675            1680

Ala Thr Ala Ala Ala Thr Thr Thr Cys Ala Thr Gly Ala Ala Ala
    1685            1690            1695

Ala Thr Gly Thr Cys Thr Cys Cys Cys Thr Thr Gly Gly Ala
    1700            1705            1710

Gly Cys Thr Gly Cys Thr Cys Ala Gly Ala Cys Thr Thr Ala Cys
    1715            1720            1725

Thr Thr Thr Ala Ala Gly Cys Thr Cys Ala Ala Ala Cys Ala Gly
    1730            1735            1740

Ala Ala Gly Gly Gly Ala Ala Thr Gly Cys Thr Ala Thr Thr Ala
    1745            1750            1755

Cys Thr Gly Gly Thr Gly Gly Thr Gly Thr Thr Cys Cys Thr Ala
    1760            1765            1770

Cys Gly Ala Thr Ala Ala Gly Ala Cys Thr Thr Ala Ala Gly Cys
```

-continued

```
              1775                1780                1785
Ala  Ala  Ala  Gly  Cys  Cys  Thr  Thr  Thr  Thr  Cys  Ala  Thr  Ala
              1790                1795                1800

Thr  Thr  Thr  Gly  Ala  Ala  Ala  Thr  Ala  Thr  Gly  Gly  Ala  Ala
              1805                1810                1815

Ala  Gly  Ala  Ala  Ala  Ala  Gly  Ala  Thr  Gly  Thr  Thr  Cys  Cys  Thr
              1820                1825                1830

Ala  Ala  Ala  Ala  Gly  Gly  Thr  Thr  Ala  Gly  Ala  Thr  Ala  Thr  Thr
              1835                1840                1845

Thr  Thr  Gly  Ala  Gly  Cys  Thr  Ala  Ala  Thr  Ala  Ala  Thr  Thr  Gly
              1850                1855                1860

Cys  Ala  Ala  Ala  Ala  Ala  Thr  Ala  Gly  Ala  Ala  Gly  Ala  Cys
              1865                1870                1875

Thr  Gly  Ala  Ala  Ala  Ala  Thr  Gly  Gly  Ala  Cys  Cys  Cys  Ala  Thr
              1880                1885                1890

Gly  Ala  Gly  Ala  Gly  Thr  Ala  Thr  Ala  Thr  Thr  Thr  Thr  Ala
              1895                1900                1905

Thr  Gly  Ala  Gly  Gly  Gly  Ala  Gly  Cys  Ala  Ala  Ala  Gly  Thr
              1910                1915                1920

Thr  Ala  Gly  Ala  Cys  Thr  Gly  Ala  Gly  Ala  Ala  Cys  Ala  Ala  Ala
              1925                1930                1935

Thr  Gly  Thr  Thr  Ala  Gly  Ala  Ala  Ala  Thr  Cys  Ala  Cys  Thr
              1940                1945                1950

Thr  Cys  Ala  Gly  Ala  Thr  Thr  Gly  Thr  Gly  Thr  Thr  Gly  Ala
              1955                1960                1965

Ala  Ala  Ala  Thr  Thr  Ala  Thr  Ala  Thr  Ala  Cys  Cys  Gly  Ala  Gly
              1970                1975                1980

Cys  Ala  Thr  Ala  Cys  Thr  Ala  Ala  Thr  Thr  Ala  Ala  Ala  Ala
              1985                1990                1995

Ala  Gly  Ala  Gly  Ala  Ala  Cys  Thr  Thr  Gly  Thr  Thr  Gly  Ala  Ala
              2000                2005                2010

Thr  Thr  Thr  Ala  Ala  Ala  Ala  Cys  Gly  Thr  Gly  Thr  Thr  Thr
              2015                2020                2025

Cys  Thr  Ala  Gly  Gly  Thr  Thr  Gly  Ala  Cys  Cys  Thr  Thr  Gly  Thr
              2030                2035                2040

Gly  Thr  Thr  Thr  Thr  Ala  Gly  Ala  Ala  Ala  Thr  Thr  Thr  Gly  Cys
              2045                2050                2055

Ala  Cys  Thr  Thr  Ala  Ala  Thr  Gly  Gly  Ala  Ala  Thr  Thr  Thr  Gly
              2060                2065                2070

Cys  Ala  Thr  Thr  Thr  Cys  Ala  Gly  Ala  Gly  Ala  Thr  Gly  Thr  Gly
              2075                2080                2085

Thr  Thr  Ala  Gly  Thr  Gly  Thr  Gly  Thr  Gly  Cys  Thr  Thr  Thr
              2090                2095                2100

Gly  Cys  Cys  Thr  Thr  Cys  Thr  Thr  Thr  Gly  Gly  Gly  Ala  Thr
              2105                2110                2115

Gly  Ala  Ala  Thr  Gly  Thr  Cys  Ala  Gly  Ala  Ala  Ala  Thr  Thr  Gly
              2120                2125                2130

Ala  Ala  Thr  Gly  Cys  Cys  Ala  Cys  Ala  Thr  Gly  Cys  Thr  Thr  Thr
              2135                2140                2145

Cys  Ala  Thr  Ala  Ala  Thr  Ala  Thr  Ala  Gly  Thr  Thr  Thr  Thr  Gly
              2150                2155                2160

Thr  Gly  Cys  Thr  Thr  Cys  Ala  Ala  Ala  Gly  Thr  Gly  Thr  Thr  Thr
              2165                2170                2175
```

```
Gly Ala Cys Ala Gly Ala Ala Gly Thr Thr Gly Gly Thr Ala
    2180                2185                2190

Thr Thr Ala Ala Ala Gly Ala Thr Thr Ala Ala Ala Gly Thr
2195                2200                2205

Cys Thr Cys Thr Thr Ala Gly Gly Ala Ala Thr Ala Thr Thr Ala
2210                2215                2220

Thr Thr Cys Ala Thr Gly Thr Ala Ala Cys Thr Cys Cys Ala Thr
    2225                2230                2235

Gly Gly Thr Ala Thr Ala Ala Ala Thr Ala Gly Thr Thr Gly Thr
2240                2245                2250

Ala Thr Thr Thr Thr Thr Gly Thr Gly Thr Ala Cys Thr Thr Thr
    2255                2260                2265

Ala Ala Ala Ala Thr Cys Ala Ala Cys Thr Thr Ala Thr Ala Ala
    2270                2275                2280

Cys Thr Gly Thr Gly Ala Gly Ala Thr Gly Thr Thr Ala Thr Thr
    2285                2290                2295

Gly Cys Thr Thr Cys Cys Ala Thr Thr Thr Thr Ala Thr Thr Ala
2300                2305                2310

Gly Ala Ala Gly Ala Gly Ala Ala Ala Cys Ala Ala Ala Thr Thr
2315                2320                2325

Cys Cys Ala Thr Gly Cys Thr Thr Thr Ala Thr Gly Gly Ala Ala
    2330                2335                2340

Ala Thr Thr Ala Thr Gly Thr Ala Gly Ala Cys Thr Gly Gly Ala
    2345                2350                2355

Gly Thr Cys Thr Thr Cys Gly Thr Gly Ala Ala Cys Thr Gly Gly
    2360                2365                2370

Gly Gly Cys Ala Ala Gly Thr Gly Cys Thr Gly Gly Cys Ala Thr
    2375                2380                2385

Cys Cys Ala Gly Gly Ala Gly Cys Cys Gly Cys Cys Ala Ala Thr
    2390                2395                2400

Ala Cys Thr Ala Ala Cys Ala Gly Gly Ala Cys Ala Gly Gly Thr
    2405                2410                2415

Thr Cys Cys Ala Thr Thr Gly Cys Cys Ala Thr Gly Gly Cys Cys
    2420                2425                2430

Thr Ala Thr Thr Cys Cys Ala Thr Cys Cys Ala Ala Ala Cys Ala
    2435                2440                2445

Ala Thr Gly Thr Gly Thr Thr Gly Thr Ala Gly Thr Thr Thr Cys
    2450                2455                2460

Thr Gly Gly Ala Ala Ala Thr Cys Cys Ala Thr Ala Cys Thr
    2465                2470                2475

Cys Ala Gly Ala Thr Ala Thr Cys Ala Gly Thr Cys Thr Gly Cys
    2480                2485                2490

Thr Ala Gly Ala Ala Cys Thr Thr Ala Ala Ala Thr Gly
    2495                2500                2505

Ala Ala Gly Gly Ala Cys Ala Ala Thr Cys Cys Thr Gly Thr
    2510                2515                2520

Thr Ala Ala Ala Gly Ala Ala Ala Thr Ala Thr Thr Gly Thr Thr
    2525                2530                2535

Ala Ala Ala Ala Ala Thr Cys Thr Thr Thr Ala Ala Ala Cys Cys
    2540                2545                2550

Cys Thr Gly Thr Gly Thr Ala Thr Thr Gly Ala Ala Ala Gly Cys
    2555                2560                2565
```

-continued

```
Ala Cys  Thr Cys Thr Ala Thr  Thr Thr Thr Cys Thr  Ala Ala Thr
    2570                 2575                 2580

Thr Thr  Thr Ala Thr Cys Cys  Ala Gly Thr Thr Thr  Thr Cys Thr
    2585                 2590                 2595

Gly Thr  Thr Thr Ala Ala Cys  Cys Cys Cys Thr Thr  Ala Thr Ala
    2600                 2605                 2610

Ala Thr  Thr Thr Thr Thr Ala  Gly Gly Ala Thr Ala  Thr Thr Ala
    2615                 2620                 2625

Gly Ala  Ala Thr Thr Thr Thr  Cys Gly Gly Ala Thr  Ala Ala Thr
    2630                 2635                 2640

Gly Ala  Ala Gly Ala Gly Thr  Ala Cys Ala Thr Ala  Ala Thr Gly
    2645                 2650                 2655

Thr Cys  Cys Thr Ala Cys Thr  Thr Ala Ala Thr Ala  Thr Thr Thr
    2660                 2665                 2670

Ala Thr  Gly Thr Thr Ala Ala  Thr Ala Gly Gly Ala  Cys Thr Thr
    2675                 2680                 2685

Ala Ala  Thr Thr Cys Thr Thr  Ala Cys Thr Ala Gly  Ala Cys Ala
    2690                 2695                 2700

Thr Cys  Thr Ala Gly Gly Ala  Ala Cys Ala Thr Thr  Ala Cys Ala
    2705                 2710                 2715

Ala Ala  Gly Cys Ala Ala Ala  Gly Ala Ala Thr Ala  Thr Thr Thr
    2720                 2725                 2730

Thr Thr  Ala Thr Gly Cys Thr  Thr Cys Cys Ala Thr  Ala Ala Cys
    2735                 2740                 2745

Cys Thr  Ala Gly Ala Ala Thr  Thr Ala Ala Ala Ala  Cys Cys Ala
    2750                 2755                 2760

Ala Ala  Thr Thr Ala Thr Gly  Ala Cys Cys Thr Thr  Ala Thr Gly
    2765                 2770                 2775

Ala Thr  Ala Ala Ala Thr Cys  Thr Thr Thr Ala Ala  Gly Thr Ala
    2780                 2785                 2790

Thr Thr  Gly Gly Thr Gly Thr  Gly Ala Ala Thr Gly  Thr Thr Ala
    2795                 2800                 2805

Thr Thr  Thr Ala Ala Ala Thr  Thr Cys Thr Ala Thr  Ala Thr Thr
    2810                 2815                 2820

Thr Thr  Thr Cys Thr Thr Ala  Thr Thr Thr Ala Ala  Thr Thr Ala
    2825                 2830                 2835

Cys Ala  Ala Ala Thr Ala Cys  Thr Ala Thr Ala Ala  Thr Thr Gly
    2840                 2845                 2850

Ala Gly  Cys Ala Ala Gly Gly  Ala Ala Ala Ala Gly  Gly Ala Ala
    2855                 2860                 2865

Thr Ala  Gly Ala Cys Thr Thr  Thr Cys Thr Thr Cys  Ala Thr Ala
    2870                 2875                 2880

Thr Ala  Thr Thr Ala Thr Ala  Ala Cys Ala Cys Thr  Cys Ala Thr
    2885                 2890                 2895

Thr Cys  Cys Thr Ala Gly Ala  Gly Cys Thr Thr Ala  Gly Gly Gly
    2900                 2905                 2910

Gly Thr  Gly Ala Cys Thr Cys  Thr Thr Thr Ala Ala  Thr Ala Thr
    2915                 2920                 2925

Thr Ala  Cys Cys Cys Thr Thr  Ala Thr Ala Gly Thr  Ala Gly Ala
    2930                 2935                 2940

Ala Ala  Ala Cys Thr Thr Thr  Ala Thr Gly Thr Ala  Ala Thr Ala
    2945                 2950                 2955

Thr Ala  Gly Cys Thr Ala Ala  Cys Thr Cys Cys Ala  Thr Ala Thr
```

-continued

|  |  |  |
|---|---|---|
| 2960 | 2965 | 2970 |

Thr Thr Ala Cys Ala Gly Ala Ala Cys Ala Ala Ala Ala Ala
      2975                2980                2985

Cys Ala Cys Ala Gly Thr Thr Cys Cys Cys Cys Cys Thr Cys Cys
      2990                2995                3000

Thr Gly Thr Ala Gly Thr Ala Thr Ala Ala Ala Thr Thr Thr Thr
      3005                3010                3015

Ala Thr Thr Thr Thr Cys Ala Cys Ala Thr Ala Cys Thr Thr Gly
      3020                3025                3030

Gly Cys Thr Ala Ala Thr Thr Thr Ala Gly Cys Ala Gly Thr Ala
      3035                3040                3045

Ala Thr Thr Gly Gly Cys Cys Cys Cys Ala Thr Thr Thr Thr Thr
      3050                3055                3060

Thr Cys Cys Cys Thr Ala Ala Thr Ala Gly Ala Ala Ala Thr Ala
      3065                3070                3075

Cys Thr Thr Thr Thr Ala Gly Ala Thr Thr Thr Gly Ala Thr Thr
      3080                3085                3090

Ala Thr Gly Thr Ala Thr Ala Cys Ala Thr Gly Ala Cys Ala Cys
      3095                3100                3105

Cys Thr Ala Ala Ala Gly Ala Gly Gly Gly Ala Ala Cys Ala Ala
      3110                3115                3120

Ala Ala Gly Thr Thr Thr Ala Gly Thr Thr Thr Thr Ala Thr Thr
      3125                3130                3135

Thr Thr Thr Thr Thr Ala Ala Thr Ala Ala Ala Cys Ala Ala Cys
      3140                3145                3150

Ala Gly Ala Gly Thr Thr Thr Gly Thr Thr Thr Thr Gly Thr Gly
      3155                3160                3165

Ala Gly Ala Thr Ala Ala Gly Thr Ala Gly Cys Thr Thr Ala Gly
      3170                3175                3180

Thr Ala Ala Ala Cys Cys Cys Ala Gly Thr Thr Thr Cys Cys Ala
      3185                3190                3195

Gly Thr Cys Thr Thr Ala Gly Thr Cys Thr Gly Thr Ala Thr Thr
      3200                3205                3210

Thr Cys Cys Ala Ala Thr Ala Thr Thr Thr Cys Thr Ala Ala Thr
      3215                3220                3225

Thr Cys Cys Thr Gly Ala Gly Cys Cys Ala Thr Gly Thr Cys Ala
      3230                3235                3240

Ala Ala Gly Ala Thr Gly Cys Cys Thr Thr Gly Cys Cys Ala Ala
      3245                3250                3255

Ala Thr Thr Thr Cys Thr Cys Cys Cys Cys Ala Thr Thr Thr Cys
      3260                3265                3270

Thr Cys Thr Ala Cys Gly Gly Gly Gly Cys Thr Ala Gly Cys Ala
      3275                3280                3285

Ala Gly Ala Ala Thr Cys Thr Thr Cys Ala Gly Cys Thr Thr Thr
      3290                3295                3300

Ala Thr Cys Cys Cys Thr Cys Ala Ala Cys Cys Cys Cys Thr Gly
      3305                3310                3315

Cys Cys Ala Ala Ala Gly Gly Ala Ala Cys Thr Thr Gly Ala Thr
      3320                3325                3330

Thr Ala Cys Ala Thr Gly Gly Thr Gly Thr Cys Thr Ala Ala Cys
      3335                3340                3345

Cys Ala Ala Ala Thr Gly Ala Gly Thr Ala Gly Gly Cys Thr Thr
      3350                3355                3360

```
Ala Gly Gly Ala Ala Thr Thr Thr Gly Ala Thr Gly Ala Ala
    3365                3370                3375
Ala Thr Gly Thr Gly Thr Ala Ala Gly Ala Thr Thr Cys Ala Cys
    3380                3385                3390
Thr Thr Ala Cys Ala Gly Gly Cys Ala Gly Thr Ala Gly Cys Thr
    3395                3400                3405
Gly Cys Thr Thr Cys Thr Ala Gly Cys Ala Thr Thr Thr Gly Cys
    3410                3415                3420
Ala Ala Gly Ala Thr Cys Cys Thr Ala Cys Ala Cys Thr Thr Thr
    3425                3430                3435
Thr Ala Cys Cys Thr Thr Cys Thr Thr Thr Ala Ala Gly Gly Gly
    3440                3445                3450
Thr Gly Thr Ala Cys Ala Thr Thr Thr Thr Gly Ala Thr Gly Thr
    3455                3460                3465
Thr Gly Ala Ala Cys Ala Thr Cys Ala Gly Thr Thr Thr Thr Cys
    3470                3475                3480
Ala Thr Gly Thr Ala Gly Ala Cys Thr Thr Ala Gly Gly Ala Cys
    3485                3490                3495
Thr Cys Ala Thr Gly Thr Gly Cys Ala Gly Thr Ala Ala Ala Thr
    3500                3505                3510
Ala Thr Ala Ala Ala Thr Ala Ala Gly Thr Gly Thr Ala Gly Cys
    3515                3520                3525
Ala Thr Cys Ala Gly Ala Ala Gly Cys Ala Gly Thr Ala Gly Gly
    3530                3535                3540
Ala Ala Thr Gly Gly Cys Cys Gly Thr Ala Thr Ala Cys Ala Ala
    3545                3550                3555
Cys Cys Ala Thr Cys Cys Thr Gly Thr Thr Ala Ala Ala Cys Ala
    3560                3565                3570
Thr Thr Thr Ala Ala Ala Thr Thr Thr Ala Gly Cys Thr Cys Thr
    3575                3580                3585
Gly Ala Thr Ala Gly Thr Gly Thr Gly Thr Thr Ala Ala Gly Ala
    3590                3595                3600
Cys Cys Thr Gly Ala Ala Thr Ala Thr Cys Thr Thr Thr Cys Cys
    3605                3610                3615
Thr Ala Gly Thr Ala Ala Ala Ala Ala Thr Ala Gly Gly Ala Thr
    3620                3625                3630
Gly Thr Gly Thr Thr Gly Ala Ala Ala Thr Gly Thr Thr Thr Ala
    3635                3640                3645
Thr Ala Thr Gly Thr Ala Cys Thr Thr Thr Gly Ala Thr Cys Thr
    3650                3655                3660
Cys Thr Cys Cys Gly Cys Ala Thr Cys Ala Cys Thr Thr Ala Thr
    3665                3670                3675
Ala Ala Cys Thr Thr Ala Thr Gly Thr Gly Cys Thr Thr Thr Ala
    3680                3685                3690
Thr Thr Thr Cys Thr Cys Cys Ala Ala Gly Thr Gly Cys Gly Gly
    3695                3700                3705
Thr Gly Thr Thr Cys Cys Thr Gly Ala Ala Thr Gly Thr Thr Gly
    3710                3715                3720
Thr Ala Thr Ala Thr Gly Cys Thr Thr Thr Thr Thr Thr Thr Thr
    3725                3730                3735
Thr Thr Cys Thr Gly Thr Ala Cys Cys Ala Cys Ala Gly Gly Cys
    3740                3745                3750
```

-continued

```
Ala Thr Thr Ala Gly Cys Thr Ala Thr Ala Cys Cys Thr Gly Gly
    3755                3760                3765
Gly Gly Cys Cys Ala Gly Ala Thr Thr Thr Cys Thr Gly Cys
    3770                3775                3780
Ala Cys Thr Thr Thr Gly Ala Ala Ala Thr Gly Thr Ala Gly Cys
    3785                3790                3795
Cys Thr Thr Thr Gly Cys Cys Thr Ala Ala Thr Gly Thr Ala Gly
    3800                3805                3810
Gly Thr Thr Gly Ala Cys Thr Thr Cys Thr Ala Ala Ala Thr
    3815                3820                3825
Thr Gly Thr Gly Gly Ala Gly Ala Gly Gly Cys Ala Cys Thr Thr
    3830                3835                3840
Thr Thr Cys Cys Ala Ala Gly Cys Cys Ala Ala Thr Cys Thr Thr
    3845                3850                3855
Ala Thr Thr Thr Gly Thr Cys Ala Cys Thr Thr Thr Thr Thr Gly
    3860                3865                3870
Thr Thr Thr Thr Ala Ala Thr Ala Thr Cys Thr Thr Gly Cys Thr
    3875                3880                3885
Cys Thr Cys Thr Gly Ala Cys Ala Gly Gly Ala Ala Ala Gly Ala
    3890                3895                3900
Ala Ala Cys Ala Ala Thr Thr Cys Ala Cys Thr Ala Cys Cys
    3905                3910                3915
Ala Gly Cys Cys Thr Cys Cys Thr Cys Ala Cys Cys Cys Cys Ala
    3920                3925                3930
Thr Cys Cys Thr Cys Cys Ala Cys Cys Ala Thr Thr Thr Cys Cys
    3935                3940                3945
Thr Thr Ala Ala Thr Gly Thr Thr Cys Cys Ala Thr Gly Gly Thr
    3950                3955                3960
Ala Thr Thr Thr Thr Cys Ala Ala Cys Ala Gly Ala Ala Thr Ala
    3965                3970                3975
Cys Ala Cys Thr Thr Thr Gly Ala Ala Ala Gly Gly Thr Ala Ala
    3980                3985                3990
Ala Ala Ala Cys Ala Ala Thr Thr Cys Ala Ala Ala Ala Gly Thr
    3995                4000                4005
Ala Thr Cys Gly Ala Thr Thr Ala Thr Cys Ala Thr Ala Ala Ala
    4010                4015                4020
Thr Thr Cys Ala Cys Ala Ala Ala Thr Ala Thr Thr Thr Thr
    4025                4030                4035
Thr Ala Cys Ala Ala Cys Cys Ala Gly Ala Ala Cys Ala Cys Ala
    4040                4045                4050
Ala Ala Ala Gly Cys Ala Gly Gly Cys Thr Ala Gly Thr Cys Ala
    4055                4060                4065
Gly Cys Thr Ala Ala Gly Gly Thr Ala Ala Ala Thr Thr Thr Cys
    4070                4075                4080
Ala Thr Thr Thr Thr Cys Ala Ala Ala Thr Gly Ala Gly Ala Gly
    4085                4090                4095
Gly Gly Ala Ala Ala Cys Ala Thr Gly Gly Gly Ala Ala Gly Thr
    4100                4105                4110
Ala Ala Ala Ala Gly Ala Thr Thr Ala Gly Gly Ala Thr Gly Thr
    4115                4120                4125
Gly Ala Ala Ala Gly Gly Thr Gly Thr Cys Cys Thr Ala Ala
    4130                4135                4140
Ala Cys Ala Gly Ala Cys Cys Ala Ala Gly Gly Ala Gly Ala Cys
```

-continued

```
                4145                4150                4155

Thr Gly Thr Thr Thr Cys Cys Thr Ala Ala Thr Thr Ala Thr
        4160                4165                4170

Thr Cys Thr Cys Thr Thr Gly Gly Cys Thr Gly Gly Thr Thr Cys
    4175                4180                4185

Thr Cys Thr Cys Gly Thr Thr Gly Ala Ala Thr Ala Thr Cys
    4190                4195                4200

Ala Gly Ala Cys Cys Cys Ala Ala Gly Ala Gly Gly Ala Ala
    4205                4210                4215

Ala Thr Cys Thr Thr Gly Gly Ala Ala Cys Ala Gly Gly Cys Thr
    4220                4225                4230

Cys Cys Cys Thr Thr Cys Ala Thr Gly Cys Cys Ala Ala Gly Gly
    4235                4240                4245

Gly Thr Cys Thr Thr Cys Thr Ala Ala Gly Thr Thr Ala Ala
    4250                4255                4260

Thr Gly Cys Thr Gly Thr Gly Ala Gly Cys Ala Thr Thr Gly Ala
    4265                4270                4275

Gly Cys Cys Cys Cys Ala Thr Thr Ala Ala Ala Ala Cys Thr
    4280                4285                4290

Cys Thr Thr Thr Thr Thr Thr Ala Cys Thr Thr Cys Ala Gly Ala
    4295                4300                4305

Ala Ala Gly Ala Cys Thr Thr Cys Thr Ala Cys Ala Gly Gly Thr
    4310                4315                4320

Thr Ala Ala Ala Gly Gly Gly Ala Ala Ala Gly Ala Ala Ala Thr
    4325                4330                4335

Gly Gly Thr Gly Gly Gly Ala Ala Ala Cys Thr Cys Thr Cys Cys
    4340                4345                4350

Cys Cys Gly Thr Ala Ala Thr Gly Cys Thr Thr Ala Gly Cys Cys
    4355                4360                4365

Ala Ala Cys Thr Thr Thr Ala Ala Ala Gly Thr Gly Thr Ala Cys
    4370                4375                4380

Cys Cys Thr Cys Cys Ala Ala Thr Ala Thr Cys Cys Cys Cys Ala
    4385                4390                4395

Thr Thr Gly Gly Cys Ala Ala Cys Thr Gly Cys Ala Gly Cys Thr
    4400                4405                4410

Gly Ala Gly Ala Thr Cys Thr Thr Ala Gly Ala Gly Ala Gly Gly
    4415                4420                4425

Ala Ala Ala Thr Ala Thr Ala Ala Cys Cys Gly Gly Thr Gly Thr
    4430                4435                4440

Gly Ala Gly Gly Thr Cys Thr Ala Gly Cys Ala Ala Thr Gly Cys
    4445                4450                4455

Ala Thr Thr Thr Thr Gly Ala Ala Thr Cys Thr Thr Cys Ala Cys
    4460                4465                4470

Thr Cys Cys Cys Thr Ala Cys Cys Ala Gly Gly Cys Thr Cys Thr
    4475                4480                4485

Thr Cys Cys Thr Ala Thr Thr Thr Thr Ala Ala Thr Cys Thr
    4490                4495                4500

Cys Thr Thr Cys Ala Cys Cys Thr Cys Ala Gly Ala Ala Cys Thr
    4505                4510                4515

Ala Gly Ala Cys Ala Thr Ala Thr Gly Gly Ala Gly Ala Gly Cys
    4520                4525                4530

Thr Thr Thr Ala Ala Ala Gly Gly Cys Ala Ala Gly Cys Thr Gly
    4535                4540                4545
```

-continued

```
Gly Ala Ala Gly Gly Cys Ala Cys Ala Thr Thr Gly Thr Ala Thr
    4550                4555                4560
Cys Ala Ala Thr Thr Cys Thr Ala Cys Cys Thr Thr Gly Thr Gly
    4565                4570                4575
Cys Thr Gly Thr Ala Cys Gly Thr Gly Gly Ala Gly Ala Gly
    4580                4585                4590
Ala Thr Cys Cys Ala Ala Ala Thr Thr Thr Gly Gly Ala Thr
    4595                4600                4605
Gly Cys Thr Thr Cys Thr Gly Gly Ala Gly Ala Cys Thr Gly Thr
    4610                4615                4620
Thr Ala Gly Ala Cys Ala Thr Cys Thr Thr Thr Cys Ala Thr
    4625                4630                4635
Thr Gly Thr Thr Gly Thr Cys Cys Ala Thr Thr Thr Thr Ala
    4640                4645                4650
Ala Ala Gly Thr Thr Gly Ala Thr Gly Ala Thr Gly Ala Thr Thr
    4655                4660                4665
Gly Cys Thr Gly Gly Ala Ala Ala Cys Ala Thr Thr Cys Ala Cys
    4670                4675                4680
Ala Thr Gly Cys Thr Thr Ala Ala Ala Ala Gly Cys Ala Ala Thr
    4685                4690                4695
Gly Gly Thr Gly Thr Gly Ala Gly Thr Thr Ala Thr Thr Ala Ala
    4700                4705                4710
Cys Gly Gly Gly Thr Ala Ala Ala Cys Thr Ala Ala Gly Ala Ala
    4715                4720                4725
Gly Thr Ala Thr Gly Thr Thr Ala Thr Ala Gly Gly Cys Ala Ala
    4730                4735                4740
Thr Gly Ala Cys Thr Thr Gly Ala Ala Ala Thr Gly Gly Thr Thr
    4745                4750                4755
Thr Thr Thr Ala Ala Ala Thr Thr Gly Thr Ala Thr Gly Gly Ala
    4760                4765                4770
Thr Thr Gly Thr Thr Ala Ala Gly Ala Ala Thr Thr Thr Thr Thr
    4775                4780                4785
Gly Ala Ala Ala Thr Thr Thr Thr Thr Thr Thr Thr Thr Thr Thr
    4790                4795                4800
Thr Thr Thr Thr Gly Gly Ala Cys Ala Gly Cys Thr Thr Cys Ala
    4805                4810                4815
Ala Gly Gly Ala Gly Ala Thr Gly Thr Thr Ala Gly Cys Ala Ala
    4820                4825                4830
Thr Thr Thr Cys Ala Gly Ala Thr Ala Thr Ala Cys Thr Ala Gly
    4835                4840                4845
Cys Cys Ala Gly Thr Thr Thr Ala Gly Gly Thr Ala Thr Gly Ala
    4850                4855                4860
Cys Thr Thr Thr Gly Gly Ala Ala Gly Thr Gly Cys Ala Gly Ala
    4865                4870                4875
Ala Ala Cys Ala Gly Ala Ala Gly Gly Ala Thr Ala Cys Thr Gly
    4880                4885                4890
Thr Thr Ala Gly Ala Ala Ala Ala Thr Cys Cys Thr Ala Ala Cys
    4895                4900                4905
Ala Thr Thr Gly Gly Thr Cys Thr Cys Cys Ala Thr Gly Cys Ala
    4910                4915                4920
Thr Gly Thr Gly Thr Thr Cys Ala Cys Ala Cys Cys Thr Gly Gly
    4925                4930                4935
```

-continued

```
Thr Cys Thr Cys Ala Cys Thr Gly Cys Cys Thr Thr Cys Cys
    4940              4945              4950
Thr Thr Cys Thr Cys Ala Thr Ala Gly Cys Cys Cys Thr Gly Ala
    4955              4960              4965
Gly Thr Gly Thr Gly Ala Ala Ala Gly Ala Thr Thr Gly Ala Gly
    4970              4975              4980
Ala Gly Thr Thr Gly Ala Gly Gly Ala Ala Thr Thr Gly Cys Thr
    4985              4990              4995
Thr Thr Gly Thr Gly Gly Ala Thr Cys Thr Thr Gly Thr Cys Cys
    5000              5005              5010
Ala Ala Ala Thr Thr Thr Ala Gly Thr Gly Ala Ala Ala Thr Gly
    5015              5020              5025
Thr Gly Gly Ala Gly Thr Cys Ala Ala Cys Cys Ala Gly Gly Cys
    5030              5035              5040
Cys Ala Ala Thr Gly Ala Thr Gly Ala Ala Ala Thr Thr Ala Ala
    5045              5050              5055
Ala Thr Gly Thr Ala Ala Ala Thr Thr Cys Cys Ala Ala Gly Ala
    5060              5065              5070
Gly Gly Gly Cys Thr Thr Thr Cys Ala Cys Ala Gly Thr Cys Cys
    5075              5080              5085
Ala Cys Ala Gly Gly Gly Cys Thr Cys Ala Ala Ala Thr Gly Ala
    5090              5095              5100
Cys Thr Thr Gly Gly Gly Thr Ala Ala Cys Ala Gly Ala Ala Gly
    5105              5110              5115
Thr Thr Ala Thr Thr Cys Thr Thr Ala Gly Cys Thr Thr Ala Cys
    5120              5125              5130
Cys Thr Gly Thr Thr Ala Thr Gly Thr Gly Ala Cys Ala Gly Thr
    5135              5140              5145
Gly Ala Thr Thr Thr Ala Cys Cys Thr Gly Thr Cys Cys Ala Thr
    5150              5155              5160
Thr Thr Cys Cys Ala Ala Cys Cys Cys Ala Ala Ala Ala Gly Cys
    5165              5170              5175
Cys Thr Gly Thr Cys Ala Gly Ala Ala Ala Gly Cys Ala Thr Thr
    5180              5185              5190
Cys Thr Thr Ala Gly Ala Gly Ala Ala Ala Cys Cys Ala
    5195              5200              5205
Cys Thr Thr Thr Ala Cys Ala Thr Thr Thr Gly Thr Thr Gly Thr
    5210              5215              5220
Thr Ala Ala Ala Cys Thr Cys Cys Thr Gly Ala Thr Thr Gly Cys
    5225              5230              5235
Thr Ala Cys Thr Cys Thr Thr Ala Ala Gly Ala Ala Thr Ala Thr
    5240              5245              5250
Ala Cys Ala Thr Gly Thr Ala Thr Gly Thr Ala Thr Thr Cys Ala
    5255              5260              5265
Thr Ala Gly Gly Ala Ala Cys Ala Thr Thr Thr Thr Thr Thr Thr
    5270              5275              5280
Cys Thr Cys Ala Ala Thr Ala Thr Thr Thr Gly Thr Ala Thr Gly
    5285              5290              5295
Ala Thr Thr Cys Gly Cys Thr Thr Ala Cys Thr Gly Thr Thr Ala
    5300              5305              5310
Thr Thr Gly Thr Gly Cys Thr Gly Ala Gly Thr Gly Ala Gly Cys
    5315              5320              5325
Thr Cys Cys Thr Ala Thr Gly Thr Gly Cys Thr Thr Cys Ala Gly
```

```
                     5330              5335              5340
Ala Cys  Ala Ala Ala Ala Ala  Thr Ala Ala Ala
    5345              5350

<210> SEQ ID NO 5
<211> LENGTH: 454
<212> TYPE: PRT
<213> ORGANISM: Rattus norvegicus

<400> SEQUENCE: 5

Met Cys Ala Ala Arg Thr Pro Gln Leu Ala Leu Ile Phe Arg Gly Thr
1               5                   10                  15

Phe Val His Ser Thr Trp Thr Cys Pro Met Glu Val Leu Arg Asp His
                20                  25                  30

Leu Leu Gly Val Ser Asp Ser Gly Lys Ile Val Phe Leu Glu Glu Ser
            35                  40                  45

Ser Gln Gln Glu Lys Leu Ala Lys Glu Trp Cys Phe Lys Pro Cys Glu
    50                  55                  60

Ile Arg Glu Leu Ser His His Glu Phe Phe Met Pro Gly Leu Val Asp
65                  70                  75                  80

Thr His Ile His Ala Pro Gln Tyr Ala Phe Ala Gly Ser Asn Val Asp
                85                  90                  95

Leu Pro Leu Leu Asp Trp Leu Asn Lys Tyr Thr Phe Pro Thr Glu Lys
            100                 105                 110

Arg Phe Gln Ser Thr Asp Val Ala Glu Glu Val Tyr Thr Arg Val Val
        115                 120                 125

Arg Arg Thr Leu Lys Asn Gly Thr Thr Thr Ala Cys Tyr Phe Gly Thr
130                 135                 140

Ile His Thr Asp Ser Ser Leu Ile Leu Ala Glu Ile Thr Asp Lys Phe
145                 150                 155                 160

Gly Gln Arg Ala Phe Val Gly Lys Val Cys Met Asp Leu Asn Asn Thr
                165                 170                 175

Val Pro Glu Tyr Lys Glu Thr Thr Glu Glu Ser Val Lys Glu Thr Glu
            180                 185                 190

Arg Phe Val Ser Glu Met Leu Gln Lys Asn Tyr Ser Arg Val Lys Pro
        195                 200                 205

Ile Val Thr Pro Arg Phe Ser Leu Ser Cys Thr Glu Thr Leu Met Ser
    210                 215                 220

Glu Leu Gly Asn Ile Ala Lys Thr His Asp Leu Tyr Ile Gln Ser His
225                 230                 235                 240

Ile Ser Glu Asn Arg Glu Glu Ile Glu Ala Val Lys Ser Leu Tyr Pro
                245                 250                 255

Gly Tyr Lys Asn Tyr Thr Asp Val Tyr Asp Lys Asn Asn Leu Leu Thr
            260                 265                 270

Asn Lys Thr Val Met Ala His Gly Cys Tyr Leu Ser Glu Glu Glu Leu
        275                 280                 285

Asn Val Phe Ser Glu Arg Gly Ala Ser Ile Ala His Cys Pro Asn Ser
    290                 295                 300

Asn Leu Ser Leu Ser Ser Gly Leu Leu Asn Val Leu Asp Val Leu Lys
305                 310                 315                 320

His Lys Val Lys Ile Gly Leu Gly Thr Asp Val Ala Gly Gly Tyr Ser
                325                 330                 335

Tyr Ser Met Leu Asp Ala Ile Arg Arg Ala Val Met Val Ser Asn Val
            340                 345                 350
```

```
Leu Leu Ile Asn Lys Val Asn Glu Lys Ser Leu Thr Leu Lys Glu Val
        355                 360                 365

Phe Arg Leu Ala Thr Leu Gly Gly Ser Gln Ala Leu Gly Leu Asp Arg
    370                 375                 380

Glu Ile Gly Asn Phe Glu Val Gly Lys Asp Phe Asp Ala Leu Leu Ile
385                 390                 395                 400

Asn Pro Arg Ala Ser Asp Ser Pro Ile Asp Leu Phe Cys Gly Asp Phe
                405                 410                 415

Val Gly Asp Ile Ser Glu Ala Val Ile Gln Lys Phe Leu Tyr Leu Gly
            420                 425                 430

Asp Asp Arg Asn Ile Glu Glu Val Tyr Val Gly Lys Gln Val Val
        435                 440                 445

Pro Phe Ser Ser Ser Val
        450

<210> SEQ ID NO 6
<211> LENGTH: 1460
<212> TYPE: PRT
<213> ORGANISM: Rattus norvegicus

<400> SEQUENCE: 6

Gly Gly Thr Gly Cys Ala Cys Cys Thr Cys Thr Thr Gly Gly
1               5                   10                  15

Thr Cys Ala Gly Thr Gly Ala Ala Cys Thr Thr Gly Cys Gly Cys Thr
                20                  25                  30

Gly Cys Cys Cys Cys Gly Cys Thr Gly Cys Thr Gly Cys Cys Ala Thr
                35                  40                  45

Gly Thr Gly Thr Gly Cys Gly Gly Cys Thr Cys Gly Gly Ala Cys Gly
            50                  55                  60

Cys Cys Gly Cys Ala Gly Cys Thr Gly Cys Gly Cys Thr Cys Ala
65              70                  75                  80

Thr Cys Thr Thr Cys Cys Gly Ala Gly Gly Ala Cys Thr Thr Thr
                85                  90                  95

Cys Gly Thr Cys Cys Ala Cys Thr Cys Cys Ala Cys Thr Gly Gly
            100                 105                 110

Ala Cys Cys Thr Gly Cys Cys Cys Ala Thr Gly Gly Ala Gly Gly
            115                 120                 125

Thr Gly Cys Thr Thr Cys Gly Cys Gly Ala Thr Cys Ala Cys Cys Thr
            130                 135                 140

Thr Cys Thr Thr Gly Gly Cys Gly Thr Gly Ala Gly Cys Gly Ala Cys
145                 150                 155                 160

Ala Gly Cys Gly Gly Cys Ala Ala Ala Ala Thr Ala Gly Thr Gly Thr
                165                 170                 175

Thr Thr Cys Thr Ala Gly Ala Ala Gly Ala Thr Cys Ala Thr Cys
            180                 185                 190

Thr Cys Ala Gly Cys Ala Ala Gly Ala Ala Ala Gly Cys Thr Gly
            195                 200                 205

Gly Cys Cys Ala Ala Gly Cys Ala Ala Thr Gly Gly Thr Gly Cys Thr
            210                 215                 220

Thr Cys Ala Ala Ala Cys Cys Gly Thr Gly Thr Gly Ala Gly Ala Thr
225                 230                 235                 240

Cys Ala Gly Ala Gly Ala Gly Cys Thr Gly Ala Gly Cys Cys Ala Cys
                245                 250                 255

Cys Ala Thr Gly Ala Gly Thr Thr Cys Thr Thr Cys Ala Thr Gly Cys
                260                 265                 270
```

-continued

Cys Ala Gly Gly Cys Cys Thr Thr Gly Thr Thr Gly Ala Thr Ala Cys
275 280 285

Ala Cys Ala Cys Ala Thr Cys Cys Ala Thr Gly Cys Cys Cys Cys Thr
290 295 300

Cys Ala Gly Thr Ala Thr Gly Cys Cys Thr Thr Thr Gly Cys Thr Gly
305 310 315 320

Gly Ala Ala Gly Cys Ala Ala Cys Gly Thr Cys Gly Ala Cys Cys Thr
325 330 335

Gly Cys Cys Ala Cys Thr Thr Thr Thr Gly Gly Ala Thr Thr Gly Gly
340 345 350

Cys Thr Gly Ala Ala Cys Ala Ala Gly Thr Ala Thr Ala Cys Ala Thr
355 360 365

Thr Thr Cys Cys Thr Ala Cys Ala Gly Ala Ala Ala Ala Ala Ala Gly
370 375 380

Gly Thr Thr Cys Cys Ala Gly Ala Gly Cys Ala Cys Cys Gly Ala Thr
385 390 395 400

Gly Thr Gly Gly Cys Thr Gly Ala Ala Gly Ala Ala Gly Thr Cys Thr
405 410 415

Ala Cys Ala Cys Thr Ala Gly Ala Gly Thr Cys Gly Thr Thr Ala Gly
420 425 430

Gly Ala Gly Ala Ala Cys Ala Cys Thr Ala Ala Ala Gly Ala Ala Cys
435 440 445

Gly Gly Cys Ala Cys Cys Ala Cys Cys Ala Cys Gly Gly Cys Ala Thr
450 455 460

Gly Cys Thr Ala Cys Thr Thr Thr Gly Gly Ala Ala Cys Ala Ala Thr
465 470 475 480

Thr Cys Ala Cys Ala Cys Thr Gly Ala Cys Thr Cys Ala Thr Cys Cys
485 490 495

Cys Thr Gly Ala Thr Cys Cys Thr Thr Gly Cys Gly Gly Ala Ala Ala
500 505 510

Thr Thr Ala Cys Ala Gly Ala Thr Ala Ala Ala Thr Thr Thr Gly Gly
515 520 525

Gly Cys Ala Gly Cys Gly Ala Gly Cys Ala Thr Thr Thr Gly Thr Gly
530 535 540

Gly Gly Cys Ala Ala Ala Gly Thr Ala Thr Gly Cys Ala Thr Gly Gly
545 550 555 560

Ala Thr Thr Thr Ala Ala Ala Thr Ala Ala Cys Ala Cys Thr Gly Thr
565 570 575

Thr Cys Cys Ala Gly Ala Ala Thr Ala Cys Ala Ala Gly Gly Ala Gly
580 585 590

Ala Cys Cys Ala Cys Cys Gly Ala Gly Gly Ala Gly Thr Cys Ala Gly
595 600 605

Thr Cys Ala Ala Gly Gly Ala Gly Ala Cys Ala Gly Ala Gly Ala Gly
610 615 620

Ala Thr Thr Thr Gly Thr Gly Thr Cys Ala Gly Ala Ala Ala Thr Gly
625 630 635 640

Cys Thr Thr Cys Ala Ala Ala Ala Gly Ala Ala Thr Thr Ala Thr Thr
645 650 655

Cys Ala Ala Gly Gly Gly Thr Gly Ala Ala Ala Cys Cys Cys Ala Thr
660 665 670

Ala Gly Thr Gly Ala Cys Cys Cys Cys Gly Cys Gly Ala Thr Thr Thr
675 680 685

-continued

Thr Cys Thr Cys Thr Thr Thr Cys Thr Thr Gly Cys Ala Cys Gly Gly
        690                 695                 700

Ala Gly Ala Cys Thr Cys Thr Gly Ala Thr Gly Ala Gly Thr Gly Ala
705                 710                 715                 720

Ala Cys Thr Thr Gly Gly Cys Ala Ala Cys Ala Thr Cys Gly Cys Cys
            725                 730                 735

Ala Ala Gly Ala Cys Thr Cys Ala Thr Gly Ala Thr Cys Thr Gly Thr
            740                 745                 750

Ala Cys Ala Thr Cys Cys Ala Gly Ala Gly Cys Cys Ala Thr Ala Thr
            755                 760                 765

Ala Ala Gly Thr Gly Ala Ala Ala Thr Cys Gly Thr Gly Ala Ala
770                 775                 780

Gly Ala Ala Ala Thr Thr Gly Ala Ala Gly Cys Thr Gly Thr Gly Ala
785                 790                 795                 800

Ala Ala Ala Gly Cys Thr Thr Ala Thr Cys Cys Thr Gly Gly
            805                 810                 815

Cys Thr Ala Cys Ala Ala Ala Ala Cys Thr Ala Cys Ala Cys Ala
            820                 825                 830

Gly Ala Thr Gly Thr Cys Thr Ala Thr Gly Ala Thr Ala Ala Ala
            835                 840                 845

Ala Cys Ala Ala Thr Cys Thr Thr Cys Thr Gly Ala Cys Ala Ala
            850                 855                 860

Cys Ala Ala Ala Cys Ala Gly Thr Gly Ala Thr Gly Gly Cys Thr
865                 870                 875                 880

Cys Ala Thr Gly Gly Cys Thr Gly Cys Thr Ala Cys Cys Thr Thr Thr
            885                 890                 895

Cys Thr Gly Ala Ala Gly Ala Ala Gly Ala Gly Cys Thr Gly Ala Ala
            900                 905                 910

Cys Gly Thr Cys Thr Thr Cys Ala Gly Thr Gly Ala Ala Cys Gly Ala
            915                 920                 925

Gly Gly Ala Gly Cys Ala Thr Cys Cys Ala Thr Thr Gly Cys Ala Cys
930                 935                 940

Ala Thr Thr Gly Thr Cys Cys Ala Ala Cys Thr Cys Thr Ala Ala
945                 950                 955                 960

Thr Cys Thr Gly Thr Cys Gly Cys Thr Gly Ala Gly Cys Ala Gly Thr
            965                 970                 975

Gly Gly Cys Thr Thr Ala Cys Thr Gly Ala Ala Cys Gly Thr Gly Cys
            980                 985                 990

Thr Cys Gly Ala Thr Gly Thr Cys Cys Thr Gly Ala Ala Gly Cys Ala
            995                1000                1005

Thr Ala Ala Ala Gly Thr Gly Ala Ala Gly Ala Thr Ala Gly Gly
            1010                1015                1020

Gly Cys Thr Thr Gly Gly Gly Ala Cys Ala Gly Ala Thr Gly Thr
            1025                1030                1035

Gly Gly Cys Thr Gly Gly Thr Gly Gly Thr Thr Ala Cys Thr Cys
            1040                1045                1050

Cys Thr Ala Thr Thr Cys Cys Ala Thr Gly Cys Thr Thr Gly Ala
            1055                1060                1065

Cys Gly Cys Cys Ala Thr Cys Gly Ala Ala Gly Ala Gly Cys
            1070                1075                1080

Ala Gly Thr Gly Ala Thr Gly Gly Thr Thr Thr Cys Cys Ala Ala
            1085                1090                1095

Cys Gly Thr Cys Cys Thr Cys Thr Thr Ala Ala Thr Thr Ala Ala

```
                1100                1105                1110
Thr Ala Ala Gly Gly Thr Gly Ala Ala Thr Gly Ala Gly Ala Ala
    1115                1120                1125

Ala Ala Gly Cys Cys Thr Cys Ala Cys Cys Thr Cys Ala Ala
    1130                1135            1140

Ala Gly Ala Ala Gly Thr Cys Thr Thr Cys Ala Gly Ala Cys Thr
    1145                1150                1155

Ala Gly Cys Cys Ala Cys Thr Cys Thr Thr Gly Ala Gly Gly
    1160                1165            1170

Ala Ala Gly Cys Cys Ala Ala Gly Cys Cys Thr Gly Gly Gly
    1175                1180                1185

Gly Cys Thr Thr Gly Ala Thr Cys Gly Thr Gly Ala Ala Ala Thr
    1190                1195                1200

Thr Gly Gly Ala Ala Ala Cys Thr Thr Gly Ala Gly Gly Thr
    1205                1210            1215

Cys Gly Gly Cys Ala Ala Gly Gly Ala Thr Thr Thr Gly Ala
    1220                1225            1230

Thr Gly Cys Cys Cys Thr Cys Thr Thr Gly Ala Thr Cys Ala Ala
    1235                1240                1245

Cys Cys Cys Cys Ala Gly Ala Gly Cys Ala Thr Cys Gly Gly Ala
    1250                1255            1260

Cys Thr Cys Thr Cys Cys Ala Thr Thr Gly Ala Thr Cys Thr
    1265                1270            1275

Gly Thr Thr Thr Thr Gly Thr Gly Gly Gly Gly Ala Thr Thr Thr
    1280                1285                1290

Cys Gly Thr Thr Gly Gly Thr Gly Ala Thr Ala Thr Thr Thr Cys
    1295                1300                1305

Thr Gly Ala Gly Gly Cys Thr Gly Thr Thr Ala Thr Cys Cys Ala
    1310                1315            1320

Gly Ala Ala Gly Thr Thr Cys Cys Thr Cys Thr Ala Thr Cys Thr
    1325                1330                1335

Ala Gly Gly Ala Gly Ala Thr Gly Ala Cys Cys Gly Ala Ala Ala
    1340                1345            1350

Cys Ala Thr Thr Gly Ala Gly Gly Ala Gly Gly Thr Thr Thr Ala
    1355                1360            1365

Thr Gly Thr Gly Gly Gly Thr Gly Gly Ala Ala Ala Gly Cys Ala
    1370                1375            1380

Gly Gly Thr Cys Gly Thr Thr Cys Cys Ala Thr Thr Cys Thr Cys
    1385                1390                1395

Cys Ala Gly Cys Thr Cys Cys Gly Thr Gly Thr Ala Ala Gly Gly
    1400                1405            1410

Cys Cys Cys Thr Thr Gly Gly Ala Cys Ala Thr Cys Cys Ala Thr
    1415                1420                1425

Gly Ala Cys Gly Cys Thr Cys Thr Cys Thr Gly Thr Gly Gly Ala
    1430                1435            1440

Gly Gly Ala Cys Ala Thr Gly Ala Gly Thr Cys Thr Gly Cys Thr
    1445                1450                1455

Ala Thr
    1460

<210> SEQ ID NO 7
<211> LENGTH: 454
<212> TYPE: PRT
<213> ORGANISM: Mus musculus
```

```
<400> SEQUENCE: 7

Met Cys Ala Ala Arg Thr Pro Pro Leu Ala Leu Val Phe Arg Gly Thr
1               5                   10                  15

Phe Val His Ser Thr Trp Thr Cys Pro Met Glu Val Leu Arg Asp His
            20                  25                  30

Leu Leu Gly Val Ser Asp Ser Gly Lys Ile Val Phe Leu Glu Glu Ser
        35                  40                  45

Ser Gln Gln Glu Lys Leu Ala Lys Glu Trp Cys Phe Lys Pro Cys Glu
    50                  55                  60

Ile Arg Glu Leu Ser His His Glu Phe Phe Met Pro Gly Leu Val Asp
65                  70                  75                  80

Thr His Ile His Ala Pro Gln Tyr Ala Phe Ala Gly Ser Asn Val Asp
                85                  90                  95

Leu Pro Leu Leu Glu Trp Leu Asn Lys Tyr Thr Phe Pro Thr Glu Gln
            100                 105                 110

Arg Phe Arg Ser Thr Asp Val Ala Glu Val Tyr Thr Arg Val Val
        115                 120                 125

Arg Arg Thr Leu Lys Asn Gly Thr Thr Thr Ala Cys Tyr Phe Gly Thr
    130                 135                 140

Ile His Thr Asp Ser Ser Leu Ile Leu Ala Glu Ile Thr Asp Lys Phe
145                 150                 155                 160

Gly Gln Arg Ala Phe Val Gly Lys Val Cys Met Asp Leu Asn Asp Thr
                165                 170                 175

Val Pro Glu Tyr Lys Glu Thr Thr Glu Glu Ser Val Lys Glu Thr Glu
            180                 185                 190

Arg Phe Val Ser Glu Met Leu Gln Lys Asn Tyr Pro Arg Val Lys Pro
        195                 200                 205

Ile Val Thr Pro Arg Phe Thr Leu Ser Cys Thr Glu Thr Leu Met Ser
    210                 215                 220

Glu Leu Gly Asn Ile Ala Lys Thr His Asp Leu Tyr Ile Gln Ser His
225                 230                 235                 240

Ile Ser Glu Asn Arg Glu Glu Ile Glu Ala Val Lys Ser Leu Tyr Pro
                245                 250                 255

Ser Tyr Lys Asn Tyr Thr Asp Val Tyr Asp Lys Asn Asn Leu Leu Thr
            260                 265                 270

Asn Lys Thr Val Met Ala His Gly Cys Tyr Leu Ser Glu Glu Glu Leu
        275                 280                 285

Asn Ile Phe Ser Glu Arg Gly Ala Ser Ile Ala His Cys Pro Asn Ser
    290                 295                 300

Asn Leu Ser Leu Ser Ser Gly Leu Leu Asn Val Leu Glu Val Leu Lys
305                 310                 315                 320

His Lys Val Lys Ile Gly Leu Gly Thr Asp Val Ala Gly Gly Tyr Ser
                325                 330                 335

Tyr Ser Met Leu Asp Ala Ile Arg Arg Ala Val Met Val Ser Asn Val
            340                 345                 350

Leu Leu Ile Asn Lys Val Asn Glu Lys Asn Leu Thr Leu Lys Glu Val
        355                 360                 365

Phe Arg Leu Ala Thr Leu Gly Gly Ser Gln Ala Leu Gly Leu Asp Ser
    370                 375                 380

Glu Ile Gly Asn Phe Glu Val Gly Lys Glu Phe Asp Ala Leu Leu Ile
385                 390                 395                 400

Asn Pro Arg Ala Ser Asp Ser Pro Ile Asp Leu Phe Tyr Gly Asp Phe
```

-continued

```
                    405                 410                 415
Val Gly Asp Ile Ser Glu Ala Val Ile Gln Lys Phe Leu Tyr Leu Gly
                420                 425                 430

Asp Asp Arg Asn Ile Glu Glu Val Tyr Val Gly Gly Lys Gln Val Val
            435                 440                 445

Pro Phe Ser Ser Val
        450

<210> SEQ ID NO 8
<211> LENGTH: 3241
<212> TYPE: PRT
<213> ORGANISM: Mus musculus

<400> SEQUENCE: 8

Ala Gly Ala Gly Cys Cys Ala Gly Cys Ala Gly Thr Cys Cys Cys
1               5                   10                  15

Gly Cys Thr Cys Cys Gly Cys Ala Gly Cys Cys Gly Cys Ala Gly Gly
                20                  25                  30

Ala Ala Cys Cys Gly Cys Thr Cys Thr Gly Cys Gly Cys Cys Cys Gly
                35                  40                  45

Cys Cys Cys Gly Gly Thr Gly Cys Gly Cys Cys Cys Thr Cys Cys Thr
            50                  55                  60

Thr Gly Gly Cys Cys Ala Gly Thr Gly Ala Ala Cys Thr Cys Gly Cys
65                  70                  75                  80

Gly Cys Thr Gly Cys Cys Cys Thr Gly Cys Thr Gly Cys Ala Gly Cys
                85                  90                  95

Cys Ala Thr Gly Thr Gly Thr Cys Gly Gly Cys Thr Cys Gly Gly
            100                 105                 110

Ala Cys Gly Cys Cys Gly Cys Cys Gly Cys Thr Gly Cys Gly Cys
            115                 120                 125

Thr Cys Gly Thr Cys Thr Thr Cys Cys Gly Ala Gly Gly Gly Ala Cys
            130                 135                 140

Thr Thr Thr Cys Gly Thr Cys Ala Cys Thr Cys Cys Ala Cys Cys
145                 150                 155                 160

Thr Gly Gly Ala Cys Cys Thr Gly Cys Cys Cys Ala Thr Gly Gly
                165                 170                 175

Ala Gly Gly Thr Gly Cys Thr Thr Cys Gly Cys Gly Ala Thr Cys Ala
                180                 185                 190

Cys Cys Thr Cys Cys Thr Cys Gly Gly Cys Gly Thr Gly Ala Gly Cys
            195                 200                 205

Gly Ala Cys Ala Gly Cys Gly Gly Cys Ala Ala Ala Thr Ala Gly
        210                 215                 220

Thr Gly Thr Thr Thr Cys Thr Ala Gly Ala Ala Gly Ala Ala Thr Cys
225                 230                 235                 240

Ala Thr Cys Thr Cys Ala Gly Cys Ala Ala Gly Ala Ala Ala Ala
                245                 250                 255

Cys Thr Gly Gly Cys Cys Ala Ala Gly Gly Ala Gly Thr Gly Gly Thr
                260                 265                 270

Gly Tyr Thr Thr Cys Ala Ala Ala Cys Cys Ala Thr Gly Thr Gly Ala
            275                 280                 285

Gly Ala Thr Cys Ala Gly Ala Gly Ala Ala Cys Thr Gly Ala Gly Cys
        290                 295                 300

Cys Ala Cys Cys Ala Thr Gly Ala Gly Thr Thr Cys Thr Thr Cys Ala
305                 310                 315                 320
```

-continued

```
Thr Gly Cys Cys Ala Gly Cys Cys Thr Gly Thr Gly Ala
            325             330             335

Thr Ala Cys Cys Cys Ala Cys Ala Thr Cys Cys Ala Thr Gly Cys Cys
            340             345             350

Cys Cys Thr Cys Ala Gly Thr Ala Thr Gly Cys Cys Thr Thr Gly
            355             360             365

Cys Thr Gly Gly Ala Ala Gly Cys Ala Ala Cys Gly Thr Thr Gly Ala
    370             375             380

Cys Cys Thr Gly Cys Cys Gly Cys Thr Thr Thr Gly Gly Ala Gly
385             390             395             400

Thr Gly Gly Cys Thr Gly Ala Ala Thr Ala Ala Gly Thr Ala Thr Ala
            405             410             415

Cys Ala Thr Thr Thr Cys Cys Ala Cys Ala Gly Ala Ala Cys Ala
            420             425             430

Ala Ala Gly Gly Thr Thr Cys Cys Gly Gly Ala Gly Cys Ala Cys Thr
            435             440             445

Gly Ala Thr Gly Thr Gly Gly Cys Thr Gly Ala Ala Gly Ala Ala Gly
    450             455             460

Thr Cys Thr Ala Cys Ala Cys Thr Ala Gly Ala Gly Thr Gly Thr
465             470             475             480

Thr Ala Gly Gly Ala Gly Ala Ala Cys Ala Cys Thr Gly Ala Ala Gly
            485             490             495

Ala Ala Cys Gly Gly Cys Ala Cys Cys Ala Cys Cys Ala Cys Gly Gly
            500             505             510

Cys Thr Thr Gly Cys Thr Ala Cys Thr Thr Gly Gly Ala Ala Cys
    515             520             525

Ala Ala Thr Thr Cys Ala Cys Ala Cys Thr Gly Ala Cys Thr Cys Ala
530             535             540

Thr Cys Cys Cys Thr Gly Ala Thr Cys Cys Thr Thr Gly Cys Gly Gly
545             550             555             560

Ala Ala Ala Thr Thr Ala Cys Ala Gly Ala Thr Ala Ala Ala Thr Thr
            565             570             575

Thr Gly Gly Gly Cys Ala Gly Cys Gly Ala Gly Cys Ala Thr Thr Thr
            580             585             590

Gly Thr Gly Gly Cys Ala Ala Ala Gly Thr Ala Thr Gly Cys Ala
    595             600             605

Thr Gly Gly Ala Thr Thr Gly Ala Ala Thr Gly Ala Thr Ala Cys
    610             615             620

Thr Gly Thr Thr Cys Cys Ala Gly Ala Ala Thr Ala Cys Ala Ala Gly
625             630             635             640

Gly Ala Gly Ala Cys Cys Ala Cys Cys Gly Ala Gly Gly Ala Gly Thr
            645             650             655

Cys Ala Gly Thr Cys Ala Gly Gly Ala Gly Ala Cys Ala Gly Ala
    660             665             670

Gly Ala Gly Ala Thr Thr Thr Gly Thr Gly Thr Cys Ala Gly Ala Ala
            675             680             685

Ala Thr Gly Cys Thr Gly Cys Ala Ala Ala Gly Ala Ala Thr Thr
    690             695             700

Ala Thr Cys Cys Ala Ala Gly Gly Gly Thr Gly Ala Ala Ala Cys Cys
705             710             715             720

Cys Ala Thr Ala Gly Thr Gly Ala Cys Cys Cys Ala Cys Gly Cys
            725             730             735

Thr Thr Thr Ala Cys Cys Cys Thr Thr Thr Cys Thr Thr Gly Cys Ala
```

-continued

```
                740             745             750
Cys Gly Gly Ala Gly Ala Cys Thr Cys Thr Gly Ala Thr Gly Ala Gly
        755             760             765
Thr Gly Ala Ala Cys Thr Thr Gly Gly Cys Ala Ala Cys Ala Thr Cys
        770             775             780
Gly Cys Cys Ala Ala Gly Ala Cys Cys Ala Thr Gly Ala Thr Cys
785             790             795             800
Thr Gly Thr Ala Cys Ala Thr Cys Cys Ala Gly Ala Gly Cys Cys Ala
                805             810             815
Thr Ala Thr Ala Ala Gly Thr Gly Ala Ala Ala Thr Cys Gly Thr
                820             825             830
Gly Ala Ala Gly Ala Ala Ala Thr Thr Gly Ala Ala Gly Cys Cys Gly
        835             840             845
Thr Gly Ala Ala Ala Gly Cys Thr Thr Ala Thr Ala Cys Cys Cys
        850             855             860
Thr Ala Gly Thr Thr Ala Cys Ala Ala Ala Ala Cys Thr Ala Cys
865             870             875             880
Ala Cys Ala Gly Ala Thr Gly Thr Cys Thr Ala Thr Gly Ala Thr Ala
                885             890             895
Ala Ala Ala Ala Cys Ala Ala Thr Cys Thr Cys Thr Gly Ala Cys
                900             905             910
Ala Ala Cys Ala Gly Ala Cys Ala Gly Thr Ala Ala Thr Gly
        915             920             925
Gly Cys Ala Cys Ala Thr Gly Gly Cys Thr Gly Cys Thr Ala Cys Cys
        930             935             940
Thr Thr Thr Cys Thr Gly Ala Ala Gly Ala Ala Gly Ala Ala Cys Thr
945             950             955             960
Thr Ala Ala Cys Ala Thr Cys Thr Thr Cys Ala Gly Thr Gly Ala Ala
                965             970             975
Cys Gly Ala Gly Gly Ala Gly Cys Ala Thr Cys Cys Ala Thr Thr Gly
                980             985             990
Cys Ala Cys Ala Thr Thr Gly Thr  Cys Cys Cys Ala Ala  Cys Thr Cys
                995             1000            1005
Thr Ala  Ala Thr Cys Thr Gly  Thr Cys Gly Cys Thr  Gly Ala Gly
        1010            1015            1020
Cys Ala  Gly Thr Gly Gly Cys  Thr Thr Ala Cys Thr  Gly Ala Ala
        1025            1030            1035
Cys Gly  Thr Gly Cys Thr Thr  Gly Ala Gly Gly Thr  Cys Cys Thr
        1040            1045            1050
Gly Ala  Ala Gly Cys Ala Thr  Ala Ala Ala Gly Thr  Gly Ala Ala
        1055            1060            1065
Gly Ala  Thr Ala Gly Gly Gly  Cys Thr Gly Gly Gly  Gly Ala Cys
        1070            1075            1080
Ala Gly  Ala Thr Gly Thr Gly  Gly Cys Thr Gly Gly  Thr Gly Gly
        1085            1090            1095
Cys Thr  Ala Cys Thr Cys Cys  Thr Ala Thr Thr Cys  Cys Ala Thr
        1100            1105            1110
Gly Cys  Thr Thr Gly Ala Thr  Gly Cys Cys Ala Thr  Cys Ala Gly
        1115            1120            1125
Ala Ala  Gly Ala Gly Cys Ala  Gly Thr Cys Ala Thr  Gly Gly Thr
        1130            1135            1140
Thr Thr  Cys Cys Ala Ala Thr  Gly Thr Cys Cys Thr  Cys Thr Thr
        1145            1150            1155
```

```
Ala Ala Thr Thr Ala Ala Thr Ala Ala Gly Gly Thr Ala Ala Ala
    1160            1165            1170

Thr Gly Ala Gly Ala Ala Ala Ala Ala Cys Cys Thr Cys Ala Cys
    1175            1180            1185

Cys Cys Thr Cys Ala Ala Ala Gly Ala Ala Gly Thr Cys Thr Thr
    1190            1195            1200

Cys Ala Gly Ala Cys Thr Ala Gly Cys Cys Ala Cys Thr Cys Thr
    1205            1210            1215

Thr Gly Gly Ala Gly Gly Ala Ala Gly Cys Cys Ala Ala Gly Cys
    1220            1225            1230

Cys Cys Thr Gly Gly Gly Gly Cys Thr Thr Gly Ala Thr Ala Gly
    1235            1240            1245

Cys Gly Ala Gly Ala Thr Thr Gly Gly Ala Ala Ala Cys Thr Thr
    1250            1255            1260

Thr Gly Ala Ala Gly Thr Thr Gly Gly Cys Ala Ala Gly Gly Ala
    1265            1270            1275

Ala Thr Thr Thr Gly Ala Thr Gly Cys Cys Cys Thr Cys Thr Thr
    1280            1285            1290

Gly Ala Thr Cys Ala Ala Cys Cys Cys Cys Ala Gly Ala Gly Cys
    1295            1300            1305

Ala Thr Cys Ala Gly Ala Cys Thr Cys Thr Cys Cys Cys Ala Thr
    1310            1315            1320

Thr Gly Ala Thr Cys Thr Gly Thr Thr Thr Thr Ala Thr Gly Gly
    1325            1330            1335

Gly Gly Ala Thr Thr Thr Thr Gly Thr Thr Gly Gly Thr Gly Ala
    1340            1345            1350

Thr Ala Thr Thr Thr Cys Thr Gly Ala Gly Gly Cys Thr Gly Thr
    1355            1360            1365

Thr Ala Thr Cys Cys Ala Gly Ala Ala Gly Thr Thr Thr Cys Thr
    1370            1375            1380

Thr Thr Ala Thr Cys Thr Ala Gly Gly Ala Gly Ala Cys Gly Ala
    1385            1390            1395

Cys Cys Gly Ala Ala Ala Thr Ala Thr Gly Ala Gly Gly Ala
    1400            1405            1410

Gly Gly Thr Thr Thr Ala Thr Gly Thr Gly Gly Thr Gly Gly
    1415            1420            1425

Ala Ala Ala Gly Cys Ala Gly Gly Thr Cys Gly Thr Cys Cys
    1430            1435            1440

Ala Thr Thr Cys Thr Cys Cys Ala Gly Cys Thr Cys Ala Gly Thr
    1445            1450            1455

Gly Thr Ala Ala Gly Gly Ala Cys Cys Thr Thr Gly Gly Ala Cys
    1460            1465            1470

Ala Thr Cys Thr Gly Cys Gly Ala Cys Ala Thr Thr Cys Thr Cys
    1475            1480            1485

Cys Thr Gly Gly Gly Ala Ala Gly Ala Cys Ala Thr Gly Ala Thr
    1490            1495            1500

Thr Cys Cys Gly Cys Cys Ala Thr Cys Thr Thr Cys Cys Thr Thr
    1505            1510            1515

Gly Thr Gly Cys Cys Cys Ala Gly Gly Gly Ala Cys Cys Ala Ala
    1520            1525            1530

Thr Cys Ala Gly Ala Ala Ala Gly Thr Ala Thr Ala Thr Thr Thr
    1535            1540            1545
```

```
Ala Cys Ala Ala Ala Ala Ala Gly Thr Ala Cys Cys Gly Thr
    1550                1555                1560

Gly Thr Thr Cys Thr Thr Thr Gly Gly Ala Thr Gly Ala Cys Thr
    1565                1570                1575

Thr Cys Thr Gly Thr Thr Cys Cys Thr Gly Thr Gly Thr Cys Thr
    1580                1585                1590

Cys Cys Thr Thr Cys Cys Ala Gly Thr Gly Cys Cys Cys Ala Cys
    1595                1600                1605

Thr Thr Gly Gly Thr Ala Ala Ala Thr Gly Thr Thr Thr Gly
    1610                1615                1620

Ala Ala Gly Gly Gly Ala Gly Thr Gly Cys Gly Cys Thr Gly Cys
    1625                1630                1635

Thr Thr Cys Thr Cys Cys Ala Cys Thr Cys Cys Ala Gly Thr Cys
    1640                1645                1650

Thr Gly Gly Gly Ala Gly Cys Ala Thr Gly Thr Ala Ala Thr
    1655                1660                1665

Thr Thr Cys Ala Thr Gly Ala Cys Ala Gly Thr Gly Cys Cys Thr
    1670                1675                1680

Cys Cys Cys Ala Thr Thr Gly Gly Gly Cys Thr Gly Thr Thr Thr
    1685                1690                1695

Ala Gly Ala Thr Thr Thr Gly Cys Ala Thr Thr Gly Thr Gly Cys
    1700                1705                1710

Thr Cys Gly Cys Ala Cys Ala Gly Ala Ala Gly Ala Cys Ala Thr
    1715                1720                1725

Thr Gly Thr Thr Ala Ala Cys Ala Gly Cys Thr Gly Gly Cys Ala
    1730                1735                1740

Ala Thr Gly Cys Gly Cys Thr Thr Cys Cys Ala Ala Thr Ala Gly
    1745                1750                1755

Thr Gly Ala Ala Gly Thr Ala Ala Ala Ala Cys Gly Thr Thr Thr
    1760                1765                1770

Cys Cys Ala Thr Ala Thr Ala Gly Gly Gly Ala Ala Ala Thr Ala
    1775                1780                1785

Cys Ala Gly Gly Ala Cys Gly Ala Gly Gly Ala Gly Ala Thr Cys
    1790                1795                1800

Thr Cys Cys Cys Thr Ala Thr Gly Thr Gly Gly Cys Thr Ala Gly
    1805                1810                1815

Ala Cys Ala Cys Thr Cys Thr Gly Thr Gly Cys Thr Ala Ala Thr
    1820                1825                1830

Gly Ala Cys Thr Ala Ala Gly Ala Ala Ala Ala Thr Ala Ala Gly
    1835                1840                1845

Gly Ala Ala Ala Cys Thr Cys Cys Ala Gly Thr Ala Thr Gly Gly
    1850                1855                1860

Ala Cys Cys Ala Ala Thr Gly Ala Gly Cys Ala Gly Ala Thr Thr
    1865                1870                1875

Thr Thr Thr Ala Thr Gly Ala Gly Ala Gly Gly Gly Cys Ala Cys
    1880                1885                1890

Ala Ala Gly Cys Thr Ala Gly Ala Cys Ala Thr Thr Gly Ala Ala
    1895                1900                1905

Ala Ala Gly Ala Cys Ala Thr Thr Gly Gly Ala Ala Ala Ala Gly
    1910                1915                1920

Thr Cys Ala Thr Thr Gly Gly Thr Thr Gly Thr Gly Cys Thr Thr
    1925                1930                1935

Gly Gly Ala Ala Ala Thr Thr Thr Ala Ala Thr Ala Thr Ala Gly
```

-continued

```
                    1940                1945                1950
Ala Gly  Ala Ala Cys Ala Gly  Thr Cys Thr Cys Gly  Thr Ala Ala
    1955                1960                1965
Ala Ala  Gly Gly Ala Gly Ala  Ala Cys Cys Thr Ala  Cys Thr Gly
    1970                1975                1980
Gly Ala  Thr Thr Thr Ala Ala  Ala Ala Cys Ala Thr  Gly Cys Thr
    1985                1990                1995
Thr Cys  Thr Ala Gly Ala Thr  Cys Gly Ala Cys Ala  Thr Thr Gly
    2000                2005                2010
Thr Cys  Thr Ala Thr Gly Gly  Ala Cys Ala Thr Thr  Thr Gly Cys
    2015                2020                2025
Ala Cys  Thr Thr Thr Gly Thr  Gly Ala Ala Ala Thr  Thr Thr Gly
    2030                2035                2040
Cys Ala  Thr Thr Thr Cys Ala  Gly Gly Ala Thr Gly  Thr Gly Thr
    2045                2050                2055
Thr Ala  Thr Thr Gly Thr Thr  Ala Thr Gly Cys Thr  Thr Thr Cys
    2060                2065                2070
Cys Cys  Thr Thr Cys Thr Thr  Gly Gly Gly Ala Thr  Gly Ala Ala
    2075                2080                2085
Thr Gly  Thr Cys Ala Gly Ala  Ala Cys Cys Thr Gly  Ala Ala Thr
    2090                2095                2100
Gly Cys  Cys Ala Cys Ala Cys  Gly Cys Thr Thr Thr  Thr Cys Ala
    2105                2110                2115
Ala Ala  Thr Ala Thr Ala Gly  Thr Thr Cys Thr Ala  Thr Gly Cys
    2120                2125                2130
Thr Thr  Cys Ala Ala Ala Gly  Thr Gly Thr Thr Cys  Gly Gly Cys
    2135                2140                2145
Ala Gly  Ala Ala Gly Thr Thr  Gly Ala Gly Thr Ala  Thr Thr Ala
    2150                2155                2160
Ala Ala  Gly Ala Thr Thr Thr  Ala Ala Ala Gly Thr  Cys Thr Cys
    2165                2170                2175
Thr Thr  Ala Gly Gly Gly Ala  Thr Ala Gly Thr Ala  Thr Thr Cys
    2180                2185                2190
Ala Cys  Ala Thr Ala Gly Cys  Cys Gly Cys Ala Ala  Gly Gly Cys
    2195                2200                2205
Ala Thr  Ala Ala Ala Thr Ala  Gly Thr Thr Gly Thr  Gly Thr Thr
    2210                2215                2220
Thr Thr  Thr Thr Thr Gly Thr  Gly Thr Gly Thr Gly  Thr Gly Thr
    2225                2230                2235
Gly Thr  Ala Cys Thr Cys Thr  Ala Ala Ala Gly Thr  Cys Ala Thr
    2240                2245                2250
Cys Thr  Thr Gly Ala Thr Thr  Cys Cys Thr Gly Gly  Cys Thr Gly
    2255                2260                2265
Thr Gly  Ala Gly Gly Thr Gly  Thr Thr Cys Cys Ala  Gly Thr Thr
    2270                2275                2280
Gly Cys  Thr Thr Cys Thr Gly  Thr Thr Thr Thr Ala  Thr Thr Ala
    2285                2290                2295
Gly Ala  Thr Gly Ala Gly Ala  Ala Ala Cys Ala Ala  Gly Cys Cys
    2300                2305                2310
Cys Thr  Gly Thr Gly Thr Gly  Thr Thr Gly Cys Thr  Gly Cys Thr
    2315                2320                2325
Cys Thr  Gly Thr Ala Gly Ala  Cys Thr Gly Gly Ala  Gly Thr Thr
    2330                2335                2340
```

-continued

Thr Thr Cys Ala Thr Ala Ala Ala Thr Cys Gly Gly Gly Gly Ala
2345 2350 2355

Ala Gly Thr Ala Cys Thr Ala Thr Ala Thr Thr Cys Cys Cys Cys
2360 2365 2370

Gly Gly Ala Gly Thr Thr Gly Gly Thr Gly Ala Cys Ala Cys Thr
2375 2380 2385

Gly Ala Gly Gly Gly Gly Ala Cys Ala Gly Gly Gly Thr Thr Cys
2390 2395 2400

Thr Thr Thr Gly Cys Ala Ala Thr Gly Cys Thr Gly Ala Ala Thr
2405 2410 2415

Cys Thr Ala Cys Cys Cys Ala Ala Cys Gly Cys Ala Thr Ala Ala
2420 2425 2430

Thr Cys Ala Thr Thr Gly Cys Thr Gly Thr Ala Cys Ala Gly Thr
2435 2440 2445

Thr Cys Ala Cys Cys Cys Thr Cys Cys Thr Ala Thr Cys Ala Ala
2450 2455 2460

Thr Gly Thr Gly Cys Thr Ala Gly Ala Ala Cys Thr Thr Ala Ala
2465 2470 2475

Ala Ala Gly Cys Cys Ala Ala Gly Thr Gly Cys Ala Ala Gly Thr
2480 2485 2490

Cys Cys Cys Thr Ala Ala Ala Gly Cys Ala Thr Thr Ala Thr Gly
2495 2500 2505

Gly Ala Thr Ala Ala Gly Gly Cys Thr Cys Thr Gly Cys Ala Ala
2510 2515 2520

Gly Gly Cys Cys Ala Gly Thr Ala Thr Ala Cys Thr Gly Ala Ala
2525 2530 2535

Ala Gly Ala Gly Cys Thr Cys Thr Gly Thr Gly Thr Gly Thr Gly
2540 2545 2550

Thr Thr Thr Gly Thr Thr Thr Gly Thr Thr Thr Gly Thr Thr Cys
2555 2560 2565

Gly Thr Thr Thr Gly Thr Thr Thr Thr Ala Ala Thr Thr Thr Ala
2570 2575 2580

Cys Cys Ala Ala Ala Thr Thr Gly Thr Cys Ala Thr Thr Gly Thr
2585 2590 2595

Ala Ala Thr Thr Cys Thr Thr Gly Ala Ala Gly Ala Thr Thr Thr
2600 2605 2610

Thr Thr Cys Thr Gly Gly Cys Ala Thr Thr Ala Ala Ala Ala Thr
2615 2620 2625

Cys Thr Thr Ala Gly Ala Ala Thr Ala Gly Thr Gly Ala Ala Ala
2630 2635 2640

Ala Gly Gly Ala Thr Ala Thr Ala Ala Ala Ala Ala Thr Thr Cys
2645 2650 2655

Cys Ala Thr Cys Thr Ala Ala Thr Gly Thr Thr Thr Ala Thr Ala
2660 2665 2670

Thr Thr Thr Cys Thr Ala Gly Gly Ala Cys Thr Thr Ala Cys Cys
2675 2680 2685

Thr Gly Thr Ala Cys Thr Ala Gly Ala Cys Ala Thr Cys Ala Ala
2690 2695 2700

Gly Gly Ala Ala Thr Ala Thr Thr Ala Ala Ala Cys Ala Ala Ala
2705 2710 2715

Ala Gly Ala Gly Gly Gly Cys Cys Thr Thr Thr Thr Ala Gly Cys
2720 2725 2730

-continued

```
Thr Thr Thr Thr Cys Thr Ala Ala Cys Gly Thr Ala Thr Ala Thr
    2735            2740            2745
Gly Gly Thr Gly Thr Cys Cys Cys Thr Cys Thr Cys Ala Thr
    2750            2755            2760
Ala Thr Thr Ala Gly Ala Ala Cys Thr Ala Ala Ala Ala Cys Cys
    2765            2770            2775
Ala Gly Gly Thr Cys Ala Thr Ala Ala Cys Cys Ala Cys Gly Thr
    2780            2785            2790
Gly Gly Cys Ala Gly Ala Gly Cys Thr Thr Ala Gly Gly Ala
    2795            2800            2805
Ala Ala Cys Ala Gly Thr Gly Ala Thr Gly Thr Gly Thr Ala Thr
    2810            2815            2820
Thr Cys Thr Ala Cys Thr Thr Ala Ala Ala Thr Ala Cys Thr Ala
    2825            2830            2835
Cys Ala Thr Thr Thr Thr Thr Cys Thr Thr Ala Ala Thr Thr Ala
    2840            2845            2850
Ala Thr Thr Cys Cys Ala Cys Cys Thr Cys Cys Thr Ala Thr Ala
    2855            2860            2865
Ala Ala Cys Ala Ala Gly Cys Ala Ala Gly Gly Gly Cys Cys Ala
    2870            2875            2880
Gly Gly Ala Ala Cys Ala Gly Gly Thr Thr Thr Thr Ala Thr Thr
    2885            2890            2895
Ala Ala Cys Ala Thr Ala Thr Ala Thr Thr Thr Cys Ala Cys Thr
    2900            2905            2910
Cys Cys Thr Ala Gly Gly Gly Thr Thr Thr Ala Gly Gly Thr Gly
    2915            2920            2925
Ala Gly Thr Thr Thr Cys Cys Ala Thr Thr Gly Thr Ala Thr Cys
    2930            2935            2940
Thr Thr Ala Thr Ala Ala Cys Ala Gly Ala Gly Ala Ala Ala Cys
    2945            2950            2955
Cys Cys Ala Thr Thr Ala Gly Gly Cys Ala Gly Thr Ala Gly Thr
    2960            2965            2970
Thr Ala Gly Thr Thr Cys Thr Cys Ala Cys Ala Thr Cys Thr Ala
    2975            2980            2985
Ala Gly Ala Ala Cys Ala Cys Ala Cys Ala Gly Thr Thr Cys Thr
    2990            2995            3000
Thr Cys Thr Gly Thr Thr Cys Thr Cys Thr Ala Thr Gly Cys Thr
    3005            3010            3015
Ala Ala Cys Thr Cys Ala Gly Cys Ala Gly Thr Ala Ala Cys Thr
    3020            3025            3030
Thr Gly Thr Cys Cys Ala Gly Ala Thr Cys Thr Ala Thr Thr Thr
    3035            3040            3045
Thr Cys Cys Thr Gly Gly Thr Ala Gly Ala Ala Gly Cys Ala Cys
    3050            3055            3060
Thr Thr Thr Thr Ala Gly Ala Thr Cys Thr Gly Gly Thr Gly Thr
    3065            3070            3075
Gly Thr Ala Thr Ala Cys Ala Thr Thr Ala Thr Ala Thr Cys Thr
    3080            3085            3090
Cys Ala Ala Gly Ala Thr Gly Gly Thr Ala Cys Ala Cys Ala Thr
    3095            3100            3105
Thr Thr Ala Gly Gly Thr Cys Gly Thr Ala Cys Thr Thr Thr Gly
    3110            3115            3120
Thr Thr Thr Thr Ala Thr Thr Thr Thr Gly Ala Gly Ala Ala Ala
```

-continued

```
                    3125                3130                3135

Gly Ala  Ala Ala Gly Ala Ala  Ala Gly Ala Ala Ala  Gly Ala Ala
         3140                3145                3150

Ala Gly  Ala Ala Ala Gly Ala  Ala Ala Gly Ala Ala  Ala Gly Ala
3155                3160                3165

Ala Ala  Gly Ala Ala Ala Gly  Ala Ala Ala Gly Ala  Ala Ala Gly
     3170                3175                3180

Ala Ala  Ala Gly Ala Ala Ala  Gly Ala Ala Ala Ala  Ala Gly Ala
         3185                3190                3195

Ala Ala  Gly Gly Ala Ala Gly  Gly Ala Ala Gly Gly  Ala Ala Gly
3200                3205                3210

Gly Ala  Ala Gly Gly Ala Ala  Gly Ala Ala Ala Gly  Ala Ala Ala
     3215                3220                3225

Gly Ala  Ala Ala Gly Ala Ala  Ala Gly Ala Ala Ala  Gly
         3230                3235                3240

<210> SEQ ID NO 9
<211> LENGTH: 445
<212> TYPE: PRT
<213> ORGANISM: Homo sapiens

<400> SEQUENCE: 9

Met Cys Ala Ala Gln Met Pro Pro Leu Ala His Ile Phe Arg Gly Thr
1               5                   10                  15

Phe Val His Ser Thr Trp Thr Cys Pro Met Glu Val Leu Arg Asp His
                20                  25                  30

Leu Leu Gly Val Ser Asp Ser Gly Lys Ile Val Phe Leu Glu Glu Ala
            35                  40                  45

Ser Gln Gln Glu Lys Leu Ala Lys Glu Trp Cys Phe Lys Pro Cys Glu
        50                  55                  60

Ile Arg Glu Leu Ser His His Glu Phe Met Ala Ser Gln Tyr Ser
65                  70                  75                  80

Phe Ala Gly Ser Ser Ile Asp Leu Pro Leu Leu Glu Trp Leu Thr Lys
                85                  90                  95

Tyr Thr Phe Pro Ala Glu His Arg Phe Gln Asn Ile Asp Phe Ala Glu
            100                 105                 110

Glu Val Tyr Thr Arg Val Arg Arg Thr Leu Lys Asn Gly Thr Thr
        115                 120                 125

Thr Ala Cys Tyr Phe Ala Thr Ile His Thr Asp Ser Ser Leu Leu Leu
130                 135                 140

Ala Asp Ile Thr Asp Lys Phe Gly Gln Arg Ala Phe Val Gly Lys Val
145                 150                 155                 160

Cys Met Asp Leu Asn Asp Thr Phe Pro Glu Tyr Lys Glu Thr Thr Glu
                165                 170                 175

Glu Ser Ile Lys Glu Thr Glu Arg Phe Val Ser Glu Met Leu Gln Lys
            180                 185                 190

Asn Tyr Ser Arg Val Lys Pro Ile Val Thr Pro Arg Phe Ser Leu Ser
        195                 200                 205

Cys Ser Glu Thr Leu Met Gly Glu Leu Gly Asn Ile Ala Lys Thr Arg
210                 215                 220

Asp Leu His Ile Gln Ser His Ile Ser Glu Asn Arg Asp Glu Val
225                 230                 235                 240

Ala Val Lys Asn Leu Tyr Pro Ser Tyr Lys Asn Tyr Thr Ser Val Tyr
                245                 250                 255
```

-continued

Asp Lys Asn Asn Leu Leu Thr Asn Lys Thr Val Met Ala His Gly Cys
            260                 265                 270

Tyr Leu Ser Ala Glu Glu Leu Asn Val Phe His Glu Arg Gly Ala Ser
        275                 280                 285

Ile Ala His Cys Pro Asn Ser Asn Leu Ser Leu Ser Ser Gly Phe Leu
    290                 295                 300

Asn Val Leu Glu Val Leu Lys His Glu Val Lys Ile Gly Leu Gly Thr
305                 310                 315                 320

Asp Val Ala Gly Gly Tyr Ser Tyr Ser Met Leu Asp Ala Ile Arg Arg
                325                 330                 335

Ala Val Met Val Ser Asn Ile Leu Leu Ile Asn Lys Val Asn Glu Lys
            340                 345                 350

Ser Leu Thr Leu Lys Glu Val Phe Arg Leu Ala Thr Leu Gly Gly Ser
        355                 360                 365

Gln Ala Leu Gly Leu Asp Gly Glu Ile Gly Asn Phe Glu Val Gly Lys
    370                 375                 380

Glu Phe Asp Ala Ile Leu Ile Asn Pro Lys Ala Ser Asp Ser Pro Ile
385                 390                 395                 400

Asp Leu Phe Tyr Gly Asp Phe Gly Asp Ile Ser Glu Ala Val Ile
                405                 410                 415

Gln Lys Phe Leu Tyr Leu Gly Asp Asp Arg Asn Ile Glu Glu Val Tyr
            420                 425                 430

Val Gly Gly Lys Gln Val Val Pro Phe Ser Ser Ser Val
        435                 440                 445

<210> SEQ ID NO 10
<211> LENGTH: 445
<212> TYPE: PRT
<213> ORGANISM: Pongo pygmaeus

<400> SEQUENCE: 10

Met Cys Ala Ala Gln Met Pro Pro Leu Ala His Ile Phe Arg Gly Thr
1               5                   10                  15

Phe Val His Ser Thr Trp Thr Cys Pro Met Glu Val Leu Arg Asp His
            20                  25                  30

Leu Leu Gly Val Ser Asp Ser Gly Lys Ile Val Phe Leu Glu Glu Ala
        35                  40                  45

Ser Gln Gln Glu Lys Leu Ala Lys Glu Trp Cys Phe Lys Pro Cys Glu
    50                  55                  60

Ile Arg Glu Leu Ser His His Gly Phe Phe Met Ala Ser Gln Tyr Ser
65                  70                  75                  80

Phe Ala Gly Ser Asn Ile Asp Leu Pro Leu Leu Glu Trp Leu Thr Lys
                85                  90                  95

Tyr Thr Phe Pro Ala Glu His Arg Phe Gln Asn Thr Asp Phe Ala Glu
            100                 105                 110

Glu Val Tyr Thr Arg Val Val Arg Thr Leu Lys Asn Gly Thr Thr
        115                 120                 125

Thr Ala Cys Tyr Phe Ala Thr Ile His Thr Asp Ser Ser Leu Leu Leu
    130                 135                 140

Ala Asp Ile Thr Asp Lys Phe Gly Gln Arg Ala Phe Val Gly Lys Val
145                 150                 155                 160

Cys Met Asn Leu Asn Asp Thr Phe Pro Glu Tyr Asn Glu Thr Thr Glu
                165                 170                 175

Glu Ser Ile Lys Glu Thr Glu Arg Phe Val Ser Glu Met Leu Gln Arg
            180                 185                 190

```
Lys Tyr Ser Arg Val Lys Pro Ile Val Thr Pro Arg Phe Ser Leu Ser
            195                 200                 205
Cys Ser Glu Thr Leu Met Gly Asp Leu Gly Asn Ile Ala Lys Thr His
            210                 215                 220
Asp Leu His Ile Gln Ser His Ile Ser Glu Asn Arg Asp Glu Val Glu
225                 230                 235                 240
Ala Val Lys Asn Leu Tyr Pro Ser Tyr Lys Asn Tyr Thr Asp Val Tyr
            245                 250                 255
Asp Lys Asn Asn Leu Leu Thr Asn Lys Thr Val Met Ala His Gly Cys
            260                 265                 270
Tyr Leu Ser Ala Glu Glu Leu Asn Val Phe His Glu Arg Gly Ala Ser
            275                 280                 285
Ile Ala His Cys Pro Asn Ser Asn Leu Ser Leu Ser Ser Gly Phe Leu
            290                 295                 300
Asn Val Leu Glu Val Leu Lys His Glu Val Lys Ile Gly Leu Gly Thr
305                 310                 315                 320
Asp Val Ala Gly Gly Tyr Ser Tyr Ser Met Leu Asp Ala Ile Arg Arg
            325                 330                 335
Ala Val Met Val Ser Asn Ile Leu Leu Ile Asn Lys Val Asn Glu Lys
            340                 345                 350
Ser Leu Thr Leu Lys Glu Val Phe Arg Leu Ala Thr Leu Gly Gly Ser
            355                 360                 365
Gln Ala Leu Gly Leu Asp Gly Glu Ile Gly Asn Phe Glu Val Gly Lys
            370                 375                 380
Glu Phe Asp Ala Ile Leu Ile Asn Pro Lys Ala Ser Asp Ser Pro Ile
385                 390                 395                 400
Asp Leu Phe Tyr Gly Asp Phe Phe Gly Asp Ile Ser Glu Ala Val Ile
            405                 410                 415
Gln Lys Phe Leu Tyr Leu Gly Asp Asp Arg Asn Ile Glu Glu Val Tyr
            420                 425                 430
Val Gly Gly Lys Gln Val Val Pro Phe Ser Ser Ser Val
            435                 440                 445

<210> SEQ ID NO 11
<211> LENGTH: 445
<212> TYPE: PRT
<213> ORGANISM: Rattus norvegicus

<400> SEQUENCE: 11

Met Cys Ala Ala Arg Thr Pro Gln Leu Ala Leu Ile Phe Arg Gly Thr
1               5                   10                  15
Phe Val His Ser Thr Trp Thr Cys Pro Met Glu Val Leu Arg Asp His
            20                  25                  30
Leu Leu Gly Val Ser Asp Ser Gly Lys Ile Val Phe Leu Glu Glu Ser
            35                  40                  45
Ser Gln Gln Glu Lys Leu Ala Lys Glu Trp Cys Phe Lys Pro Cys Glu
        50                  55                  60
Ile Arg Glu Leu Ser His His Glu Phe Phe Met Ala Pro Gln Tyr Ala
65                  70                  75                  80
Phe Ala Gly Ser Asn Val Asp Leu Pro Leu Leu Asp Trp Leu Asn Lys
            85                  90                  95
Tyr Thr Phe Pro Thr Glu Lys Arg Phe Gln Ser Thr Asp Val Ala Glu
            100                 105                 110
Glu Val Tyr Thr Arg Val Val Arg Arg Thr Leu Lys Asn Gly Thr Thr
```

-continued

```
            115                 120                 125
Thr Ala Cys Tyr Phe Gly Thr Ile His Thr Asp Ser Leu Ile Leu
        130                 135                 140

Ala Glu Ile Thr Asp Lys Phe Gly Gln Arg Ala Phe Val Gly Lys Val
145                 150                 155                 160

Cys Met Asp Leu Asn Asn Thr Val Pro Glu Tyr Lys Glu Thr Thr Glu
                165                 170                 175

Glu Ser Val Lys Glu Thr Glu Arg Phe Val Ser Glu Met Leu Gln Lys
                180                 185                 190

Asn Tyr Ser Arg Val Lys Pro Ile Val Thr Pro Arg Phe Ser Leu Ser
                195                 200                 205

Cys Thr Glu Thr Leu Met Ser Glu Leu Gly Asn Ile Ala Lys Thr His
        210                 215                 220

Asp Leu Tyr Ile Gln Ser His Ile Ser Glu Asn Arg Glu Ile Glu
225                 230                 235                 240

Ala Val Lys Ser Leu Tyr Pro Gly Tyr Lys Asn Tyr Thr Asp Val Tyr
                245                 250                 255

Asp Lys Asn Asn Leu Leu Thr Asn Lys Thr Val Met Ala His Gly Cys
                260                 265                 270

Tyr Leu Ser Glu Glu Leu Asn Val Phe Ser Glu Arg Gly Ala Ser
        275                 280                 285

Ile Ala His Cys Pro Asn Ser Asn Leu Ser Leu Ser Ser Gly Leu Leu
        290                 295                 300

Asn Val Leu Asp Val Leu Lys His Lys Val Lys Ile Gly Leu Gly Thr
305                 310                 315                 320

Asp Val Ala Gly Gly Tyr Ser Tyr Ser Met Leu Asp Ala Ile Arg Arg
                325                 330                 335

Ala Val Met Val Ser Asn Val Leu Leu Ile Asn Lys Val Asn Glu Lys
                340                 345                 350

Ser Leu Thr Leu Lys Glu Val Phe Arg Leu Ala Thr Leu Gly Gly Ser
        355                 360                 365

Gln Ala Leu Gly Leu Asp Arg Glu Ile Gly Asn Phe Glu Val Gly Lys
        370                 375                 380

Asp Phe Asp Ala Leu Leu Ile Asn Pro Arg Ala Ser Asp Ser Pro Ile
385                 390                 395                 400

Asp Leu Phe Cys Gly Asp Phe Val Gly Asp Ile Ser Glu Ala Val Ile
                405                 410                 415

Gln Lys Phe Leu Tyr Leu Gly Asp Asp Arg Asn Ile Glu Glu Val Tyr
                420                 425                 430

Val Gly Gly Lys Gln Val Val Pro Phe Ser Ser Ser Val
        435                 440                 445

<210> SEQ ID NO 12
<211> LENGTH: 445
<212> TYPE: PRT
<213> ORGANISM: Mus musculus

<400> SEQUENCE: 12

Met Cys Ala Ala Arg Thr Pro Pro Leu Ala Leu Val Phe Arg Gly Thr
1               5                   10                  15

Phe Val His Ser Thr Trp Thr Cys Pro Met Glu Val Leu Arg Asp His
                20                  25                  30

Leu Leu Gly Val Ser Asp Ser Gly Lys Ile Val Phe Leu Glu Glu Ser
        35                  40                  45
```

```
Ser Gln Gln Glu Lys Leu Ala Lys Glu Trp Cys Phe Lys Pro Cys Glu
    50                  55                  60

Ile Arg Glu Leu Ser His His Glu Phe Phe Met Ala Pro Gln Tyr Ala
65                  70                  75                  80

Phe Ala Gly Ser Asn Val Asp Leu Pro Leu Leu Glu Trp Leu Asn Lys
                85                  90                  95

Tyr Thr Phe Pro Thr Glu Gln Arg Phe Arg Ser Thr Asp Val Ala Glu
            100                 105                 110

Glu Val Tyr Thr Arg Val Val Arg Arg Thr Leu Lys Asn Gly Thr Thr
        115                 120                 125

Thr Ala Cys Tyr Phe Gly Thr Ile His Thr Asp Ser Ser Leu Ile Leu
130                 135                 140

Ala Glu Ile Thr Asp Lys Phe Gly Gln Arg Ala Phe Val Gly Lys Val
145                 150                 155                 160

Cys Met Asp Leu Asn Asp Thr Val Pro Glu Tyr Lys Glu Thr Thr Glu
                165                 170                 175

Glu Ser Val Lys Glu Thr Glu Arg Phe Val Ser Glu Met Leu Gln Lys
            180                 185                 190

Asn Tyr Pro Arg Val Lys Pro Ile Val Thr Pro Arg Phe Thr Leu Ser
        195                 200                 205

Cys Thr Glu Thr Leu Met Ser Glu Leu Gly Asn Ile Ala Lys Thr His
210                 215                 220

Asp Leu Tyr Ile Gln Ser His Ile Ser Glu Asn Arg Glu Glu Ile Glu
225                 230                 235                 240

Ala Val Lys Ser Leu Tyr Pro Ser Tyr Lys Asn Tyr Thr Asp Val Tyr
                245                 250                 255

Asp Lys Asn Asn Leu Leu Thr Asn Lys Thr Val Met Ala His Gly Cys
            260                 265                 270

Tyr Leu Ser Glu Glu Leu Asn Ile Phe Ser Glu Arg Gly Ala Ser
        275                 280                 285

Ile Ala His Cys Pro Asn Ser Asn Leu Ser Leu Ser Ser Gly Leu Leu
290                 295                 300

Asn Val Leu Glu Val Leu Lys His Lys Val Lys Ile Gly Leu Gly Thr
305                 310                 315                 320

Asp Val Ala Gly Gly Tyr Ser Tyr Ser Met Leu Asp Ala Ile Arg Arg
                325                 330                 335

Ala Val Met Val Ser Asn Val Leu Leu Ile Asn Lys Val Asn Glu Lys
            340                 345                 350

Asn Leu Thr Leu Lys Glu Val Phe Arg Leu Ala Thr Leu Gly Gly Ser
        355                 360                 365

Gln Ala Leu Gly Leu Asp Ser Glu Ile Gly Asn Phe Glu Val Gly Lys
370                 375                 380

Glu Phe Asp Ala Leu Leu Ile Asn Pro Arg Ala Ser Asp Ser Pro Ile
385                 390                 395                 400

Asp Leu Phe Tyr Gly Asp Phe Val Gly Asp Ile Ser Glu Ala Val Ile
                405                 410                 415

Gln Lys Phe Leu Tyr Leu Gly Asp Asp Arg Asn Ile Glu Glu Val Tyr
            420                 425                 430

Val Gly Gly Lys Gln Val Val Pro Phe Ser Ser Ser Val
        435                 440                 445

<210> SEQ ID NO 13
<211> LENGTH: 436
<212> TYPE: PRT
```

<213> ORGANISM: Homo sapiens

<400> SEQUENCE: 13

```
Met Cys Ala Ala Gln Met Pro Pro Leu Ala His Ile Phe Arg Gly Thr
1               5                   10                  15
Phe Val His Ser Thr Trp Thr Cys Pro Met Glu Val Leu Arg Asp His
                20                  25                  30
Leu Leu Gly Val Ser Asp Ser Gly Lys Ile Val Phe Leu Glu Glu Ala
            35                  40                  45
Ser Gln Gln Glu Lys Leu Ala Lys Glu Trp Cys Phe Lys Pro Cys Glu
    50                  55                  60
Ile Arg Glu Leu Ser His His Glu Phe Phe Met Pro Gly Leu Val Asp
65                  70                  75                  80
Thr His Ile His Ala Ser Gln Tyr Ser Phe Ala Gly Ser Ser Ile Asp
                85                  90                  95
Leu Pro Leu Leu Glu Trp Leu Thr Lys Tyr Thr Phe Pro Ala Glu His
            100                 105                 110
Arg Phe Gln Asn Ile Asp Phe Ala Glu Glu Val Tyr Thr Arg Val Val
        115                 120                 125
Arg Arg Thr Leu Lys Asn Gly Thr Thr Thr Ala Cys Tyr Phe Ala Thr
130                 135                 140
Ile His Thr Asp Ser Ser Leu Leu Leu Ala Asp Ile Thr Asp Lys Phe
145                 150                 155                 160
Gly Gln Arg Ala Phe Val Gly Lys Val Cys Met Asp Leu Asn Asp Thr
                165                 170                 175
Phe Pro Glu Tyr Lys Glu Thr Thr Glu Glu Ser Ile Lys Glu Thr Glu
            180                 185                 190
Arg Phe Val Ser Glu Met Leu Gln Lys Asn Tyr Ser Arg Val Lys Pro
        195                 200                 205
Ile Val Thr Pro Arg Phe Ser Leu Ser Cys Ser Glu Thr Leu Met Gly
210                 215                 220
Glu Leu Gly Asn Ile Ala Lys Thr Val Lys Asn Leu Tyr Pro Ser Tyr
225                 230                 235                 240
Lys Asn Tyr Thr Ser Val Tyr Asp Lys Asn Asn Leu Leu Thr Asn Lys
                245                 250                 255
Thr Val Met Ala His Gly Cys Tyr Leu Ser Ala Glu Glu Leu Asn Val
            260                 265                 270
Phe His Glu Arg Gly Ala Ser Ile Ala His Cys Pro Asn Ser Asn Leu
        275                 280                 285
Ser Leu Ser Ser Gly Phe Leu Asn Val Leu Glu Val Leu Lys His Glu
290                 295                 300
Val Lys Ile Gly Leu Gly Thr Asp Val Ala Gly Gly Tyr Ser Tyr Ser
305                 310                 315                 320
Met Leu Asp Ala Ile Arg Arg Ala Val Met Val Ser Asn Ile Leu Leu
                325                 330                 335
Ile Asn Lys Val Asn Glu Lys Ser Leu Thr Leu Lys Glu Val Phe Arg
            340                 345                 350
Leu Ala Thr Leu Gly Gly Ser Gln Ala Leu Gly Leu Asp Gly Glu Ile
        355                 360                 365
Gly Asn Phe Glu Val Gly Lys Glu Phe Asp Ala Ile Leu Ile Asn Pro
370                 375                 380
Lys Ala Ser Asp Ser Pro Ile Asp Leu Phe Tyr Gly Asp Phe Phe Gly
385                 390                 395                 400
```

```
Asp Ile Ser Glu Ala Val Ile Gln Lys Phe Leu Tyr Leu Gly Asp Asp
            405                 410                 415
Arg Asn Ile Glu Glu Val Tyr Val Gly Gly Lys Gln Val Val Pro Phe
            420                 425                 430
Ser Ser Ser Val
        435

<210> SEQ ID NO 14
<211> LENGTH: 436
<212> TYPE: PRT
<213> ORGANISM: Pongo pygmaeus

<400> SEQUENCE: 14

Met Cys Ala Ala Gln Met Pro Pro Leu Ala His Ile Phe Arg Gly Thr
1               5                   10                  15
Phe Val His Ser Thr Trp Thr Cys Pro Met Glu Val Leu Arg Asp His
                20                  25                  30
Leu Leu Gly Val Ser Asp Ser Gly Lys Ile Val Phe Leu Glu Glu Ala
            35                  40                  45
Ser Gln Gln Glu Lys Leu Ala Lys Glu Trp Cys Phe Lys Pro Cys Glu
    50                  55                  60
Ile Arg Glu Leu Ser His His Glu Phe Phe Met Pro Gly Leu Val Asp
65                  70                  75                  80
Thr His Ile His Ala Ser Gln Tyr Ser Phe Ala Gly Ser Asn Ile Asp
                85                  90                  95
Leu Pro Leu Leu Glu Trp Leu Thr Lys Tyr Thr Phe Pro Ala Glu His
            100                 105                 110
Arg Phe Gln Asn Thr Asp Phe Ala Glu Glu Val Tyr Thr Arg Val Val
        115                 120                 125
Arg Arg Thr Leu Lys Asn Gly Thr Thr Thr Ala Cys Tyr Phe Ala Thr
    130                 135                 140
Ile His Thr Asp Ser Ser Leu Leu Leu Ala Asp Ile Thr Asp Lys Phe
145                 150                 155                 160
Gly Gln Arg Ala Phe Val Gly Lys Val Cys Met Asn Leu Asn Asp Thr
                165                 170                 175
Phe Pro Glu Tyr Asn Glu Thr Thr Glu Glu Ser Ile Lys Glu Thr Glu
            180                 185                 190
Arg Phe Val Ser Glu Met Leu Gln Arg Lys Tyr Ser Arg Val Lys Pro
        195                 200                 205
Ile Val Thr Pro Arg Phe Ser Leu Ser Cys Ser Glu Thr Leu Met Gly
    210                 215                 220
Asp Leu Gly Asn Ile Ala Lys Thr Val Lys Asn Leu Tyr Pro Ser Tyr
225                 230                 235                 240
Lys Asn Tyr Thr Asp Val Tyr Asp Lys Asn Asn Leu Leu Thr Asn Lys
                245                 250                 255
Thr Val Met Ala His Gly Cys Tyr Leu Ser Ala Glu Glu Leu Asn Val
            260                 265                 270
Phe His Glu Arg Gly Ala Ser Ile Ala His Cys Pro Asn Ser Asn Leu
        275                 280                 285
Ser Leu Ser Ser Gly Phe Leu Asn Val Leu Glu Val Leu Lys His Glu
    290                 295                 300
Val Lys Ile Gly Leu Gly Thr Asp Val Ala Gly Gly Tyr Ser Tyr Ser
305                 310                 315                 320
Met Leu Asp Ala Ile Arg Arg Ala Val Met Val Ser Asn Ile Leu Leu
                325                 330                 335
```

-continued

```
Ile Asn Lys Val Asn Glu Lys Ser Leu Thr Leu Lys Glu Val Phe Arg
            340                 345                 350

Leu Ala Thr Leu Gly Gly Ser Gln Ala Leu Gly Leu Asp Gly Glu Ile
            355                 360                 365

Gly Asn Phe Glu Val Gly Lys Glu Phe Asp Ala Ile Leu Ile Asn Pro
            370                 375                 380

Lys Ala Ser Asp Ser Pro Ile Asp Leu Phe Tyr Gly Asp Phe Phe Gly
385                 390                 395                 400

Asp Ile Ser Glu Ala Val Ile Gln Lys Phe Leu Tyr Leu Gly Asp Asp
                405                 410                 415

Arg Asn Ile Glu Glu Val Tyr Val Gly Gly Lys Gln Val Val Pro Phe
            420                 425                 430

Ser Ser Ser Val
            435

<210> SEQ ID NO 15
<211> LENGTH: 436
<212> TYPE: PRT
<213> ORGANISM: Rattus norvegicus

<400> SEQUENCE: 15

Met Cys Ala Ala Arg Thr Pro Gln Leu Ala Leu Ile Phe Arg Gly Thr
1               5                   10                  15

Phe Val His Ser Thr Trp Thr Cys Pro Met Glu Val Leu Arg Asp His
                20                  25                  30

Leu Leu Gly Val Ser Asp Ser Gly Lys Ile Val Phe Leu Glu Glu Ser
            35                  40                  45

Ser Gln Gln Glu Lys Leu Ala Lys Glu Trp Cys Phe Lys Pro Cys Glu
        50                  55                  60

Ile Arg Glu Leu Ser His His Glu Phe Phe Met Pro Gly Leu Val Asp
65                  70                  75                  80

Thr His Ile His Ala Pro Gln Tyr Ala Phe Ala Gly Ser Asn Val Asp
                85                  90                  95

Leu Pro Leu Leu Asp Trp Leu Asn Lys Tyr Thr Phe Pro Thr Glu Lys
            100                 105                 110

Arg Phe Gln Ser Thr Asp Val Ala Glu Glu Val Tyr Thr Arg Val Val
        115                 120                 125

Arg Arg Thr Leu Lys Asn Gly Thr Thr Thr Ala Cys Tyr Phe Gly Thr
130                 135                 140

Ile His Thr Asp Ser Ser Leu Ile Leu Ala Glu Ile Thr Asp Lys Phe
145                 150                 155                 160

Gly Gln Arg Ala Phe Val Gly Lys Val Cys Met Asp Leu Asn Asn Thr
                165                 170                 175

Val Pro Glu Tyr Lys Glu Thr Thr Glu Glu Ser Val Lys Glu Thr Glu
            180                 185                 190

Arg Phe Val Ser Glu Met Leu Gln Lys Asn Tyr Ser Arg Val Lys Pro
        195                 200                 205

Ile Val Thr Pro Arg Phe Ser Leu Ser Cys Thr Glu Thr Leu Met Ser
    210                 215                 220

Glu Leu Gly Asn Ile Ala Lys Thr Val Lys Ser Leu Tyr Pro Gly Tyr
225                 230                 235                 240

Lys Asn Tyr Thr Asp Val Tyr Asp Lys Asn Asn Leu Leu Thr Asn Lys
                245                 250                 255

Thr Val Met Ala His Gly Cys Tyr Leu Ser Glu Glu Glu Leu Asn Val
```

```
                 260                 265                 270
Phe Ser Glu Arg Gly Ala Ser Ile Ala His Cys Pro Asn Ser Asn Leu
            275                 280                 285

Ser Leu Ser Ser Gly Leu Leu Asn Val Leu Asp Val Leu Lys His Lys
        290                 295                 300

Val Lys Ile Gly Leu Gly Thr Asp Val Ala Gly Gly Tyr Ser Tyr Ser
305                 310                 315                 320

Met Leu Asp Ala Ile Arg Arg Ala Val Met Val Ser Asn Val Leu Leu
                325                 330                 335

Ile Asn Lys Val Asn Glu Lys Ser Leu Thr Leu Lys Glu Val Phe Arg
                340                 345                 350

Leu Ala Thr Leu Gly Gly Ser Gln Ala Leu Gly Leu Asp Arg Glu Ile
            355                 360                 365

Gly Asn Phe Glu Val Gly Lys Asp Phe Asp Ala Leu Leu Ile Asn Pro
        370                 375                 380

Arg Ala Ser Asp Ser Pro Ile Asp Leu Phe Cys Gly Asp Phe Val Gly
385                 390                 395                 400

Asp Ile Ser Glu Ala Val Ile Gln Lys Phe Leu Tyr Leu Gly Asp Asp
                405                 410                 415

Arg Asn Ile Glu Glu Val Tyr Val Gly Gly Lys Gln Val Val Pro Phe
                420                 425                 430

Ser Ser Ser Val
            435

<210> SEQ ID NO 16
<211> LENGTH: 436
<212> TYPE: PRT
<213> ORGANISM: Mus musculus

<400> SEQUENCE: 16

Met Cys Ala Ala Arg Thr Pro Pro Leu Ala Leu Val Phe Arg Gly Thr
1               5                   10                  15

Phe Val His Ser Thr Trp Thr Cys Pro Met Glu Val Leu Arg Asp His
            20                  25                  30

Leu Leu Gly Val Ser Asp Ser Gly Lys Ile Val Phe Leu Glu Glu Ser
        35                  40                  45

Ser Gln Gln Glu Lys Leu Ala Lys Glu Trp Cys Phe Lys Pro Cys Glu
    50                  55                  60

Ile Arg Glu Leu Ser His His Glu Phe Phe Met Pro Gly Leu Val Asp
65                  70                  75                  80

Thr His Ile His Ala Pro Gln Tyr Ala Phe Ala Gly Ser Asn Val Asp
                85                  90                  95

Leu Pro Leu Leu Glu Trp Leu Asn Lys Tyr Thr Phe Pro Thr Glu Gln
            100                 105                 110

Arg Phe Arg Ser Thr Asp Val Ala Glu Glu Val Tyr Thr Arg Val Val
        115                 120                 125

Arg Arg Thr Leu Lys Asn Gly Thr Thr Thr Ala Cys Tyr Phe Gly Thr
    130                 135                 140

Ile His Thr Asp Ser Ser Leu Ile Leu Ala Glu Ile Thr Asp Lys Phe
145                 150                 155                 160

Gly Gln Arg Ala Phe Val Gly Lys Val Cys Met Asp Leu Asn Asp Thr
                165                 170                 175

Val Pro Glu Tyr Lys Glu Thr Thr Glu Glu Ser Val Lys Glu Thr Glu
            180                 185                 190
```

```
Arg Phe Val Ser Glu Met Leu Gln Lys Asn Tyr Pro Arg Val Lys Pro
            195                 200                 205

Ile Val Thr Pro Arg Phe Thr Leu Ser Cys Thr Glu Thr Leu Met Ser
210                 215                 220

Glu Leu Gly Asn Ile Ala Lys Thr Val Lys Ser Leu Tyr Pro Ser Tyr
225                 230                 235                 240

Lys Asn Tyr Thr Asp Val Tyr Asp Lys Asn Asn Leu Leu Thr Asn Lys
            245                 250                 255

Thr Val Met Ala His Gly Cys Tyr Leu Ser Glu Glu Leu Asn Ile
            260                 265                 270

Phe Ser Glu Arg Gly Ala Ser Ile Ala His Cys Pro Asn Ser Asn Leu
            275                 280                 285

Ser Leu Ser Ser Gly Leu Leu Asn Val Leu Glu Val Leu Lys His Lys
            290                 295                 300

Val Lys Ile Gly Leu Gly Thr Asp Val Ala Gly Tyr Ser Tyr Ser
305                 310                 315                 320

Met Leu Asp Ala Ile Arg Arg Ala Val Met Val Ser Asn Val Leu Leu
            325                 330                 335

Ile Asn Lys Val Asn Glu Lys Asn Leu Thr Leu Lys Glu Val Phe Arg
            340                 345                 350

Leu Ala Thr Leu Gly Gly Ser Gln Ala Leu Gly Leu Asp Ser Glu Ile
            355                 360                 365

Gly Asn Phe Glu Val Gly Lys Glu Phe Asp Ala Leu Leu Ile Asn Pro
            370                 375                 380

Arg Ala Ser Asp Ser Pro Ile Asp Leu Phe Tyr Gly Asp Phe Val Gly
385                 390                 395                 400

Asp Ile Ser Glu Ala Val Ile Gln Lys Phe Leu Tyr Leu Gly Asp Asp
            405                 410                 415

Arg Asn Ile Glu Glu Val Tyr Val Gly Gly Lys Gln Val Val Pro Phe
            420                 425                 430

Ser Ser Ser Val
            435

<210> SEQ ID NO 17
<211> LENGTH: 400
<212> TYPE: PRT
<213> ORGANISM: Homo sapiens

<400> SEQUENCE: 17

Met Cys Ala Ala Gln Met Pro Pro Leu Ala His Ile Phe Arg Gly Thr
1               5                   10                  15

Phe Val His Ser Thr Trp Thr Cys Pro Met Glu Val Leu Arg Asp His
            20                  25                  30

Leu Leu Gly Val Ser Asp Ser Gly Lys Ile Val Phe Leu Glu Glu Ala
            35                  40                  45

Ser Gln Gln Glu Lys Leu Ala Lys Glu Trp Cys Phe Lys Pro Cys Glu
            50                  55                  60

Ile Arg Glu Leu Ser His His Glu Phe Phe Met Pro Gly Leu Val Asp
65                  70                  75                  80

Thr His Ile His Ala Ser Gln Tyr Ser Phe Ala Gly Ser Ser Ile Asp
            85                  90                  95

Leu Pro Leu Leu Glu Trp Leu Thr Lys Tyr Thr Phe Pro Ala Glu His
            100                 105                 110

Arg Phe Gln Asn Ile Asp Phe Ala Glu Glu Val Tyr Thr Arg Val Val
            115                 120                 125
```

Arg Arg Thr Leu Lys Asn Gly Thr Thr Thr Ala Cys Tyr Phe Ala Thr
130                 135                 140

Ile His Thr Asp Ser Ser Leu Leu Ala Asp Ile Thr Asp Lys Phe
145                 150                 155                 160

Gly Gln Arg Ala Phe Val Gly Lys Val Cys Met Asp Leu Asn Asp Thr
                165                 170                 175

Phe Pro Glu Tyr Lys Glu Thr Thr Glu Glu Ser Ile Lys Glu Thr Glu
                180                 185                 190

Arg Phe Val Ser Glu Met Leu Gln Lys Asn Tyr Ser Arg Val Lys Pro
                195                 200                 205

Ile Val Thr Pro Arg Phe Ser Leu Ser Cys Ser Glu Thr Leu Met Gly
210                 215                 220

Glu Leu Gly Asn Ile Ala Lys Thr Arg Asp Leu His Ile Gln Ser His
225                 230                 235                 240

Ile Ser Glu Asn Arg Asp Glu Val Glu Ala Val Lys Asn Leu Tyr Pro
                245                 250                 255

Ser Tyr Lys Asn Tyr Thr Ser Val Tyr Asp Lys Asn Asn Leu Leu Thr
                260                 265                 270

Asn Lys Thr Val Met Ala His Gly Cys Tyr Leu Ser Ala Glu Glu Leu
                275                 280                 285

Asn Val Phe His Glu Arg Gly Ala Ser Ile Ala His Cys Pro Asn Ser
                290                 295                 300

Asn Leu Ser Leu Ser Ser Gly Phe Leu Asn Val Leu Glu Val Leu Lys
305                 310                 315                 320

His Glu Val Lys Ile Gly Leu Gly Thr Asp Val Ala Gly Gly Tyr Ser
                325                 330                 335

Tyr Ser Met Leu Asp Ala Ile Arg Arg Ala Val Met Val Ala Ser Asp
                340                 345                 350

Ser Pro Ile Asp Leu Phe Tyr Gly Asp Phe Gly Asp Ile Ser Glu
                355                 360                 365

Ala Val Ile Gln Lys Phe Leu Tyr Leu Gly Asp Asp Arg Asn Ile Glu
370                 375                 380

Glu Val Tyr Val Gly Gly Lys Gln Val Val Pro Phe Ser Ser Ser Val
385                 390                 395                 400

<210> SEQ ID NO 18
<211> LENGTH: 400
<212> TYPE: PRT
<213> ORGANISM: Pongo pygmaeus

<400> SEQUENCE: 18

Met Cys Ala Ala Gln Met Pro Pro Leu Ala His Ile Phe Arg Gly Thr
1               5                   10                  15

Phe Val His Ser Thr Trp Thr Cys Pro Met Glu Val Leu Arg Asp His
                20                  25                  30

Leu Leu Gly Val Ser Asp Ser Gly Lys Ile Val Phe Leu Glu Glu Ala
                35                  40                  45

Ser Gln Gln Glu Lys Leu Ala Lys Glu Trp Cys Phe Lys Pro Cys Glu
50                  55                  60

Ile Arg Glu Leu Ser His His Glu Phe Met Pro Gly Leu Val Asp
65                  70                  75                  80

Thr His Ile His Ala Ser Gln Tyr Ser Phe Ala Gly Ser Asn Ile Asp
                85                  90                  95

Leu Pro Leu Leu Glu Trp Leu Thr Lys Tyr Thr Phe Pro Ala Glu His

-continued

```
                100                 105                 110
Arg Phe Gln Asn Thr Asp Phe Ala Glu Glu Val Tyr Thr Arg Val Val
            115                 120                 125

Arg Arg Thr Leu Lys Asn Gly Thr Thr Thr Ala Cys Tyr Phe Ala Thr
130                 135                 140

Ile His Thr Asp Ser Ser Leu Leu Leu Ala Asp Ile Thr Asp Lys Phe
145                 150                 155                 160

Gly Gln Arg Ala Phe Val Gly Lys Val Cys Met Asn Leu Asn Asp Thr
                165                 170                 175

Phe Pro Glu Tyr Asn Glu Thr Thr Glu Glu Ser Ile Lys Glu Thr Glu
            180                 185                 190

Arg Phe Val Ser Glu Met Leu Gln Arg Lys Tyr Ser Arg Val Lys Pro
            195                 200                 205

Ile Val Thr Pro Arg Phe Ser Leu Ser Cys Ser Glu Thr Leu Met Gly
            210                 215                 220

Asp Leu Gly Asn Ile Ala Lys Thr His Asp Leu His Ile Gln Ser His
225                 230                 235                 240

Ile Ser Glu Asn Arg Asp Glu Val Glu Ala Val Lys Asn Leu Tyr Pro
                245                 250                 255

Ser Tyr Lys Asn Tyr Thr Asp Val Tyr Asp Lys Asn Asn Leu Leu Thr
            260                 265                 270

Asn Lys Thr Val Met Ala His Gly Cys Tyr Leu Ser Ala Glu Glu Leu
            275                 280                 285

Asn Val Phe His Glu Arg Gly Ala Ser Ile Ala His Cys Pro Asn Ser
            290                 295                 300

Asn Leu Ser Leu Ser Ser Gly Phe Leu Asn Val Leu Glu Val Leu Lys
305                 310                 315                 320

His Glu Val Lys Ile Gly Leu Gly Thr Asp Val Ala Gly Gly Tyr Ser
                325                 330                 335

Tyr Ser Met Leu Asp Ala Ile Arg Arg Ala Val Met Val Ala Ser Asp
            340                 345                 350

Ser Pro Ile Asp Leu Phe Tyr Gly Asp Phe Phe Gly Asp Ile Ser Glu
            355                 360                 365

Ala Val Ile Gln Lys Phe Leu Tyr Leu Gly Asp Asp Arg Asn Ile Glu
            370                 375                 380

Glu Val Tyr Val Gly Gly Lys Gln Val Val Pro Phe Ser Ser Ser Val
385                 390                 395                 400

<210> SEQ ID NO 19
<211> LENGTH: 400
<212> TYPE: PRT
<213> ORGANISM: Rattus norvegicus

<400> SEQUENCE: 19

Met Cys Ala Ala Arg Thr Pro Gln Leu Ala Leu Ile Phe Arg Gly Thr
1               5                   10                  15

Phe Val His Ser Thr Trp Thr Cys Pro Met Glu Val Leu Arg Asp His
            20                  25                  30

Leu Leu Gly Val Ser Asp Ser Gly Lys Ile Val Phe Leu Glu Glu Ser
        35                  40                  45

Ser Gln Gln Glu Lys Leu Ala Lys Glu Trp Cys Phe Lys Pro Cys Glu
    50                  55                  60

Ile Arg Glu Leu Ser His His Glu Phe Met Pro Gly Leu Val Asp
65                  70                  75                  80
```

```
Thr His Ile His Ala Pro Gln Tyr Ala Phe Ala Gly Ser Asn Val Asp
                85                  90                  95

Leu Pro Leu Leu Asp Trp Leu Asn Lys Tyr Thr Phe Pro Thr Glu Lys
            100                 105                 110

Arg Phe Gln Ser Thr Asp Val Ala Glu Glu Val Tyr Thr Arg Val Val
        115                 120                 125

Arg Arg Thr Leu Lys Asn Gly Thr Thr Thr Ala Cys Tyr Phe Gly Thr
130                 135                 140

Ile His Thr Asp Ser Ser Leu Ile Leu Ala Glu Ile Thr Asp Lys Phe
145                 150                 155                 160

Gly Gln Arg Ala Phe Val Gly Lys Val Cys Met Asp Leu Asn Asn Thr
                165                 170                 175

Val Pro Glu Tyr Lys Glu Thr Thr Glu Glu Ser Val Lys Glu Thr Glu
            180                 185                 190

Arg Phe Val Ser Glu Met Leu Gln Lys Asn Tyr Ser Arg Val Lys Pro
        195                 200                 205

Ile Val Thr Pro Arg Phe Ser Leu Ser Cys Thr Glu Thr Leu Met Ser
210                 215                 220

Glu Leu Gly Asn Ile Ala Lys Thr His Asp Leu Tyr Ile Gln Ser His
225                 230                 235                 240

Ile Ser Glu Asn Arg Glu Glu Ile Glu Ala Val Lys Ser Leu Tyr Pro
                245                 250                 255

Gly Tyr Lys Asn Tyr Thr Asp Val Tyr Asp Lys Asn Asn Leu Leu Thr
            260                 265                 270

Asn Lys Thr Val Met Ala His Gly Cys Tyr Leu Ser Glu Glu Glu Leu
        275                 280                 285

Asn Val Phe Ser Glu Arg Gly Ala Ser Ile Ala His Cys Pro Asn Ser
290                 295                 300

Asn Leu Ser Leu Ser Ser Gly Leu Leu Asn Val Leu Asp Val Leu Lys
305                 310                 315                 320

His Lys Val Lys Ile Gly Leu Gly Thr Asp Val Ala Gly Gly Tyr Ser
                325                 330                 335

Tyr Ser Met Leu Asp Ala Ile Arg Arg Ala Val Met Val Ala Ser Asp
            340                 345                 350

Ser Pro Ile Asp Leu Phe Cys Gly Asp Phe Val Gly Asp Ile Ser Glu
        355                 360                 365

Ala Val Ile Gln Lys Phe Leu Tyr Leu Gly Asp Asp Arg Asn Ile Glu
370                 375                 380

Glu Val Tyr Val Gly Gly Lys Gln Val Val Pro Phe Ser Ser Ser Val
385                 390                 395                 400

<210> SEQ ID NO 20
<211> LENGTH: 400
<212> TYPE: PRT
<213> ORGANISM: Mus musculus

<400> SEQUENCE: 20

Met Cys Ala Ala Arg Thr Pro Pro Leu Ala Leu Val Phe Arg Gly Thr
1               5                   10                  15

Phe Val His Ser Thr Trp Thr Cys Pro Met Glu Val Leu Arg Asp His
            20                  25                  30

Leu Leu Gly Val Ser Asp Ser Gly Lys Ile Val Phe Leu Glu Glu Ser
        35                  40                  45

Ser Gln Gln Glu Lys Leu Ala Lys Glu Trp Cys Phe Lys Pro Cys Glu
50                  55                  60
```

```
Ile Arg Glu Leu Ser His His Glu Phe Phe Met Pro Gly Leu Val Asp
 65                  70                  75                  80

Thr His Ile His Ala Pro Gln Tyr Ala Phe Ala Gly Ser Asn Val Asp
                 85                  90                  95

Leu Pro Leu Leu Glu Trp Leu Asn Lys Tyr Thr Phe Pro Thr Glu Gln
            100                 105                 110

Arg Phe Arg Ser Thr Asp Val Ala Glu Val Tyr Thr Arg Val Val
        115                 120                 125

Arg Arg Thr Leu Lys Asn Gly Thr Thr Thr Ala Cys Tyr Phe Gly Thr
    130                 135                 140

Ile His Thr Asp Ser Ser Leu Ile Leu Ala Glu Ile Thr Asp Lys Phe
145                 150                 155                 160

Gly Gln Arg Ala Phe Val Gly Lys Val Cys Met Asp Leu Asn Asp Thr
                165                 170                 175

Val Pro Glu Tyr Lys Glu Thr Thr Glu Glu Ser Val Lys Glu Thr Glu
                180                 185                 190

Arg Phe Val Ser Glu Met Leu Gln Lys Asn Tyr Pro Arg Val Lys Pro
        195                 200                 205

Ile Val Thr Pro Arg Phe Thr Leu Ser Cys Thr Glu Thr Leu Met Ser
210                 215                 220

Glu Leu Gly Asn Ile Ala Lys Thr His Asp Leu Tyr Ile Gln Ser His
225                 230                 235                 240

Ile Ser Glu Asn Arg Glu Glu Ile Glu Ala Val Lys Ser Leu Tyr Pro
                245                 250                 255

Ser Tyr Lys Asn Tyr Thr Asp Val Tyr Asp Lys Asn Asn Leu Leu Thr
                260                 265                 270

Asn Lys Thr Val Met Ala His Gly Cys Tyr Leu Ser Glu Glu Leu
    275                 280                 285

Asn Ile Phe Ser Glu Arg Gly Ala Ser Ile Ala His Cys Pro Asn Ser
290                 295                 300

Asn Leu Ser Leu Ser Ser Gly Leu Leu Asn Val Leu Glu Val Leu Lys
305                 310                 315                 320

His Lys Val Lys Ile Gly Leu Gly Thr Asp Val Ala Gly Gly Tyr Ser
                325                 330                 335

Tyr Ser Met Leu Asp Ala Ile Arg Arg Ala Val Met Val Ala Ser Asp
                340                 345                 350

Ser Pro Ile Asp Leu Phe Tyr Gly Asp Phe Val Gly Asp Ile Ser Glu
        355                 360                 365

Ala Val Ile Gln Lys Phe Leu Tyr Leu Gly Asp Asp Arg Asn Ile Glu
    370                 375                 380

Glu Val Tyr Val Gly Gly Lys Gln Val Val Pro Phe Ser Ser Ser Val
385                 390                 395                 400

<210> SEQ ID NO 21
<211> LENGTH: 104
<212> TYPE: PRT
<213> ORGANISM: Homo sapiens

<400> SEQUENCE: 21

Met Cys Ala Ala Gln Met Pro Pro Leu Ala His Ile Phe Arg Gly Thr
  1               5                  10                  15

Phe Val His Ser Thr Trp Thr Cys Pro Met Glu Val Leu Arg Asp His
                 20                  25                  30

Leu Leu Gly Val Ser Asp Ser Gly Lys Ile Val Phe Leu Glu Glu Ala
```

-continued

```
                 35                  40                  45

Ser Gln Gln Glu Lys Leu Ala Lys Glu Trp Cys Phe Lys Pro Cys Glu
         50                  55                  60

Ile Arg Glu Leu Ser His His Glu Phe Phe Met Pro Gly Leu Val Asp
 65                  70                  75                  80

Thr His Ile His Ala Ser Gln Tyr Ser Phe Ala Gly Ser Ser Ile Asp
                 85                  90                  95

Leu Pro Leu Leu Ser Ser Ser Val
            100

<210> SEQ ID NO 22
<211> LENGTH: 104
<212> TYPE: PRT
<213> ORGANISM: Pongo pygmaeus

<400> SEQUENCE: 22

Met Cys Ala Ala Gln Met Pro Pro Leu Ala His Ile Phe Arg Gly Thr
  1               5                  10                  15

Phe Val His Ser Thr Trp Thr Cys Pro Met Glu Val Leu Arg Asp His
                 20                  25                  30

Leu Leu Gly Val Ser Asp Ser Gly Lys Ile Val Phe Leu Glu Glu Ala
             35                  40                  45

Ser Gln Gln Glu Lys Leu Ala Lys Glu Trp Cys Phe Lys Pro Cys Glu
         50                  55                  60

Ile Arg Glu Leu Ser His His Glu Phe Phe Met Pro Gly Leu Val Asp
 65                  70                  75                  80

Thr His Ile His Ala Ser Gln Tyr Ser Phe Ala Gly Ser Asn Ile Asp
                 85                  90                  95

Leu Pro Leu Leu Ser Ser Ser Val
            100

<210> SEQ ID NO 23
<211> LENGTH: 104
<212> TYPE: PRT
<213> ORGANISM: Rattus norvegicus

<400> SEQUENCE: 23

Met Cys Ala Ala Arg Thr Pro Gln Leu Ala Leu Ile Phe Arg Gly Thr
  1               5                  10                  15

Phe Val His Ser Thr Trp Thr Cys Pro Met Glu Val Leu Arg Asp His
                 20                  25                  30

Leu Leu Gly Val Ser Asp Ser Gly Lys Ile Val Phe Leu Glu Glu Ser
             35                  40                  45

Ser Gln Gln Glu Lys Leu Ala Lys Glu Trp Cys Phe Lys Pro Cys Glu
         50                  55                  60

Ile Arg Glu Leu Ser His His Glu Phe Phe Met Pro Gly Leu Val Asp
 65                  70                  75                  80

Thr His Ile His Ala Pro Gln Tyr Ala Phe Ala Gly Ser Asn Val Asp
                 85                  90                  95

Leu Pro Leu Leu Ser Ser Ser Val
            100

<210> SEQ ID NO 24
<211> LENGTH: 104
<212> TYPE: PRT
<213> ORGANISM: Mus musculus

<400> SEQUENCE: 24
```

-continued

```
Met Cys Ala Ala Arg Thr Pro Pro Leu Ala Leu Val Phe Arg Gly Thr
1               5                   10                  15

Phe Val His Ser Thr Trp Thr Cys Pro Met Glu Val Leu Arg Asp His
            20                  25                  30

Leu Leu Gly Val Ser Asp Ser Gly Lys Ile Val Phe Leu Glu Glu Ser
            35                  40                  45

Ser Gln Gln Glu Lys Leu Ala Lys Glu Trp Cys Phe Lys Pro Cys Glu
            50                  55                  60

Ile Arg Glu Leu Ser His His Glu Phe Phe Met Pro Gly Leu Val Asp
65                  70                  75                  80

Thr His Ile His Ala Pro Gln Tyr Ala Phe Ala Gly Ser Asn Val Asp
                85                  90                  95

Leu Pro Leu Leu Ser Ser Ser Val
                100
```

CYPIN POLYPEPTIDE AND FRAGMENTS THEREOF

CROSS-REFERENCE TO RELATED APPLICATIONS

This application is a divisional of U.S. application Ser. No. 11/033,909 filed on Jan. 12, 2005, which claims priority to U.S. provisional patent application Ser. No. 60/535,512, filed Jan. 12, 2004, U.S. provisional patent application Ser. No. 60/535,533, filed Jan. 12, 2004, U.S. provisional patent application Ser. No. 60/535,534, filed Jan. 12, 2004 and U.S. provisional patent application Ser. No. 60/577,922, filed Jun. 9, 2004, each is herein incorporated by reference.

GOVERNMENT INTERESTS

This invention was made with U.S. Government funds (NSF IBN 0234206). Therefore, the Government may have rights in this invention.

FIELD OF THE INVENTION

The present invention generally relates to the structure, function and uses of a protein and fragments thereof, alone and in combination, involved in the regulation of nerve cell activity and morphology, which affects learning and memory disorders.

BACKGROUND OF THE INVENTION

The establishment of dendrite morphology is crucial for normal neuronal communication in the brain. This development includes both the spatial and functional assembly of signal transduction machinery at synaptic sites and precise patterning of dendrites and their branches. Dendrite branching plays an important role in normal brain function. Branching patterns, the relationship between the primary dendrites arising from the cell body and the secondary dendrites arising from primary dendrites, appear to be cell-type specific and play a role in determining how information is received and processed by a neuron. Further, trafficking of proteins during neuronal development and homeostasis affects or is related to dendrite branching. The amount of branches that a dendrite, or input center of a neuron, contains is thought to be directly related to learning and memory. In many learning disorders, such as autism, Rett syndrome, Down syndrome, Fetal Alcohol syndrome and Alzheimer's disease, patients show a reduced number of dendrite branches. These patients also often show alterations in the metabolism, or breakdown, of a class of compounds called purines.

Clues to how neurons regulate their dendritic morphology come from studies of patients with disorders that result in cognitive deficits. Evidence suggests that patients with these disorders have defects in dendrite number and arborization, as well as deficits in purine production, purine metabolism, or pterins, which are important for purine synthesis. Although these studies are mostly correlative, the first evidence for the idea that purine metabolic disorders underlie cognitive defects was from patients with Lesch-Nyhan syndrome (LNS). LNS is an X-linked disorder that involves the absence of hypoxanthine guanine phosphoribosyltransferase (HPRT) (Lesch and Nyhan, Am. J. Med. 36:561-70 (1964); Seegmiller et al., Science 770:1682-4 (1967); Rossiter and Caskey, Drugs Aging 2:117 (1995)). LNS patients suffer from movement disorders, self-injury, and mental retardation. This deficit always results in increased uric acid levels in the urine, reflecting alterations in purine metabolism, and patients often have neurological abnormalities. Besides Lesch-Nyhan syndrome, both dendrite number or branching defects and purine synthesis/metabolism defects are seen in individuals with autism, (Jaeken and Van den Berghe, Lancet 2:1058 (1984); Stone et al., Nat. Genet. 1:59 (1992); Raymond et al., Acta. Neropathol. 91:117 (1996); Page and Coleman, Adv. Exp. Med. Biol. 431:793 (1998); Page and Coleman, Biochim. Biophys. Acta. 1500:291 (2000); Herbert et al., Brain 126: 1182 (2003)); Rett syndrome (Belichenko et al., Neuroreport. 5:1509 (1994); Belichenko and Dahlstrom, J. Neurosci. Methods 57:55 (1995); Rocchigiani et al., Neuropediatrics 26:288-92 (1995); Boltshauser et al., Am. J. Med. Genet. Suppl. 1:317-21 (1986); Zoghbi et al., Ann. Neurol. 25:56 (1989); Subramaniam et al., Neurology 48:399 (1997); Messahel et al., Eur. J. Paediatr. Neurol. 4:211 (2000); Armstrong, Brain Dev. 23 Suppl 1:S72. (2001); Raemaekers et al., J. Cell Biol. 162:1017-29 (2003)); Down's syndrome (Fuller et al., Science 137:868 (1962); Huttenlocher, Neurology 20:381 (1970); Huttenlocher, Neurology 24:203 (1974); Purpura, Science 186:1126 (1974); Purpura, UCLA Forum Med. Sci. 18:141 (1975); Marin-Padilla, J. Comp. Neurol. 167:63 (1976); Takashima et al., 1981 Brain Res. 225:1 (1981); Puukka et al., Clin. Chim. Acta. 126:275 (1982); Puukka et al., Biochem. Med. Metab. Biol. 36:45 (1986); Becker et al., Ann. Neurol. 20:520 (1986); Takashima et al., Brain Dev. 11:131 (1989); Schulz and Scholz, J. Hirnforsch 33:37 (1992); Prinz et al., Histol. Histopathol. 12:895 (1997); James et al., Am. J. Clin. Nutr. 70:495 (1999); Kaufmann and Moser, Cereb. Cortex. 10:981 (2000); Hobbs et al., Am. J. Hum. Genet. 67:623 (2000)) and Fragile-X syndrome (Berry-Kravis and Huttenlocher, Ann. Neurol. 31:22 (1992); Roessler et al., J. Biol. Chem. 268:26476 (1993); Irwin et al., Am. J. Med. Genet. 98:161 (2001); Nimchinsky et al., J. Neurosci. 21:5139 (2001); Galvez et al., Brain Res. 971:83 (2003); Garcia-Pavia et al., Arthritis Rheum. 48:2036 (2003); Lee et al., Development 130:5543 (2003)). There are also reports of decreased dendrite number in patients with Alzheimer's disease (for example Arendt et al., J. Neurosci. 17:516 (1997); Ohm et al., Acta. Neuropathol. (Berl) 103:437 (2002)).

Thus, although there is no current consensus on how the absence of HPRT affects dendrite number or branching, abnormal dendrite number or branching may underlie the neurological symptoms of LNS and other related disorders. Although purine metabolic defects have not been well characterized in these patients, agents that increase dendrite number and/or branching may act to help these patients with memory. As a result, there is an immediate need for a sensitive assay for early diagnosis of cognitive disorders such as Alzheimer's disease, autism, Rett syndrome, Parkinson's disease, fetal alcohol syndrome, etc, as well as assays for identification of compounds to treat these and other cognitive disorders.

SUMMARY OF THE INVENTION

The present invention fills the foregoing need by providing such assays and materials. The present invention relates to methods of using cypin in assays for diagnosing and monitoring cognitive disorders, such as for example, autism, Lesch-Nyhan syndrome, Rett syndrome, Down syndrome, Fragile-X syndrome, Alzheimer's disease, Parkinson's disease, fetal alcohol syndrome, etc., as well as for identifying compounds to treat these and other cognitive disorders. The present invention exploits Applicant's discoveries regarding cypin, a protein found in nerve cells that controls dendrite development, including the regulation of microtubule assembly, dendrite morphology and dendrite patterning and branching in the brain. Applicant has discovered that cypin acts as a molecular "glue" that cements molecules together into long chains that form the "skeleton" of the dendrite. When humans and animals learn, neurons in the brain become more active, and cypin production increases and dendrite growth increases. In disease states such as Alzeimer's disease, Rhetts syndrome, fetal alcohol syndrome, mental retardation, etc., where there are deficits in memory, there are smaller amounts of branches on neurons. Just as cypin is associated with proper learning and memory, a lack of cypin correlates with learning disabilities and diseases.

Accordingly, one aspect of the present invention is directed to a method for use in the diagnosis of a cognitive disorder in a subject comprising detecting a test amount of a cypin gene product in a sample from the subject; and comparing the test amount with a normal amount of cypin gene product in a control sample, whereby a finding that the test amount is less than the normal amount provides a positive indication in the diagnosis of a cognitive disorder. In some embodiments, the cypin gene product is cypin polypeptide. In other embodiments, the cypin gene product is cypin mRNA or cDNA.

Another aspect of the present invention is directed to a method for use in the prognosis of a cognitive disorder in a subject comprising the steps of: detecting a test amount of a cypin gene product in a sample from the subject; and comparing the test amount with prognostic amounts of the cypin gene product in control samples, whereby a comparison of the test amount with the prognostic amounts provides an indication of the prognosis of cognitive disorder. In some embodiments, the cypin gene product is cypin polypeptide. In other embodiments, the cypin gene product is cypin mRNA or cDNA.

Another aspect of the present invention is directed to a method for use in monitoring the course of a cognitive disorder in a subject comprising the steps of: detecting a first test amount of a cypin gene product in a sample from the subject at a first time; detecting a second test amount of the cypin gene product in a sample from the subject at a second, later time; and comparing the first test amount and the second test amount, whereby an decrease in the amount of the cypin gene product in the second test amount as compared with the first test amount indicates progression of the cognitive disorder, and whereby an increase in the amount of the cypin gene product in the second test amount as compared with the first test amount indicates improvement of the cognitive disorder. In some embodiments, the cypin gene product is cypin polypeptide. In other embodiments, the cypin gene product is cypin mRNA or cDNA.

Another aspect of the present invention is directed to a method for assessing the efficacy of a treatment for a cognitive disorder in a subject comprising the steps of: detecting a first test amount of a cypin gene product in a sample from the subject prior to treatment; detecting a second test amount of the cypin gene product in a sample from the subject after treatment; and comparing the first test amount and the second test amount, whereby an increase in the amount of the cypin gene product in the second test amount as compared with the first test amount indicates that the treatment for cognitive disorders is efficacious. In some embodiments, the cypin gene product is cypin polypeptide. In other embodiments, the cypin gene product is cypin mRNA or cDNA.

Another aspect of the present invention is directed a method for identifying a compound capable of increasing expression of cypin, comprising: (a) providing a cell capable of expressing cypin; (b) contacting said cell with a candidate agent to be tested; and (c) measuring the level of a cypin gene product, whereby a compound capable of increasing expression of cypin is identified by measurement of an increased level of cypin gene product compared to the level produced in the absence of such compound. In some embodiments, the cypin gene product is cypin polypeptide. In other embodiments, the cypin gene product is cypin mRNA or cDNA.

Another aspect of the present invention is directed a method for identifying a compound capable of decreasing expression of cypin, comprising: (a) providing a cell capable of expressing cypin; (b) contacting said cell with a candidate agent to be tested; and (c) measuring the level of a cypin gene product, whereby a compound capable of decreasing expression of cypin is identified by measurement of a decreased level of cypin gene product compared to the level produced in the absence of such compound. In some embodiments, the cypin gene product is cypin polypeptide. In other embodiments, the cypin gene product is cypin mRNA or cDNA.

Another aspect of the present invention is directed a method for identifying an agonist of cypin comprising: (a) providing a sample comprising a cypin polypeptide or fragment thereof; (b) contacting said sample with a candidate agent to be tested for cypin agonistic activity; and (c) measuring the activity of cypin polypeptide or fragment thereof, whereby a cypin agonist is identified by measurement of an increase in activity as compared to the activity measured in the absence of such agonist. The activity measured can be dendrite formation, dendrite branching, guanine deaminase activity, guanine binding, microtubule formation, tubulin binding, and PDZ domain binding.

Another aspect of the present invention is directed a method for identifying an antagonist of cypin comprising: (a) providing a sample comprising a cypin polypeptide or fragment thereof; (b) contacting said sample with a candidate agent to be tested for cypin agonistic activity; and (c) measuring the activity of cypin polypeptide or fragment thereof, whereby a cypin agonist is identified by measurement of a decrease in activity as compared to the activity measured in the absence of such antagonist. The activity measured can be dendrite formation, dendrite branching, guanine deaminase activity, guanine binding, microtubule formation, tubulin binding, and PDZ domain binding.

Another aspect of the present invention is directed to a method for increasing cypin expression and/or activity in a cell comprising contacting a cell with an agent in an amount effective to increase expression and/or activity of cypin. In some embodiments, the agent is a cypin polypeptide or fragment thereof. In other embodiments, the agent is a compound that increases dendrite formation and/or branching in neurons.

Another aspect of the present invention is directed to a method of regulating dendrite formation and/or branching in a cell comprising contacting a cell capable of forming dendrites with an agent for a time sufficient to increase or decrease dendrite formation and/or branching. In some embodiments, the agent is a cypin polypeptide or fragment thereof.

Another aspect of the present invention is directed to a method of regulating microtubule assembly in a cell comprising contacting a cell with an agent for a time sufficient to induce or inhibit microtubule assembly. In some embodiments, the agent is a cypin polypeptide or fragment thereof.

A method of regulating PSD-95 clustering at postsynaptic sites in a cell comprising contacting a cell with an agent for a time sufficient to increase or decrease PSD-95 clustering. In some embodiments, the agent is a cypin polypeptide or fragment thereof.

Another aspect of the present invention is directed to a fragment of a cypin polypeptide comprising a deletion of one or more domains, including the zinc-binding aminohydrolase domain, the guanine-binding domain, the collapsin response mediator protein (CRMP) homology domain, and the carboxy-terminal PDZ-binding domain. Another aspect is directed to a method of regulating endogenous cypin activity in a cell comprising contacting a cell with a cypin fragment for a time sufficient to increase or decrease endogenous cypin activity in a cell. Other aspects are directed to nucleic acid molecules encoding cypin fragments, vectors comprising these nucleic acid molecules, host cells comprising these vectors, and methods of producing cypin fragments by culturing these host cells. Still another aspect is directed to antibodies that specifically bind to epitopes located in these cypin fragments. Still another aspect is directed to methods of detecting cypin or a fragment thereof in a biological sample comprising contacting a biological sample with these antibodies. Still another aspect is directed to a kit for detecting cypin or a fragment thereof in a biological sample comprising these antibodies.

These and other aspects of the present invention will be better appreciated by reference to the Detailed Description.

DETAILED DESCRIPTION

The present invention results from the unexpected discovery of several physiological functions for cypin that has not heretofore been described. This discovery has permitted the development of methods of using cypin in assays for diagnosing and monitoring cognitive disorders, as well as assays for identifying compounds to treat these disorders.

Methods for Diagnosing, Prognosing, and Monitoring the Progress of Cognitive Disorders Introduction The present invention provides methods for diagnosing cognitive disorders by detecting decreased levels of cypin. "Diagnostic" or "diagnosing" means identifying the presence or absence of a pathologic condition. Diagnostic methods involve detecting decreased levels of cypin by determining a test amount of cypin gene product (e.g., mRNA, cDNA, or polypeptide, including fragments thereof) in a biological sample from a subject (human or nonhuman mammal), and comparing the test amount with a normal amount or range (i.e., an amount or range from an individual(s) known not to suffer from a cognitive disorder) for the cypin gene product. While a particular diagnostic method may not provide a definitive diagnosis of a cognitive disorder, it suffices if the method provides a positive indication that aids in diagnosis.

The present invention also provides methods for prognosing a cognitive disorder by detecting levels of cypin. "Prognostic" or "prognosing" means predicting the probable development and/or severity of a pathologic condition. Prognostic methods involve determining the test amount of a cypin gene product in a biological sample from a subject, and comparing the test amount to a prognostic amount or range (i.e., an amount or range from individuals with varying severities of a cognitive disorder) for the cypin gene product. Various amounts of the cypin gene product in a test sample are consistent with certain prognoses for cognitive disorders. The detection of an amount of cypin gene product at a particular prognostic level provides a prognosis for the subject.

The present invention also provides methods for monitoring the course of a cognitive disorder by detecting levels of cypin. Monitoring methods involve determining the test amounts of a cypin gene product in biological samples taken from a subject at a first and second time, and comparing the amounts. A change in amount of cypin gene product between the first and second time indicates a change in the course of a cognitive disorder, with an increase in amount indicating improvement of the disorder, and a decrease in amount indicating progression of the disorder. Such monitoring assays are also useful for evaluating the efficacy of a particular therapeutic intervention (e.g., disease attenuation vs. reversal) in patients being treated for a cognitive disorder.

Biological Sample Collection

Expression of cypin can be detected in a variety of biological samples, including cells (e.g., whole cells, cell fractions, and cell extracts) and tissues. Biological samples also include sections of tissue such as biopsies and frozen sections taken for histological purposes. Preferred biological samples include blood samples, nasal biopsies, brain tissue, and spinal fluid.

Normal, Diagnostic, and Prognostic Values

In the diagnostic and prognostic assays of the present invention, the cypin gene product is detected and quantified to yield a test amount. The test amount is then compared to a normal amount or range. An amount above the normal amount or range (e.g., a 30% or greater increase (with $p<0.01$), or a 100% or greater increase (with $p<0.05$)) is a positive sign in the diagnosis of a cognitive disorder. Particular methods of detection and quantitation of cypin gene products are described below.

Normal amounts or baseline levels of cypin gene products can be determined for any particular sample type and population. Generally, baseline (normal) levels of cypin protein or mRNA are determined by measuring the amount of cypin protein or mRNA in a biological sample type from normal (i.e., healthy) subjects. Alternatively, normal values of cypin gene product can be determined by measuring the amount in healthy cells or tissues taken from the same subject from which the diseased (or possibly diseased) test cells or tissues were taken. The amount of cypin gene product (either the normal amount or the test amount) can be determined or expressed on a per cell, per total protein, or per volume basis. To determine the cell amount of a sample, one can measure the level of a constitutively expressed gene product or other gene product expressed at known levels in cells of the type from which the biological sample was taken.

It will be appreciated that the assay methods of the present invention do not necessarily require measurement of absolute values of cypin gene product because relative values are sufficient for many applications of these methods. It will also be appreciated that in addition to the quantity or abundance of cypin gene products, variant or abnormal cypin gene products or their expression patterns (e.g., mutated transcripts, truncated polypeptides) may be identified by comparison to normal gene products and expression patterns.

Assays for Cypin Gene Products

The diagnostic, prognostic, and monitoring assays of the present invention involve detecting and quantifying cypin gene products in biological samples. Cypin gene products include, for example, cypin mRNA and cypin polypeptide (or fragments thereof), and both can be measured using methods well known to those skilled in the art.

For example, cypin mRNA can be directly detected and quantified using hybridization-based assays, such as Northern hybridization, in situ hybridization, dot and slot blots, and oligonucleotide arrays. Hybridization-based assays refer to assays in which a probe nucleic acid is hybridized to a target nucleic acid. In some formats, the target, the probe, or both are immobilized. The immobilized nucleic acid may be DNA, RNA, or another oligonucleotide or polynucleotide, and may comprise naturally or nonnaturally occurring nucleotides, nucleotide analogs, or backbones. Methods of selecting nucleic acid probe sequences for use in the present invention are based on the nucleic acid sequence of cypin and are well known in the art.

Alternatively, cypin mRNA can be amplified before detection and quantitation. Such amplification-based assays are well known in the art and include polymerase chain reaction (PCR), reverse-transcription-PCR (RT-PCR), PCR-enzyme-linked immunosorbent assay (PCR-ELISA), and ligase chain reaction (LCR). Primers and probes for producing and detecting amplified cypin gene products (e.g., mRNA or cDNA) may be readily designed and produced without undue experimentation by those of skill in the art based on the nucleic acid sequence of cypin. Amplified cypin gene products may be directly analyzed, e.g., by gel electrophoresis; by hybridization to a probe nucleic acid; by sequencing; by detection of a fluorescent, phosphorescent, or radioactive signal; or by any of a variety of well-known methods. In addition, methods are known to those of skill in the art for increasing the signal produced by amplification of target nucleic acid sequences. One of skill in the art will recognize that whichever amplification method is used, a variety of quantitative methods known in the art (e.g., quantitative PCR) may be used if quantitation of cypin gene products is desired.

Cypin polypeptides (or fragments thereof) can be detected and quantified using various well-known enzymatic and immunological assays. Enzymatic assays refer to assays that utilize cypin substrates to detect guanine deaminase activity. Guanine deaminase activity can assayed by following the conversion of guanine to xanthine as described in, e.g., Yuan et al., J. Biol. Chem. 274:8175 (1999) and Paletzki, Neuroscience 109:15 (2002). Immunological assays refer to assays that utilize an antibody (e.g., polyclonal, monoclonal, chimeric, humanized, scfv, and fragments thereof) that specifically binds to a cypin polypeptide (or a fragment thereof). A number of well-established immunological assays suitable for the practice of the present invention are known, and include enzyme linked immunosorbent assay (ELISA), radioimmunoassay (RIA), immunoprecipitation, immunocytostaining, immunodiffusion, and Western blotting.

The anti-cypin antibodies to be used in the methods of the present invention can be produced by methods well known to those skilled in the art. For example, monoclonal antibodies to cypin can be produced by generation of hybridomas in accordance with known methods. Hybridomas formed in this manner are then screened using standard methods, such as ELISA, to identify one or more hybridomas that produce an antibody that specifically binds to cypin, or a fragment thereof. Full-length cypin may be used as the immunogen, or, alternatively, antigenic peptide fragments of cypin may be used. Fragments of particular interest missing various cypin domains or encompassing various domains are described below. Such fragments can be used in assays, e.g., ELISAs, to identify antibodies that bind epitopes in specific domains of cypin, including the zinc-binding aminohydrolase domain, guanine binding domain, the collapsin response mediator protein (CRMP) homology domain and the carboxy-terminal PDZ-binding domain (see Akum et al., Nature Neurosci. 7:145 (2004).

As an alternative to preparing monoclonal antibody-secreting hybridomas, a monoclonal antibody to cypin, or a fragment thereof, may be identified and isolated by screening a recombinant combinatorial immunoglobulin library (e.g., an antibody phage display library) to thereby isolate immunoglobulin library members that bind to cypin, or a fragment thereof. Kits for generating and screening phage display libraries are commercially available from, e.g., Dyax Corp. (Cambridge, Mass.) and Maxim Biotech (South San Francisco, Calif.). Additionally, examples of methods and reagents particularly amenable for use in generating and screening antibody display libraries can be found in the literature.

Polyclonal sera and antibodies may be produced by immunizing a suitable subject, such as a rabbit, with cypin (preferably mammalian; more preferably human) or an antigenic fragment thereof. The antibody titer in the immunized subject may be monitored over time by standard techniques, such as with ELISA, using immobilized marker protein. If desired, the antibody molecules directed against cypin may be isolated from the subject or culture media and further purified by well-known techniques, such as protein A chromatography, to obtain an IgG fraction, or by affinity chromatography, as described in Firestein et al., Neuron 24:659 (1999).

Fragments of antibodies to cypin may be produced by cleavage of the antibodies in accordance with methods well known in the art. For example, immunologically active F(ab') and F(ab')$_2$ fragments may be generated by treating the antibodies with an enzyme such as pepsin. Additionally, chimeric, humanized, and single-chain antibodies to cypin, comprising both human and nonhuman portions, may be produced using standard recombinant DNA techniques. Humanized antibodies to cypin may also be produced using transgenic mice that are incapable of expressing endogenous immunoglobulin heavy and light chain genes, but which can express human heavy and light chain genes.

In the immunological assays of the present invention, the cypin polypeptide is typically detected directly (i.e., the anti-cypin antibody is labeled) or indirectly (i.e., a secondary antibody that recognizes the anti-cypin antibody is labeled) using a detectable label. The particular label or detectable group used in the assay is usually not critical, as long as it does not significantly interfere with the specific binding of the antibodies used in the assay.

The immunological assays of the present invention may be competitive or noncompetitive. In competitive assays, the amount of cypin in a sample is measured indirectly by measuring the amount of added (exogenous) cypin displaced from a capture agent (i.e., an anti-cypin antibody) by the cypin in the sample. In noncompetitive assays, the amount of cypin in a sample is directly measured. In a preferred noncompetitive "sandwich" assay, the capture agent (e.g., a first anti-cypin antibody) is bound directly to a solid support (e.g., membrane, microtiter plate, test tube, dipistick, glass or plastic bead) where it is immobilized. The immobilized agent then captures any cypin polypeptide present in the sample. The immobilized cypin can then be detected using a second labeled anti-cypin antibody. Alternatively, the second anti-cypin antibody can be detected using a labeled secondary antibody that recognizes the second anti-cypin antibody.

Kits

The methods and reagents of the present invention can be conveniently packaged in kit form. Such kits can be used in the diagnostic, prognostic, and monitoring methods described above. For example, such kits may include an anti-cypin antibody (or fragment thereof) and a control antibody that does not react with cypin, as well as instructional materials for using the kits to detect cypin. Such kits may also include a substantially isolated cypin polypeptide (or fragment thereof) comprising an epitope which is specifically immunoreactive with at least one anti-cypin antibody, which may be bound to a solid support (e.g., slides, chips, membranes, beads, microtiter plates, etc.). Further, such kits may include means for detecting the binding of the anti-cypin antibody (or fragment thereof) to cypin in a biological sample (e.g., the anti-cypin antibody may be conjugated to a fluorescent compound such as fluorescein or rhodamine, or a second labeled antibody may be included that binds to anti-cypin). The kits may also include hybridization and wash solutions, buffers, salts, nuclease-free water, containers, vials, reaction tubes, cover slips, various signal-detecting, signal-producing, signal-enhancing, and signal-preserving reagents, and the like compatible with the use of the kits to detect cypin.

While the instructional materials typically comprise written or printed materials, they are not limited to such. Any medium capable of storing such instructions and communicating them to an end user is contemplated by this invention. Such media include, but are not limited to, electronic storage media (e.g., magnetic discs, tapes, cartridges, chips), optical media (e.g., CD ROM), and the like. Such media may include addresses to internet sites that provide such instructional materials.

Screening Methods for Identifying Compounds that Increase Cypin Expression and/or Activity Introduction As described below, increased cypin expression and activity in neurons correlates with dendrite number and branching, whereas decreased cypin levels correlates with decreased dendrite number and branching. This regulation of dendrites is due in part to cypin's guanine deaminase activity. Accordingly, the present invention provides methods (also referred to herein as "screening assays") for identifying novel compounds that increase the expression or activity of cypin. In one embodiment, cells that are capable of expressing cypin (preferably neurons) are contacted with a test compound to determine whether the compound increases expression of a cypin gene product (e.g., mRNA or polypeptide). Changes in cypin gene expression can be determined by any method known in the art or described above. The changes in expression can be correlated with morphological changes associated with cypin activity, such as dendrite number and branching. Compounds identified that increase cypin expression (either mRNA or polypeptide) are candidates as drugs for the prophylactic and therapeutic treatment of cognitive disorders.

Alternatively, compounds can be identified that increase the activity of cypin. Such compounds are considered agonists of cypin. Generally, a method for identifying an agonist of cypin comprises: (a) providing a sample comprising a cypin polypeptide or fragment thereof; (b) contacting said sample with a candidate agent to be tested for cypin agonistic activity; and (c) measuring the activity of cypin polypeptide or fragment thereof, whereby a cypin agonist is identified by measurement of an increase in activity as compared to the activity measured in the absence of such agonist. Cypin (or a fragment thereof) can be contacted with a test compound to determine whether the compound increases the activity of cypin (as compared to an untreated sample of cypin). Compounds identified that increase cypin activity can then be tested in in vitro and in vivo models of cognitive disorders, such as the Rett syndrome mouse (MeCP2 knockout mouse), the Lesch-Nyhan Disease mouse (HPRT knockout mouse), the Alzheimers Disease rat model, etc.

Generally, a plurality of assays can be run in parallel with different agent concentrations to obtain a differential response to the various concentrations. Typically, one of these concentrations serves as a negative control, i.e., at zero concentration or below the level of detection. In addition, candidate agents can be contacted with a non-cypin molecule as a control for target specificity. Although the screening methods are generally used as an assay to identify previously unknown molecules that can act as a therapeutic agent, the method can also be used to confirm and standardize the desired activity of known cypin agonists or to optimize the structure and/or activity of a known cypin agonist during, e.g., molecular evolution procedures.

The screening assays used to identify cypin agonists can be either cell-based or cell-free assays. Cell-free assays are preferred because they are easily adaptable to high-throughput screening procedures (e.g., BIACORE™ (Biacore International AB, Uppsala, Sweden), BRET (bioluminescence resonance energy transfer), FRET (fluorescence resonance energy transfer), ELISA, spectrophotometric tubulin binding and tubulin polymerization assays, etc.). For example, samples containing purified or partially purified cypin can be contacted with one of a plurality of test compounds, and the activity of cypin in each of the treated samples can be compared to the activity of cypin in untreated samples or in samples contacted with different test compounds to determine whether any of the test compounds provides a substantially increased level of cypin activity, thereby identifying an agonist of cypin activity.

Any activity associated with cypin (or a fragment thereof) can be assayed in the screening methods. Such cypin activity includes, but is not limited to, dendrite formation, dendrite branching, guanine deaminase activity, guanine binding, microtubule formation, tubulin binding, and binding to proteins containing PDZ domains (e.g., PSD-95). For binding activities, a reaction mixture is generally first prepared containing cypin (or a binding domain thereof) and its binding partner (e.g., tubulin, PDZ, etc.) under conditions and for a time sufficient to allow the two to interact and bind, thus forming a complex. The increased rate of formation of a complex in the reaction mixture containing the test compound compared to the control reaction indicates that the compound is an agonist of the cypin. Compounds that are so identified can then be further evaluated for their ability to increase dendritic formation and/or branching in cell-based assays.

The screenings assays described herein can also be used to identify compounds that decrease activity of cypin (i.e., antagonists). For example, samples containing purified or partially purified cypin can be contacted with one of a plurality of test compounds, and the activity of cypin in each of the treated samples can be compared to the activity of cypin in untreated samples or in samples contacted with different test compounds to determine whether any of the test compounds provides a substantially decreased level of cypin activity, thereby indicating an antagonist of cypin activity.

Compounds identified that increase or decrease cypin expression and/or activity can be tested in cell-based assays to determine their effect on cell morphology. Preferably, the compounds are contacted with cells capable of forming dendrites (such as neurons) to determine the effect on dendrite formation and/or branching.

Sources of Cypin

Any cypin can be used in the methods of the present invention. The amino acid sequences of various cypin polypeptides are publicly available from Genbank and include human (Acc. No. NP_004284; SEQ ID NO: 1), orangutan (Acc. No. CAH91101; SEQ ID NO: 3); rat (Acc. No. AAF63337; SEQ ID NO: 5) and mouse (Acc. No. NP_034396; SEQ ID NO: 7). The cypin can be isolated from natural sources, produced by recombinant methods, or produced through in vitro protein synthesis. Thus, the present invention does not require that cypin be naturally occurring. Analogs of cypin that are functionally equivalent in terms of possessing any one or more of above-described activities may also be used. Thus, representative analogs include fragments of cypin that possess, e.g., dendrite formation activity, dendrite branching activity, guanine deaminase activity, microtubule formation activity, tubulin binding activity and/or PDZ domain binding activity.

Other than fragments of cypin, analogs may differ from the naturally occurring protein in terms of one or more amino acid substitutions, deletions, additions, or rearrangements. For example, functionally equivalent amino acid residues may be substituted for residues within the sequence resulting in a change of sequence. Such substitutes may be selected from other members of the class to which the amino acid belongs: e.g., the nonpolar (hydrophobic) amino acids include alanine, leucine, isoleucine, valine, proline, phenylalanine, tryptophan, and methionine; the polar neutral amino acids include glycine, serine, threonine, cysteine, tyrosine, asparagine, and glutamine; the positively charged (basic) amino acids include arginine, lysine, and histidine; the negatively charged (acidic) amino acids include aspartic acid and glutamic acid.

Cypin can be purified or partially purified from various tissues (preferably mammalian; more preferably human), including brain, bone, cervix, colon, eye, kidney, liver, lung, mammary gland, muscle, ovary, pancreas, placenta, small intestine, stomach, tongue, testis, uterus and erythrocytes, using known purification processes such as gel filtration and ion exchange chromatography. Purification may also include affinity chromatography with agents known to bind cypin (e.g., anti-cypin antibodies, tubulin, PSD-95, etc.). These purification processes may also be used to purify cypin (or fragments thereof) from recombinant sources.

Once purified, the cleavage of the cypin into fragments of amino acid residues can be achieved using proteolytic enzymes such as thrombin or clostridiopeptidase B (clostripain). The exact time required for proteolysis varies with each cypin and markedly depends upon the batch of clostripain used. Therefore, the optimum time for a single cleavage must be determined for each combination of clostripain batch and cypin used. The cypin fragments resulting from either thrombin or clostripain proteolysis may be further cleaved by digestion with trypsin, which cleaves on the carboxy terminus of lysine or arginine residues.

The sequence of cypin derived from proteolytic digestion may be identified using the Edman degradation method of protein sequencing. In addition, sequence analysis of cypin may be accelerated by using an automated liquid phase amino acid sequenator, thereby allowing for the analysis of picomolar quantities of cypin containing up to 50 amino acid residues in length.

The production of cypin can also be achieved by recombinant DNA technology. Nucleic acid sequences encoding cypin (or fragments thereof) can be produced using methods well known in the art, including chemical synthesis and PCR. Nucleic acid sequences encoding cypin polypeptides from various species as set forth in SEQ ID NOs: 1, 3, 5 and 7 are publicly available from Genbank and include human (Acc. No. NM_004293; SEQ ID NO: 2), orangutan (Acc. No. CR858902; SEQ ID NO: 4); rat (Acc. No. AF245172; SEQ ID NO: 6) and mouse (Acc. No. NM_010266; SEQ ID NO: 8). Due to the degeneracy of the genetic code, many different nucleotide sequences can encode the cypin polypeptides of SEQ ID NOs: 1, 3, 5 and 7. The codons can be selected for optimal expression in prokaryotic or eukaryotic systems. Homologous sequences (both paralogues and orthologues) can also be used so long as they retain the structure and/or activity of cypin. Methods for identifying homologous nucleic acid and amino acid sequences are well known in the art and include both hybridization-based and bioinformatics-based approaches (see Baxevanis and Ouellette, Bioinformatics, A Practical Guide to the Analysis of Genes and Proteins (2001)).

Recombinant DNA technology is particularly suited to the production of active fragments of cypin. Applicant has identified several cypin fragments of interest that can be used in the methods of the present invention. By "fragment" is meant any portion of cypin smaller than the full-length protein, whether the deleted portion is at an end or in the middle of cypin. Such fragments find utility as antigens for antibody production, targets for screening assays, therapeutical compounds, and regulators (e.g., activators and inhibitors) of endogenous cypin polypeptide activity.

One such cypin fragment comprises a deletion of its zinc-binding aminohydrolase domain (e.g., a deletion amino acids 76-84 of SEQ ID NOs: 1, 3, 5 and 7, as represented by SEQ ID NOs. 9-12, respectively); a deletion of amino acids 1-220 of SEQ ID NOs: 1, 3, 5 and 7). Another cypin fragment comprises a deletion of its guanine-binding domain (e.g., a deletion of amino acids 233-250 of SEQ ID NOs: 1, 3, 5 and 7, as represented by SEQ ID NOs. 13-16, respectively). Another cypin fragment comprises a deletion of its collapsin response mediator protein (CRMP) homology domain (e.g., a deletion of amino acids 350-403 of SEQ ID NOs: 1, 3, 5 and 7 as represented by SEQ ID NOs. 17-20, respectively). Another cypin fragment comprises a deletion of its carboxy-terminal PDZ-binding domain (e.g., a deletion of amino acids 451-454 of SEQ ID NOs: 1, 3, 5 and 7). Another cypin fragment comprises a deletion of its zinc-binding aminohydrolase domain and its guanine-binding domain (e.g., a deletion of amino acids 1-349 of SEQ ID NOs: 1, 3, 5 and 7). Another cypin fragment comprises a deletion of its guanine-binding domain and its collapsin response mediator protein (CRMP) homology domain (e.g., a deletion of amino acids 101-450 of SEQ ID NOs: 1, 3, 5 and 7, as represented by SEQ ID NOs. 21-24, respectively). Another cypin fragment comprises a deletion of its guanine-binding domain, its collapsin response mediator protein (CRMP) homology domain, and its carboxy-terminal PDZ-binding domain (e.g., a deletion of amino acids 221-454 of SEQ ID NOs: 1, 3, 5 and 7).

Insertion of a nucleic acid sequence encoding a cypin polypeptide (or fragment thereof) into a vector is readily accomplished when the termini of the nucleic acid sequence and the vector comprise compatible restriction sites. If this cannot be done, it may be necessary to modify the termini of the nucleic acid and/or vector by digesting back single-stranded DNA overhangs generated by restriction endonuclease cleavage to produce blunt ends, or to achieve the same result by filling in the single-stranded termini with an appropriate DNA polymerase. Alternatively, desired sites may be produced, e.g., by ligating nucleotide sequences (linkers) onto the termini. Such linkers may comprise specific oligonucleotide sequences that define desired restriction sites. Restriction sites can also be generated by the use of PCR. The cleaved vector and the DNA fragments may also be modified if required by homopolymeric tailing.

Recombinant expression vectors for expression of cypin (or fragments thereof) are typically self-replicating DNA constructs comprising a nucleic acid sequence encoding a cypin polypeptide (or fragment thereof) operably linked to a suitable genetic control element that is capable of regulating expression of the nucleic acids in a compatible hosts cell. Genetic control elements may include a prokaryotic promoter system or a eukaryotic promoter expression control system, and typically include a transcriptional promoter, an optional operator to control the onset of transcription, transcription enhancers to elevate the level of mRNA expression, a sequence that encodes a suitable ribosome binding site, and sequences that terminate transcription and translation. Expression vectors also may contain an origin of replication that allows the vector to replicate independently of the host cell.

Suitable prokaryotic promoters include the β-lactamase and lactose promoter systems, the tryptophan (trp) promoter system, the lambda $P_L$ promoter system and the tac promoter. Numerous expression vectors containing such control sequences are known in the art and available commercially. Suitable eukaryotic promoters include the cytomegalovirus (CMV) promoter, the SV40 early promoter region, the promoter contained in the 3' long terminal repeat of Rous sarcoma virus (RSV), the herpes TK promoter, the adenoviral promoter of an early or late (E1A, MLP, etc.) gene, the regulatory sequences of the metallothionein (MT) and phosphoglycerokinase (PGK) genes, as well as cypin promoters themselves.

Suitable host cells for expressing a nucleic acid sequence encoding a cypin polypeptide (or fragment thereof) include prokaryotes and lower eukaryotes. Suitable prokaryotes include both gram negative and positive organisms, e.g., *E. coli* and *B. subtilis, S. typhimurium*, or any bacterial strain capable of expressing heterologous proteins. Suitable lower eukaryotes include yeast strains such *S. cerevisiae, S. pombe, Kluyveromyces strains, Candida*, or any yeast strain capable of expressing heterologous proteins. If the protein is made in yeast or bacteria, it may be necessary to modify the protein produced therein, for example by phosphorylation or glycosylation of the appropriate sites, or by introduction of the targeting sequences, in order to obtain a functional protein. Such covalent attachments may be accomplished using known chemical or enzymatic methods.

The host cell is preferably a higher eukaryote cell line. Suitable higher eukaryote cell lines include both primary and established cell lines from animal cells, both of non-mammalian origin, e.g., insect cells and birds, and of mammalian origin, e.g., human, primates, and rodents.

Higher eukaryotic tissue culture cells are preferred hosts for the recombinant production of a cypin polypeptide (or fragment thereof). Although any higher eukaryotic tissue culture cell line might be used, including insect baculovirus expression systems, mammalian cells are preferred. Suitable mammalian cell lines include HeLa cells, Chinese hamster ovary (CHO) cells, baby rat kidney (BRK) cells, baby hamster kidney (BHK) cells, African green monkey kidney (COS and CV-1) cells, human embryonic kidney (HEK 293) cells, A431 cells, Colo205 cells, 3T3 cells, mouse L cells, HL-60 cells, U937 cells, HaK cells, Jurkat cells, Madin Darby Canine Kidney (MCDK) cells, and PC12 cells. Preferably, the cell line is capable of dendrite formation and/or branching, such as PC12 cells treated with NGF. Primary cultures of rat and mouse meurons are most preferable.

Methods for the transformation or transfection of such cells are well known in the art and include electroporation, calcium phosphate co-precipitation, protoplast or spheroplast fusion, lipofection, DEAE-dextran-mediated transfection, biolistics, and viral infection. The transfected expression vector can be maintained transiently in the cell. Alternatively, if the expression vector contains a selectable marker, cells can be selected in which the vector has stably integrated into the genome by culturing the transfected cells in the appropriate antibiotic or drug. Suitable dominant selectable markers include the bacterial aminoglycoside 3' phosphotransferase gene (also referred to as the neo gene) which confers resistance to the drug G418 in mammalian cells, the bacterial hygromycin G phosphotransferase (hyg) gene which confers resistance to the antibiotic hygromycin, and the bacterial xanthine-guanine phosphoribosyl transferase gene (also referred to as the gpt gene) which confers the ability to grow in the presence of mycophenolic acid.

In order to facilitate purification, cypin (or fragments thereof) may be recombinantly expressed as fusions with proteins such as maltose-binding protein (MBP), glutathione-S-transferase (GST), thioredoxin (TRX) or $His_6$. Kits for expression and purification of such fusion proteins are commercially available from New England BioLabs (Beverly, Mass.), Pharmacia (Piscataway, N.J.), and Invitrogen (Carlsbad, Calif.). Cypin can also be tagged with a small epitope, such as FLAG, HA, T7 or au5, and subsequently identified or purified using a specific antibody to the epitope. One such epitope is the FLAG epitope, which is commercially available from Eastman Kodak (New Haven, Conn.). Cypin (or fragments thereof) can also be fused to marker proteins, such as β-galactosidase, green fluorescent protein and variants (yellow, cyan), DsRed proteins, monomeric red fluorescent protein, and luciferase to facilitate localization in situ. Fusions to fluorescent and luminescent proteins also facilitate the use of high-throughput screening assays, such as BRET and FRET, described above.

Cypin (or fragments thereof) may also be produced by known conventional chemical synthesis. Methods for chemically synthesizing polypeptides are well known to those skilled in the art. Such chemically synthetic cypin should possess biological properties in common with the naturally produced form, and thus can be employed as a biologically active or immunological substitute for natural cypin.

Sources of Test Compounds

Any candidate agent or compound can be screened in the above-described methods. Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including, but not limited to, peptides, saccharides, fatty acids, steroids, purines, pyrimidines, and various derivatives, structural analogs and combinations thereof. Preferably, the candidate agent is a small organic compound capable of crossing the blood brain barrier, such as a benzodiazapene, a biphenyl, or heterocycles in general.

Candidate agents can be obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc., to produce structural analogs. Any compounds identified can serve as conventional "lead compounds" or can be used as the actual therapeutics for treatment of cognitive disorders.

Methods of Treatment

Introduction

The present invention provides both prophylactic and therapeutic methods for the treatment of cognitive disorders by increasing expression and/or activity of cypin. The methods generally involve contacting cells (either in vitro, in vivo, or ex vivo) with an agent in an amount effective to increase expression and/or activity of cypin. Any cell can be contacted, preferably a cell capable of forming primary and/or secondary dendrites, such as neurons. When cells are contacted in vivo or ex vivo, the methods can also be described as "methods for treating a subject". Any subject that suffers from a cognitive disorder can be treated, preferably mammalian, more preferably human.

Administration

In one embodiment, the agent contacted is a cypin polypeptide (or fragment thereof). For example, attaching a cypin polypeptide (or a fragment thereof) to cell permeable peptides, such as antennapaedia or Tat will allow cypin to cross the cell membrane. "Contacting with a cypin polypeptide (or fragment thereof)" can also be accomplished by transfection of a recombinant expression vector comprising a nucleic acid molecule encoding a cypin polypeptide (or fragment thereof) using any of the methods described above or, e.g., by inhalation of a liposome formulation containing such a vector through the nasal cavity for direct access to the brain.

In another embodiment, the agent is a compound that activates dendrite formation and/or branching, such as KCl or various neurotrphins, such as NGF or BDNF. Alternatively, the agent is a compound that increases the intracellular stores of guanine, be it guanine itself, a soluble guanine analog, such as acetoxyacetyl- or methoxyacetylguanine, or some other compound.

In a further embodiment, the agent is any one or more of the novel compounds identified by the screening methods described above that increases expression and/or activity of cypin.

All such compounds described herein can be administered in vivo in the form of a pharmaceutical composition for the treatment of a cognitive disorder. The pharmaceutical compositions may be administered by any number of routes, including, but not limited to, oral, nasal, rectal, topical, sublingual, intravenous, intramuscular, intraarterial, intramedullary, intrathecal, intraventricular, intraperitoneal, intraarticular, or transdermal routes. In addition to the active ingredients, the pharmaceutical compositions may contain pharmaceutically acceptable carriers comprising excipients, coatings, and auxiliaries known in the art.

For preparing pharmaceutical compositions from the compounds described above, inert, pharmaceutically acceptable carriers can be either solid or liquid. Solid form preparations include powders, tablets, dispersible granules, capsules, cachets, suppositories and liposomes. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds may also be deliverable transdermally. The transdermal compositions can take the form of creams, lotions, aerosols and/or emulsions and can be included in a transdermal patch of the matrix or reservoir type as are conventional in the art for this purpose.

The compounds may also be delivered subcutaneously. Preferably the compounds are administered orally or nasally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 100 mg, preferably from about 1 mg to about 50 mg, more preferably from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compound and/or the pharmaceutically acceptable salts thereof will be regulated according to the judgment of the attending clinician considering such factors as age, condition and size of the patient, the severity of the symptoms being treated, and the toxicity profile of the compound.

For any compound, the therapeutically effective dose can be estimated initially either in cell culture or in animal models. The therapeutically effective dose refers to the amount of active ingredient that ameliorates the condition or its symptoms. Therapeutic efficacy and toxicity in cell cultures or animal models may be determined by standard pharmaceutical procedures (e.g., $ED_{50}$: the dose therapeutically effective in 50% of the population; $LD_{50}$: the dose lethal to 50% of the population). The dose ratio between therapeutic and toxic effects is the therapeutic index, and can be expressed as the ratio $ED_{50}/LD_{50}$. Pharmaceutical compositions that exhibit large therapeutic indexes are preferred.

The data obtained from cell culture and animal models can then be used to formulate a range of dosage for the compound for use in mammals, preferably humans. The dosage of such a compound preferably lies within a range of concentrations that include the $ED_{50}$ with little to no toxicity. The dosage may vary within this range depending upon the composition form employed and the administration route utilized. A typical recommended daily dosage regimen will generally range from about 0.001 mg/day to about 1000 mg/day, preferably from about 0.1 to 300 mg/day, more preferably from about 1 mg/day to 50 mg/day, in two to four divided doses.

Specific embodiments according to the methods of the present invention will now be described in the following examples. Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

EXAMPLES

Example 1

Cypin Immunolocalization in Cultured Hippocampal Neurons

Cypin is a recently identified guanine deaminase that perturbs post-synaptic trafficking of (membrane associated guanylate kinase) MAGUK proteins, such as PSD-95 and SAP-102 (Firestein et al., Neuron 24:659 (1999)), which play a role in the maturation of excitatory synapses (El-Hussein, et al., Science 290:364 (2000)). Cypin interacts with the first and second PDZ domains of PSD-95 via a carboxy-terminal canonical PDZ-binding domain (SSSV) (Firestein et al., Neuron 24:659 (1999)).

To establish cypin's role in neuronal development, rat hippocampal neurons were cultured and immunohistochemistry performed using an antibody that was raised against cypin (Id.). This antibody was shown to be specific for cypin protein. Cypin was expressed early in culture and continued to be expressed as neurons matured (Id.). Cultures were also co-stained using an antibody raised against MAP2, a marker of dendrites, to determine the localization of cypin protein. Cypin was expressed in developing dendrites and increased its expression in axons as the neurons matured (Id.). Similar localization was shown in neurons in the adult cortex, hippocampus, striatum, and superior colliculus (Id.).

Example 2

Regions of Cypin Involved in Guanine Deaminase Activity

Cypin shares a nine amino acid sequence (PGX(V/I)DXH(T/V/I)H), located at amino acid residues 76-84, found in other aminohydrolases and amidohydrolases, including 28 enzymes from 20 different species (Yuan. et al., J. Biol. Chem. 274:8175 (1999); Karlin et al., Proc. Nat'l. Acad. Sci. USA, 94:14231 (1997); Akum et al., Nature Neurosci. 7:145 (2004)). This short motif is believed to be important for zinc binding. Cypin also contains a region at amino acids 350-403 highly homologous to the collapsin-response mediator protein (CRMP) family and the *C. elegans* unc-33 gene (Akum et al., Nature Neurosci. 7:145 (2004)). Recent evidence suggests that CRMP-2 directly binds to tubulin heterodimers and promotes microtubule assembly (Gu et al., J. Biol. Chem 275:17917 (2000); Fukata et al., Nat. Cell Biol. 4:583 (2002)) and that overexpression of CRMP-2 induces multiple axon formation (Inagaki et al., Nat. Neurosci. 4:781 (2001)). Cypin also contains a canonical PDZ-binding sequence (SSSV) at its carboxyl terminus (amino acids 451-454) (Akum et al., Nature Neurosci. 7:145 (2004)).

To define which of these domains play a role in guanine deaminase activity, cDNAs encoding N-terminal green fluorescent protein (GFP) fusions of deletion mutants of rat cypin (cypin-GFP) were constructed using site-directed mutogenesis or PCR (Id.). COS-7 cells were then transfected with the cDNAs and assayed for guanine deaminase activity using a colorimetric assay as described in Paletzki, Neuroscience 109:15 (2002). The deletion of either the zinc-binding domain (amino acids 76-84) (cypin(Δ76-84)-GFP) or the CRMP-homology domain (amino acids 350-403) (cypinΔ(350-403)-GFP) attenuated guanine deaminase activity (Id.). If the assay was allowed to progress for a longer period of time, cypinΔ(350-403)-GFP did show some activity, suggesting that the CRMP homology domain may play a role in modulating guanine deaminase activity (Id.). Furthermore, both domains are necessary for normal activity since truncation mutants of cypin containing either the first 100 amino acids of cypin fused to the PDZ binding domain (cypin(1-100)SSSV-GFP) or cypin lacking the first 349 amino acids (cypin(350-end)-GFP) did not have guanine deaminase activity (Id.). Deleting the PDZ-binding motif alone (cypin-PDZ-GFP) had no effect on cypin's enzymatic activity (Id.).

Example 3

Cypin Increases Primary and Secondary Dendrite Number

Cypin is expressed in the dendrites and axons of developing neurons and has high homology to the region of CRMP that binds to tubulin heterodimers. To establish that overexpression of cypin would have an effect on dendrite or axon outgrowth, rat hippocampal neurons were transfected at 10 days in vitro (d.i.v.), a time at which dendrite branching is occurring, with a cDNA encoding rat cypin-GFP, and dendrite number was assessed by co-staining with an antibody raised against MAP-2. Axons were identified as being MAP-2 negative. Overexpression of cypin resulted in a significant increase in both primary and secondary dendrites (Akum et al., Nature Neurosci. 7:145 (2004)). There was no effect on axon number (Id.).

To establish that this was not a transient effect of cypin during development, the same experiment was performed with cypin overexpression occurring from 10-17 d.i.v. The number of dendrites was quantitated on d.i.v. 17, when neurons are mature and spines are beginning to form. Consistent with the previous results, cypin-GFP increased primary and secondary dendrite number at this time point. However, the number of primary dendrites at 17 d.i.v. was reduced when compared with that of 12 d.i.v. Furthermore, there appeared to be excessive pruning of secondary dendrites in cultures from 12 d.i.v. to 17 d.i.v. for neurons that overexpressed cypin-PDZ-GFP, a mutant version of cypin that lacks the interaction motif for PSD-95 (Akum, et al., (2004)). Thus, the binding of PSD-95 to cypin has a role in establishing and maintaining stable secondary dendrites.

To determine whether the increase in dendrite number was due to cypin's guanine deaminase activity, rat hippocampal neurons were transfected with cDNAs encoding cypin-PDZ-GFP, cypinΔ(76-84)-GFP, cypinΔ(350-403)-GFP, cypin(1-100)SSSV-GFP, or cypin(350-end)-GFP. The only mutant that retained normal guanine deaminase activity, cypin-PDZ-GFP, increased primary and secondary dendrite number at 12 d.i.v. (Id.). The mutants that did not have guanine deaminase activity did not increase dendrite number at 12 or 17 d.i.v. Furthermore, since this mutant cannot bind MAGUK proteins because it lacks its PDZ-binding domain, increase in dendrite number was independent of MAGUK binding. In fact, both cypinΔ76-84)-GFP and cypinΔ (350-403)-GFP acted as dominant negative proteins, resulting in decreased secondary dendrite number at 12 d.i.v. (Id.). Although not significant, expression of cypin(1-100)SSSV-GFP and cypin(350-end)-GFP appeared to decrease secondary dendrite number (Id.). It is important to note that all constructs express at similar levels (P>0.05 by ANOVA followed by Bonferroni Multiple Comparisons Test as compared to cypin-GFP; mean fluorescence intensities are as follows: GFP=880.97±103.54; cypin-GFP=701.28±119.72; cypinΔ(76-84)-GFP=627.23±121.10; cypinΔ350-403)-GFP=368.89±85.83; cypin(1-100)SSSV-GFP=840.19±144.03; cypin (350-end)-GFP=991.34±281.61; cypin-PDZ-GFP=705.76±94.53).

As overexpression of cypin resulted in increased dendrite branching, a novel knockdown strategy based on U1 snRNA (Fortes et al., Proc. Nat'l. Acad. Sci. USA 100:8264 (2003) was employed to determine whether attenuation of cypin would result in decreased dendrite in cultured neurons. To knock down cypin in cultured hippocampal neurons, three plasmids were constructed that encode U1 snRNAs where the 5' end is complementary to part of cypin pre-mRNA. Constructs U1-1302 and U1-1338 contained 10 base pair sequences that correspond to the carboxyl terminal end of the coding region of cypin. Construct U1-3'UTR contained 10 bases that correspond to the 5' end of the 3'UTR of cypin. Construct 702 was vector alone. These constructs also expressed GFP off a separate promoter, which served as a marker for expression. Cultured rat hippocampal neurons on 10 d.i.v. were transfected with the constructs and fixed and immunostained for cypin 48 hours post-transfection, at which time the neurons were alive, had dendrites and contained only one axon (as is true at 17 div.). Constructs U1-1302 and U1-3'UTR attenuated cypin protein expression to levels below or at the threshold of detection in two-thirds of transfected neurons (Akum et al., Nature Neurosci. 7:145 (2004)). Construct U1-1338 did not attenuate cypin protein expression (Id.). Further analysis showed that knocking down cypin protein expression significantly decreased dendrite number (Id.). Quantification of fluorescence established a correlation between intensity and dendrite number (Id.).

To address issues that the mutated U1 snRNA had nonspecific effects and attenuated expression of other proteins, leading to decreased dendrite number, a plasmid that expressed both cypin-GFP lacking the 3'UTR (U1 recognition site) and U1-3'UTR was constructed. In this circumstance, cypin-GFP served to rescue the phenotype seen when the mutated U1 snRNA specifically knocked down cypin protein expression (Id.). Since dendrite numbers returned to control values, the amount of cypin-GFP that was produced from the U1-3'UTR+cypin plasmid replaced the endogenous cypin that had been knocked out. Together with the overexpression studies, these data suggest that the guanine deaminase activity of cypin plays a role in regulating dendrite branching.

If cypin plays an important role in regulating dendrite morphology as neurons mature, knocking down cypin protein levels should result in decreased primary and secondary dendrites in mature neurons 17 d.i.v. Indeed this was the case. Furthermore, replacing endogenous cypin with cypin-GFP rescued dendrite number as it did at 12 d.i.v. (Id.). Our results indicate that cypin levels regulate dendrite number in mature neurons.

Example 4

Cypin does not Merely Change Global Guanine Nucleotides

Because cypin is a guanine deaminase, metabolism of guanine by cypin could affect dendrite branching by changing the global levels of guanine nucleotides in neurons. A decrease in GTP in turn could result in decreased activity of small GTPases that are involved in dendrite branching. To address whether cypin regulates dendrite number by this mechanism, dominant negative forms of RhoA, Rac1, and Cdc42 were expressed in rat hippocampal neurons at 10 d.i.v. Expression of these mutants did not change the number of dendrites (Akum et al., Nature Neurosci. 7:145 (2004)). Co-expression of these dominant negative proteins with rat cypin-GFP prevented the cypin-mediated increase in primary and secondary dendrite number (Id.). Results with dominant negative GTPases (decreased or no change in branching) gave the opposite result of cypin overexpression (increased branching), which is inconsistent with a model in which cypin causes dendritic branching by simply depleting the global pool of GTP, and thereby decreasing small GTPase activity as a secondary consequence. Furthermore, if cypin globally changed the activity of small GTPases, changes in axon number would be expected (Bito et al., Neuron 26:431 (2000); Ellezam et al., Prog. Brain Res. 137:371 (2002)), which was not the case. It is possible, however, that cypin may regulate local levels of guanine nucleotides to act through cdc42 and RhoA.

Example 5

Cypin Binds Directly to Tubulin Heterodimers

Cypin contains a region of homology to CRMP that binds directly to tubulin heterodimers (Akum et al., Nature Neurosci. 7:145 (2004)). To establish that cypin binds to tubulin, affinity chromatography was performed using a GST fusion of rat cypin immobilized on glutathione beads incubated with rat brain extract. The eluate was then assayed for the presence of tubulin. Whereas GST alone did not bind tubulin, immobilized cypin did bind tubulin (Id.). To assess whether this interaction occurs in vivo, rat brain extract was subjected to immunoprecipitation with preimmune serum or polyclonal antibody raised against cypin. Tubulin was found in the cypin immunoprecipitates (Id.). Very little tubulin was present when preimmune serum is used, representing nonspecific binding (Id.). Furthermore, no tau was detected in the cypin immunoprecipitates, supporting the idea that cypin binds specifically to tubulin and not all cytoskeletal proteins (Id.). In addition, cypin was found in tubulin immunoprecipitates. This indicates that cypin binds to tubulin in the brain.

Based on homology to CRMP, it was hypothesized that cypin binds directly to tubulin heterodimers. To establish that there is a direct interaction, purified cypin was incubated with tubulin heterodimers and the mixtures subjected to immunoprecipitation with an antibody raised against tubulin. Cypin indeed coimmunoprecipitated with tubulin (Id.). To identify which region of cypin binds to tubulin heterodimers, regions of cypin were purified. As predicted, the first 220 amino acids of cypin (cypin(1-220)), lacking the CRMP region, did not bind to tubulin (Id.). Only when the CRMP region is present (wild-type cypin, cypin(220-end), or cypin(350-end), did cypin co-immunoprecipitate with tubulin heterodimers (Id.). This indicates that the CRMP region mediates the binding of cypin to tubulin heterodimers.

Example 6

Cypin Promotes Microtubule Assembly

As cypin does not increase dendrite number by altering global pools of guanine nucleotides, it was hypothesized that cypin regulates neuronal morphology by promoting microtubule assembly. In fact, it has been shown that CRMP induces multiple axon formation by promoting microtubule assembly. (Inagaki et al., Nat. Neurosci. 4:781 (2001)). Microtubule formation was assayed in the presence of purified GST or GST-cypin, and it was found that cypin promoted microtubule assembly while GST did not (Akum et al., Nature Neurosci. 7:145 (2004)). Furthermore, microtubule assembly was not replicated by merely using amino acids 350-end of cypin (Id.), the tubulin binding region, suggesting that cypin's binding to tubulin heterodimers is not sufficient for the promotion of microtubule assembly.

Example 7

Treatments that Increase Dendrite Number Increase Cypin

As it has been established cypin plays a physiological role in the regulation of dendrite number, it was expected that cypin protein expression will increase when neurons are treated with agents that have been reported to increase dendrite number, such as KCl or NGF. (Vaillant et al., Neuron 34:985 (2002); McAllister et al., Neuron 17:1057 (1996); Huang et al., Annu. Rev. Neurosci. 24:677 (2001); Zhang, et al., Nat. Neurosci. 4 (Suppl):1207 (2001); Yu & Malenka, Nat. Neurosci. 6:1169 (2003)). To confirm this occurs, cultured rat hippocampal neurons (7 d.i.v.) were treated with increasing amounts of these agents for 3 days. Cypin was assayed for in extracts of these treated neurons by Western blotting. Treatment with increasing amounts of KCl results in increased cypin protein expression (Akum et al., Nature Neurosci. 7:145 (2004)). This increase in cypin protein was accompanied by an increase in guanine deaminase activity (Id.). Furthermore, no increase in actin was observed, showing that the treatments do not upregulate all proteins in the neuron (Id.). Additionally, an increase in cypin expression was observed when neurons were exposed to NGF; however, the increase was not as great as that found with KCl treatment (Id.).

Example 8

Regulators of Dendrite Number Increase Cypin Protein Expression

Cypin regulates dendrite number and treatment of neurons with neurotrophins increases cypin protein levels. BDNF is a neurotrophin known to play an important role in learning and memory. Much of the literature reports that BDNF is the major neurotrophin that increases dendrite number in cortical neurons and that BDNF acts on electrically active neurons (e.g., McAllister et al., Neuron 15:791 (1995); McAllister et al., Neuron 17:1057 (1996); McAllister et al., Neuron 18:767 (1997); Baker et al., Eur. J. Neurosci. 10:1037 (1998); Horch et al., Neuron 23: 353 (1999); Lom and Cohen-Cory, J. Neurosci. 19:9928 (1999); Vaillant et al., Neuron 34:985 (2002)). In addition, there are a number of reports supporting the fact that BDNF increases dendrite number (e.g., Tolwani et al., Neuroscience 114:795 (2002). Furthermore, there is evidence that some subpopulations of Alzheimer's patients have altered BDNF or BDNF precursor (pro form) levels (Narisawa-Saito and Nawa, J. Neurochem. 67:1124 (1996); Lapchak et al., Neuroscience 53:297 (1993)).

To assess whether treatment of hippocampal cultures with BDNF increases cypin protein expression, cultures were treated with BDNF and assayed for cypin protein levels by Western blotting. Cypin protein levels were determined to increase with treatments of increasing concentrations of BDNF.

Since BDNF, KCl, and NGF increase cypin protein levels and cypin increases dendrite number in a dose dependent manner, cypin may be a common mediator for extrinsic factors that increase dendrite number. This suggests that cypin is a therapeutic target for cognitive disorders such as Alzheimer's Disease.

Example 9

Neurons Enriched in Cypin are Enriched in nNOS

Neuronal nitric oxide synthase ("nNOS") is an enzyme that is enriched in certain subpopulations of neurons. Inhibitory interneurons are enriched in nNOS and have more dendrites than pyramidal neurons. Furthermore, these neurons are enriched in cypin in the adult rat brain, as compared to pyramidal neurons (Firestein et al., Neuron 24:659 (1999)). Since cypin regulates neuronal morphology and is developmentally regulated in interneurons, it was tested whether cypin is developmentally regulated in these neurons. Results demonstrated that 80% of all neurons that are enriched in cypin at 1 d.i.v., 4, and 7 are also enriched in nNOS and that the majority of neurons enriched in nNOS are also enriched in cypin (Akum et al., Nature Neurosci. 7:145 (2004)). Furthermore, these neurons represented less than 10% of the total neurons, consistent with the number of inhibitory interneurons in culture (Firestein et al., Neuron 24:659 (1999)). This suggests that cypin is enriched in inhibitory neurons very early in culture.

Example 10

Cypin Regulates Dendrite Branching in Mature Neurons

The main functions of cypin protein are its guanine deaminase activity (mediated by a zinc-binding and a CRMP homology domain) (Akum et al., Nature Neurosci. 7:145 (2004), and its PDZ binding domain, which can interact with PSD-95 (Firestein et al., Neuron 24:669 (1999)). To determine whether the increase in dendrite number mediated by cypin is due to either of these functions, rat hippocampal neurons were transfected with cDNAs encoding rat cypinΔ (76-84)-GFP (lacking the zinc-binding domain) or rat cypinΔ (350-403)-GFP (lacking CRMP homology domain), as described above. Mutations in the zinc-binding and CRMP domains impaired cypin's ability to increase dendrite number at both 12 and 17 d.i.v. This suggests that cypin guanine deaminase activity is required to induce new dendrites, whereas its interaction with a PDZ protein through its PDZ-binding domain (loss of which, as described above, results in excessive pruning of secondary dendrites in cultures from 12 d.i.v. to 17 d.i.v.) is required to maintain the dendrites as neurons mature.

Example 11

A Role for PSD-95 in Dendrite Branching

The PDZ-binding domain of cypin is known to interact with PSD-95 and plays a role in stabilizing dendrites. To determine whether PSD-95 plays a role in dendrite branching, PSD-95 was overexpressed and dendrites counted at 12 and 17 d.i.v. Overexpression of PSD-95 for forty eight hours (12 d.i.v.) resulted in a decrease in the number of secondary dendrites. By 17 d.i.v., PSD-95 overexpression had no effect on the numbers of primary or secondary dendrites, even though PSD-95 levels persisted until 17 d.i.v. This indicates that the dendrites induced by overexpression of PSD-95 are not stable.

Simultaneous manipulations of cypin and PSD-95 levels were performed to determine whether the effect of one molecule or the other would predominate. Both rat cypin and PSD-95 were overexpressed and dendrites counted at 12 and 17 d.i.v. Overexpressing PSD-95 attenuated the increase in secondary dendrite number promoted by overexpressing cypin at both 12 and 17 d.i.v. The data indicates that elevated PSD-95 levels can suppress dendrite branching, even when cypin levels are elevated, suggesting that cypin might regulate branching by antagonizing PSD-95.

If cypin does regulate dendrite branching by antagonizing PSD-95, then it would be expected that the effects of reducing cypin and overexpressing PSD-95 should affect the same process and thus not be additive. Simultaneously knocking down cypin levels with a 5' end mutated U1 snRNA, as described in Akum et al., Nature Neurosci. 7:145 (2004), and overexpressing PSD-95 did not reduce dendrite number at 12 and 17 d.i.v. over that seen with either single manipulation alone. At 12 d.i.v., but not at 17 d.i.v., however, overexpression of PSD-95 while cypin was knocked down brought the number of primary and secondary dendrites back to control levels. This suggests that elevating the levels of PSD-95 occludes the effect of reducing cypin levels, and is consistent with a model whereby cypin regulates dendrite branching, at least in part, by antagonizing PSD-95.

Example 12

Cypin and PSD-95 Interactions Control Dendrite Growth Rate

Overexpression of cypin can increase dendrite number at both 12 and 17 d.i.v. In contrast, overexpression of cypin lacking the PDZ binding site can induce dendrites at 12 d.i.v. which cannot be detected by 17 d.i.v., suggesting that the dendrites induced by this mutant protein are transient. To examine the pattern of these transient dendrites more closely, the relationship of secondary dendrites to primary dendrites was used as a measure of how "aggressive" the dendrite growth pattern is for each mutant using the slope of secondary versus primary as an indicator of growth rate. Rat cypin-GFP induced more aggressive growth at 12 d.i.v. than at 17 d.i.v. Mutations that impair guanine deaminase activity (cypin (Δ76-84)-GFP and cypin(Δ350-403)-GFP) impaired the aggressive growth induced at 12 d.i.v. by cypin back to the level of GFP. Interestingly, deletion of the PDZ-binding domain (cypin-PDZ-GFP) also reduced the aggressive growth induced at 12 d.i.v. by cypin with a rate equal to that of GFP alone. This indicates that cypin can regulate not only the number of dendrite branches but also the pattern of dendrite branching, and that this regulation is dependent on guanine deaminase activity and PDZ binding.

To investigate how the interaction between cypin and PSD-95 acts to regulate dendrite patterning, the same analysis was applied when PSD-95 was overexpressed. On 12 d.i.v., PSD-95 did not change the basal (GFP) growth rate; however, it did bring the aggressive growth rate of cypin alone back to the basal growth rate. These results support the conclusion that PSD-95 acts to stop secondary branching. Taken together, the data suggest that the interaction between cypin and PSD-95 determines where a dendrite will branch and increases the rate of secondary dendrite growth. If cypin cannot bind to PSD-95 to decrease clustering, as in the case of cypin-PDZ or overexpression of PSD-95, stable secondary dendrites will not form.

Example 13

Knocking Down PSD-95 Results in Increased Secondary Dendrites

If PSD-95 acts as a stop signal for branching and therefore, decreasing PSD-95 expression should result in an increase in secondary dendrites. To test this hypothesis, a 5' end mutated U1 snRNA corresponding to a region in the 3' UTR of PSD-95 was constructed using the methodology described in Akum et al., Nature Neurosci. 7:145 (2004). Neurons were transfected with a cDNA encoding this U1 snRNA and assessed for endogenous PSD-95 levels by immunostaining. When the construct was expressed from 10-12 d.i.v., PSD-95 levels did not change as determined by clusters per area, cluster size, or intensity; however, when the construct was expressed from 10-17 d.i.v., both cluster size and intensity significantly decreased. Dendrite numbers in these neurons, as well as in neurons transfected with vector alone, were then assessed. Knocking down PSD-95 had no significant effect on primary dendrite number. This knockdown, however, significantly increased secondary dendrite number. Furthermore, expression of PSD-95 when endogenous PSD-95 is knocked down brought the number of secondary dendrites back to control levels. This data supports the conclusion that PSD-95 acts as a stop signal for proximal dendrite branching in neurons.

Example 14

Cypin Regulates PSD-95 Clustering

Cypin decreases PSD-95 and SAP-102 clustering at postsynaptic sites (Firestein et al., Neuron 24:659 (1999)). Since binding of cypin to PSD-95 family members plays a role in regulating dendrite number, mutants of cypin were analyzed to determine if they have an effect on the clustering of the PSD-95 at 12 d.i.v. Overexpression of rat cypin resulted in a decreased number and size of endogenous PSD-95 clusters. Furthermore, deletion of the zinc-binding (cypin(Δ76-84)-GFP) or the CRMP-homology (amino cypin(Δ350-403)-GFP) domains of cypin, both of which attenuate cypin's activity to promote increases in dendrite number, result in disruption of cypin's effect on the number of PSD-95 clusters per unit area, but do act like wildtype cypin to decrease cluster size. Deletion of these regions results in guanine deaminase activity with slower kinetics than that of wild-type cypin (Akum et al., Nature Neurosci. 7:145 (2004)). Thus, the slower activity results in a partial phenotype, supporting the conclusion that guanine deaminase activity plays a role in PSD-95 localization by cypin. In addition, cypin lacking the PDZ binding motif (cypin-PDZ-GFP) had no effect on PSD-95 clustering. These results suggest that there are common domains that mediate both cypin's ability to decrease PSD-95 clustering and to increase dendrite number and that these two processes may be related and dependent on guanine deaminase activity. Taken together, the results indicate that the same domains of cypin that are required for dendrite branching are also required to antagonize PSD-95 clustering.

To test the hypothesis that cypin plays a role in regulating the amount of PSD-95 family member proteins that localize to synaptic sites, cypin protein levels in rat hippocampal neurons were knocked down with cDNAs encoding 5'-end mutated U1 snRNAs as described in Akum et al., Nature Neurosci. 7:145 (2004). Although the number of PSD-95 clusters was unchanged, the size and intensity of PSD-95 clusters increased when cypin levels were knocked down by the U1-3'UTR vector. When endogenous cypin was replaced with cypin GFP (U1-3'UTR+cypin-GFP), clusters per unit area returned to control levels, indicating a role for cypin in regulating PSD-95 family member localization.

Example 15 mRNA Binding to Cypin

Using the methodology of Trifillis et al., RNA 5:1071 (1999); Rodgers et al., Methods 26:115 (2002), and Jiao et al., Biol. Reprod. 66:475 (2002), it was found that cypin binds to several mRNAs known be mis-regulated in certain cognitive disorders, such as Cri-du-Chat syndrome, Down Syndrome, and Parkinson's Disease. These mRNAs include the Down Syndrome critical region transcript (Acc. No. U17628), tyrosine-3-monooxygenase (Acc. No. NM_145690), D-dopachrome tautomerase (Acc. No. NM_001355), and *Homo sapien* clone HEA6 Cri-du-Chat region mRNA (Acc. No. AF009284). This lends support to the conclusion that cypin is both a marker for cognitive disorders, as well as a target for treatment of such disorders.

All publications cited in the specification, both patent publications and non-patent publications, are indicative of the level of skill of those skilled in the art to which this invention pertains. All these publications are herein fully incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

What is claimed:

1. An isolated polypeptide consisting of amino acids 221-454 of a polypeptide selected from the group consisting of SEQ ID NO: 1, 3, 5 and 7.

2. An isolated polypeptide consisting of amino acids 1-450 of a polypeptide selected from a group consisting of SEQ ID NO: 1, 3, 5 and 7.

3. An isolated polypeptide consisting of amino acids 350-454 of a polypeptide selected from a group consisting SEQ ID NO: 1, 3, 5 and 7.

4. An isolated polypeptide consisting of amino acids 1-220 of a polypeptide selected from a group consisting of SEQ ID NO: 1, 3, 5 and 7.

5. An isolated polypeptide comprising an amino acid sequence selected from the group consisting of SEQ ID NOs: 9-20.

6. The isolated polypeptide of claim 5 comprising an amino acid sequence selected from the group consisting of SEQ ID NO: 9-12.

7. The isolated polypeptide of claim 5 comprising an amino acid sequence selected from the group consisting of SEQ ID NO: 13-16.

8. The isolated polypeptide of claim 5 comprising an amino acid sequence selected from the group consisting of SEQ ID NO: 17-20.

* * * * *